US010294305B2

(12) United States Patent
Loibner et al.

(10) Patent No.: US 10,294,305 B2
(45) **Date of Patent: *May 21, 2019**

(54) METHOD FOR TREATING A GD2 POSITIVE CANCER

(71) Applicant: APEIRON BIOLOGICS AG, Vienna (AT)

(72) Inventors: Hans Loibner, Vienna (AT); Oliver Mutschlechner, Wiener Neudorf (AT); Ruth Ladenstein, Vienna (AT); Isabel Klier, Vienna (AT)

(73) Assignee: APEIRON BIOLOGICS AG, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 14/182,776

(22) Filed: Feb. 18, 2014

(65) Prior Publication Data

US 2014/0170155 A1 Jun. 19, 2014

Related U.S. Application Data

(63) Continuation of application No. 14/086,696, filed on Nov. 21, 2013, now abandoned, which is a continuation-in-part of application No. PCT/EP2012/064970, filed on Jul. 31, 2012, which is a continuation-in-part of application No. PCT/EP2012/061618, filed on Jun. 18, 2012.

(51) Int. Cl.

| | |
|---|---|
| ***C07K 14/55*** | (2006.01) |
| ***C07K 16/28*** | (2006.01) |
| ***A61K 31/485*** | (2006.01) |
| ***A61K 45/06*** | (2006.01) |
| ***C07K 16/30*** | (2006.01) |
| ***A61K 39/395*** | (2006.01) |
| *A61K 39/00* | (2006.01) |

(52) U.S. Cl.

CPC ........ *C07K 16/3084* (2013.01); *A61K 31/485* (2013.01); *A61K 39/39533* (2013.01); *A61K 39/39558* (2013.01); *A61K 45/06* (2013.01); *C07K 14/55* (2013.01); *C07K 16/28* (2013.01); *A61K 2039/505* (2013.01); *A61K 2039/54* (2013.01); *A61K 2039/545* (2013.01); *C07K 2317/24* (2013.01); *C07K 2317/732* (2013.01); *C07K 2317/734* (2013.01); *C07K 2317/76* (2013.01); *C07K 2319/00* (2013.01)

(58) Field of Classification Search

CPC .... C07K 16/3084; C07K 14/55; C07K 16/28; A61K 31/485; A61K 39/39533; A61K 39/39558; A61K 45/06

USPC ........................................................ 424/139.1

See application file for complete search history.

(56) References Cited

U.S. PATENT DOCUMENTS

| | | | |
|---|---|---|---|
| 7,833,525 B2 * | 11/2010 | Shenoy et al. | 424/130.1 |
| 9,777,068 B2 * | 10/2017 | Loibner | C07K 16/3084 |
| 9,840,566 B2 * | 12/2017 | Loibner | C07K 16/3084 |
| 2014/0170155 A1 | 6/2014 | Loibner et al. | 424/139.1 |
| 2015/0139942 A1 | 5/2015 | Loibner et al. | |
| 2016/0304620 A1 * | 10/2016 | Loibner | C07K 16/3084 |
| 2018/0134801 A1 * | 5/2018 | Loibner | A61K 31/485 |
| 2018/0258183 A1 * | 9/2018 | Loibner | C07K 16/3084 |

FOREIGN PATENT DOCUMENTS

| | | |
|---|---|---|
| JP | 2006-521085 | 9/2006 |
| JP | 2006521085 | 9/2006 |
| WO | WO 2005/070967 | 8/2005 |
| WO | WO 2008/049643 | 5/2008 |
| WO | WO 2011/160119 | 12/2011 |
| WO | WO 2013/189516 | 12/2013 |
| WO | WO 2013/189554 | 12/2013 |

OTHER PUBLICATIONS

Raffaghello et al. Cancer Letters 197 (2003) (205-209).*
Mujoo et al. (Cancer Res. 49 (1989) 2857-2861.*
Kowalczyk et al. Cancer Letters 281 (2009) 171-182.*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Vriesendorp et al. Cancer 18(12 Suppl) (1997) 2642-9.*
Balwierz et al., (Przegl Lek 67:387-92 (2010); Abstract only).*
Drozynska et al., Med Wieku Rozwoj 11(3 Pt 2):325-30 (Jul.-Sep. 2011); Abstract only).*
Aperion Biologics website ("Managed Access Program"; pp. 1-3; Jul. 26, 2017).*
Batova et al., "The Ch14.18-GM-CSF fusion protein is effective at mediating antibody-dependent cellular cytotoxicity and complement-dependent cytotoxicity in vitro", *Clin. Cancer Res.*, 5(12):4259-4263, 1999.
Chames and Baty, "Bispecific antibodies for cancer therapy: the light at the end of the tunnel?", *MAbs*, 1(6):539-547, 2009.
Frost et al., "A phase I/IB trial of murine monoclonal anti-GD2 antibody 14.G2a plus interleukin-2 in children with refractory neuroblastoma: a report of the Children's Cancer Group", *Cancer*, 80(2):317-333, 1997.

(Continued)

*Primary Examiner* — Lynn A Bristol

(74) *Attorney, Agent, or Firm* — Norton Rose Fulbright US LLP

(57) ABSTRACT

Preparations and methods for treating a GD2 positive cancer by administering a preparation comprising an anti-GD2 antibody to a patient, wherein the patient is not concomitantly treated with Interleukin-2 (IL-2), and wherein one or more treatment periods with the antibody may be preceded, accompanied, and/or followed by one or more treatment periods with a retinoid.

21 Claims, 34 Drawing Sheets

Specification includes a Sequence Listing.

(56) References Cited

OTHER PUBLICATIONS

Handgretinger et al., "A phase I study of human/mouse chimeric antiganglioside GD2 antibody ch14.18 in patients with neuroblastoma", *Eur. J. Cancer*, 31A(2):261-267, 1995.
Idusogie et al., "Mapping of the C1q binding site on rituxan, a chimeric antibody with a human IgG1 Fc", *J. Immunol*, 164(8):4178-4184, 2000.
International Search Report issued in PCT Appl No. PCT/EP2012/061618, dated Jan. 7, 2013.
International Search Report issued in PCT Appl. No. PCT/EP2012/064970, dated Jan. 11, 2013.
Lode and Dobke, "A Phase I/II Dose Schedule Finding Study of ch14.18/CHO Continuous Infusion Combined with Subcutaneious Aldesleukin (=Proleukin) (IL-2) in Pateints with Primary refractory or Relapsed Neuroblastoma. A SIOPEN Study", 3 pages, 2012, <http://www.kinderkrebsinfo.de/health_professionals/clinical_trials/phase_i_ii_trials_in_the_gpoh/longterminfusion_study_lti_ch1418/index_eng.html>, retrieved Dec. 10, 2012.
Mueller et al., "Enhancement of antibody-dependent cytotoxicity with a chimeric anti-GD2 antibody", *J. Immunol.*, 144(4):1382-1386, 1990.
Murray et al., "Phase I trial of murine monoclonal antibody 14G2a administered by prolonged intravenous infusion in patients with neuroectodermal tumors", *Journal of Clinical Oncology*, 12(1):184-193, 1994.
Navid et al., "Anti-GD2 antibody therapy for GD2-expressing tumors", *Curr. Cancer Drug Targets*, 10(2):200-209, 2010.
Saleh et al., "Phase I trial of the murine monoclonal anti-GD2 antibody 14G2a in metastatic melanoma", *Cancer Research*, 52(16):4342-4347, 1992.
Shusterman et al., "Antitumor activity of hu14.18-IL2 in patients with relapsed/refractory neuroblastoma: a Children's Oncology Group (COG) phase II study", *J Clin Oncol.*, 28(33):4969-4975, 2010.
Yu et al., "Anti-GD2 antibody with GM-CSF, interleukin-2, and isotretinoin for neuroblastoma", *New England Journal of Medicine*, 363(14):1324-1334, 2010.
Yu et al., "Phase I trial of a human-mouse chimeric anti-disialoganglioside monoclonal antibody ch14.18 in patients with refractory neuroblastoma and osteosarcoma", *Journal of Clinical Oncology*, 16(6):2169-2180, 1998.
Zeng et al., "Anti-neuroblastoma effect of ch14.18 antibody produced in CHO cells is mediated by NK-cells in mice", *Molecular Immunology*, 42(11):1311-1319, 2005.
Gilman, A.L. et al: "Phase I Study of ch14.18 With Granulocyte-Macrophage Colony-Stimulating Factor and Interleukin-2 in Children With Neuroblastoma After Autologous Bone Marrow Transplantation or Stem-Cell Rescue: A Report From the Children's Oncology Group", Journal of Clinical Oncology, vol. 27, No. 1, (Nov. 24, 2008), pp. 85-91.
Handgretinger, Rupert et al: "A phase I study of neuroblastoma with the anti-ganglioside GD2 antibody 14.G2a", *Cancer Immunology and Immunotherapy, Springerverlag*, Berlin, DE, vol. 35, No. 3, Jan. 1, 1992 (Jan. 1, 1992 ), pp. 199-204.
Ozkaynak, M. F.: "Phase I study of chimeric human/murine antiganglioside GD2 monoclonal antibody (ch14.18) with granulocyte-macrophage colony-stimulating factor in children with neuroblastoma immediately after hematopoietic stem-cell transplantation: A Children's Cancer Group study", Journal of Clinical Oncology, American Society of Clinical Oncology, US, vol. 18, No. 24, (Dec. 15, 2000), pp. 4077-4085.
"High Risk Neuroblastoma Study 1 of SIOP-Europe (SIOPEN)", SIOP, Jul. 1, 2009, pp. 1-303, Retrieved from the Internet: URL:http://www.oncauvergne.fr/index.php?option=com_docman&task=doc_download&gid=928&Itemid= [retrieved on Mar. 27, 2014].
"Press Release: Oncology Alliance. Apeiron, CCRI and SIOPEN Join Forces against Neuroblastoma", Apeiron Biologics AG., Jun. 2011, 8 pages. Vienna. Retrieved from the internet: URL:http://www.life-sciences-germany.com/news/apeiron-ccri-siopen-neuroblastoma-biologics-group-forschungs-und-2001-97329.html [retrieved on Mar. 20, 2014].
Castel et al., "Treatment of high-risk neuroblastoma with anti-GD2 antibodies", Clinical and Translational Oncology, 12(12): 788-793, 2010.
Gains et al., "Ten challenges in the management of neuroblastoma", Future Oncology, 8(7): 839-858, 2012.
Kushner et al., "Phase II trial of the anti-GD2 monoclonal antibody 3F8 and granulocyte-macrophage colony-stimulating factor for neuroblastoma", Journal of Clinical Oncology, 19(22): 4189-4194, 2001.
Lode et al., "Long-term continuous infusion of anti-GD2 antibody CH14.18/CHO in relapsed/refractory neuroblastoma patients", Journal for ImmunoTherapy of Cancer, 1(Suppl 1): 244, 2013.
Office Action issued in European Patent Application No. 13193953.0, dated Apr. 16, 2014.
Simon, "Consolidation Treatment With Chimeric Anti-GD2-Antibody ch14. 18 in Children Older than 1 Year With Metastatic Neuroblastoma", Journal of Clinical Oncology, 22(17): 3549-3557, 2004.
Cheung et al, "Humanizing murine lgG3 anti-GD2 antibody m3F8 substantially improves antibody-dependent cell-mediated cytotoxicity while retaining targeting in vivo," *OncoImmunology*, 1.4, (Jul. 2012): 447-486).
NCT00072358, "Phase II Study of Anti-GD2 3F8 Antibody nd GM-CSF for High-Risk Neuroblastoma," ClinicalTrials.gov archive, version Jul. 8, 2013.
Simon et al. "Long term outcome of high-risk neuroblastoma patients after immunotherapy with antibody ch14.18 or oral metronomic chemotherapy," *BMC Cancer* 11(21): 2011, 8pp.
Office Action issued in Japanese Patent Application No. 2015-517621, dated Jun. 28, 2016.
Coping with Ch14.18, Children's Neuroblastoma Cancer Foundation, Revised Jul. 31, 2012 www.cncfhope.org.
Ladenstein, et al., "Ch14.18 Antibody Produced in CHO Cells in Relapsed or Refractory Stage 4 Neuroblastoma Patients," *mAbs*, 5(5), 801-809, 2013.

* cited by examiner

Treatment schedule ch14.18/CHO 100 mg/m²/cycle, 10 day: continuous infusion i.v.

aldesleukin (IL2) 60 x $10^6$ IU/m²/cycle, 10 days: two 5 day periods, 6 x $10^6$ IU/ m²/day s.c.

13-cis retinoid acid 2240 mg/m²/cycle, 14 days: 14 x 160 mg/m²/day p.o.

5 cycles; 35 day intervals

Morphine dose reduction in continuous versus non-continuous infusion

| *morphine application* | *SIOPEN phase I trial (n = 16)* | *continuous infusion pilot (n = 37)* |
|---|---|---|
| starting infusion rate | 50 μg/kg KG/h | 30 μg/kg KG/h |
| additional application (bolus) | 63% | 14% |
| dose increase | 50% | 16% |

Fig. 17

A
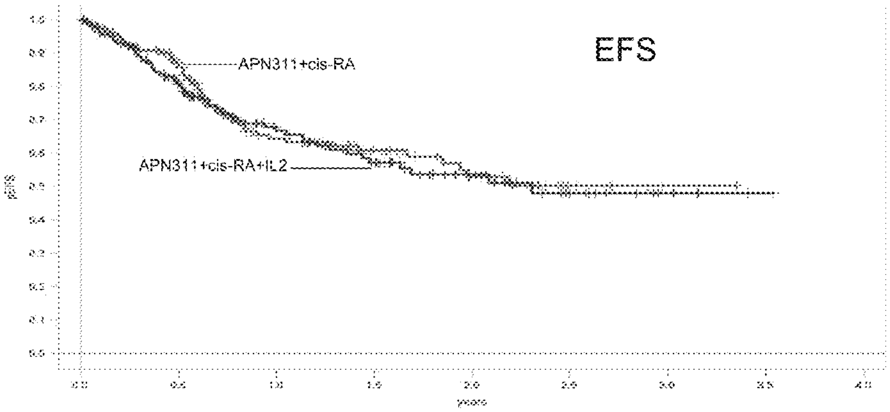
| | Patients | Events | 2-yrs. pEFS | p-value |
|---|---|---|---|---|
| APN311+cis-RA | 163 | 53 | 0.53±0.05 | 0.651 |
| APN311+cis-RA+IL2 | 165 | 57 | 0.54±0.05 | |
B
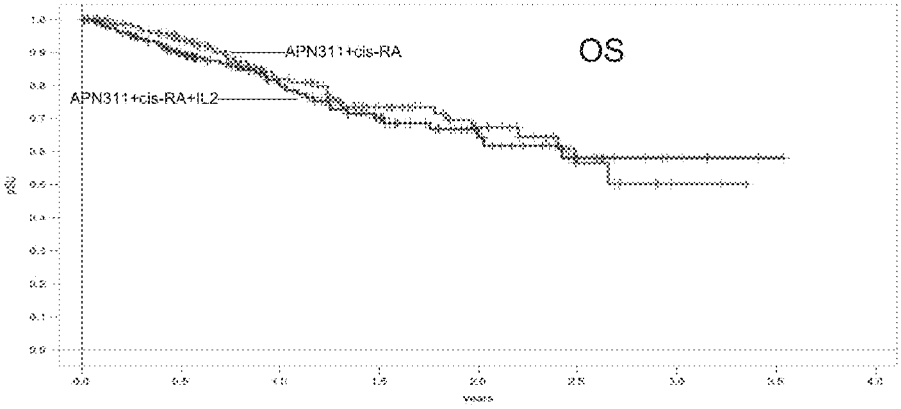
| | Patients | Events | 2-yrs. pEFS | p-value |
|---|---|---|---|---|
| APN311+cis-RA | 163 | 35 | 0.67±0.05 | 0.606 |
| APN311+cis-RA+IL2 | 165 | 39 | 0.64±0.05 | |
Fig. 18

| | All Grades | | Grades 3-4 | |
|---|---|---|---|---|
| Toxicity | % Patients ch14.18/CHO + 13-cis-RA | % Patients ch14.18/CHO + 13-cis-RA + IL2 | % Patients ch14.18/CHO + 13-cis-RA | % Patients ch14.18/CHO + 13-cis-RA + IL2 |
| Haemoglobin | 82% | 88% | 39% | 64% |
| WBC | 76% | 76% | 28% | 31% |
| General Condition | 72% | 83% | 18% | 40% |
| Fever | 72% | 79% | 14% | 37% |
| Granulocytes | 67% | 77% | 30% | 48% |
| Platelets | 63% | 79% | 33% | 59% |
| Skin | 59% | 72% | 5% | 9% |
| SGOT/SGPT | 55% | 60% | 14% | 19% |
| Infection | 52% | 61% | 25% | 30% |
| Allergy | 50% | 58% | 8% | 17% |
| Nausea/Vomiting | 48% | 66% | 4% | 8% |
| Diarrhoea | 45% | 63% | 5% | 20% |
| Constipation | 37% | 26% | 0% | 2% |
| Hypotension | 24% | 29% | 7% | 14% |
| Stomatitis | 15% | 22% | 2% | 2% |
| Hypertension | 12% | 5% | 4% | 0% |
| Creatinin | 10% | 16% | 1% | 1% |
| Haematuria | 10% | 10% | 0% | 0% |
| Glomular filtration rate | 7% | 6% | 2% | 0% |
| Central neuro | 7% | 16% | 2% | 6% |
| Bilirubin | 7% | 17% | 2% | 4% |
| Ototoxicities | 7% | 11% | 2% | 5% |
| Proteinuria | 7% | 6% | 0% | 0% |
| Periph. neuro | 7% | 13% | 1% | 2% |
| Pulmo. tox. | 4% | 17% | 2% | 3% |
| Cardiac function | 3% | 4% | 2% | 2% |
| Echo LV/SV | 2% | 5% | 2% | 1% |
| VOD | 1% | 3% | 0% | 0% |
| Haemor. cyst | 0% | 2% | 0% | 0% |

Fig. 21

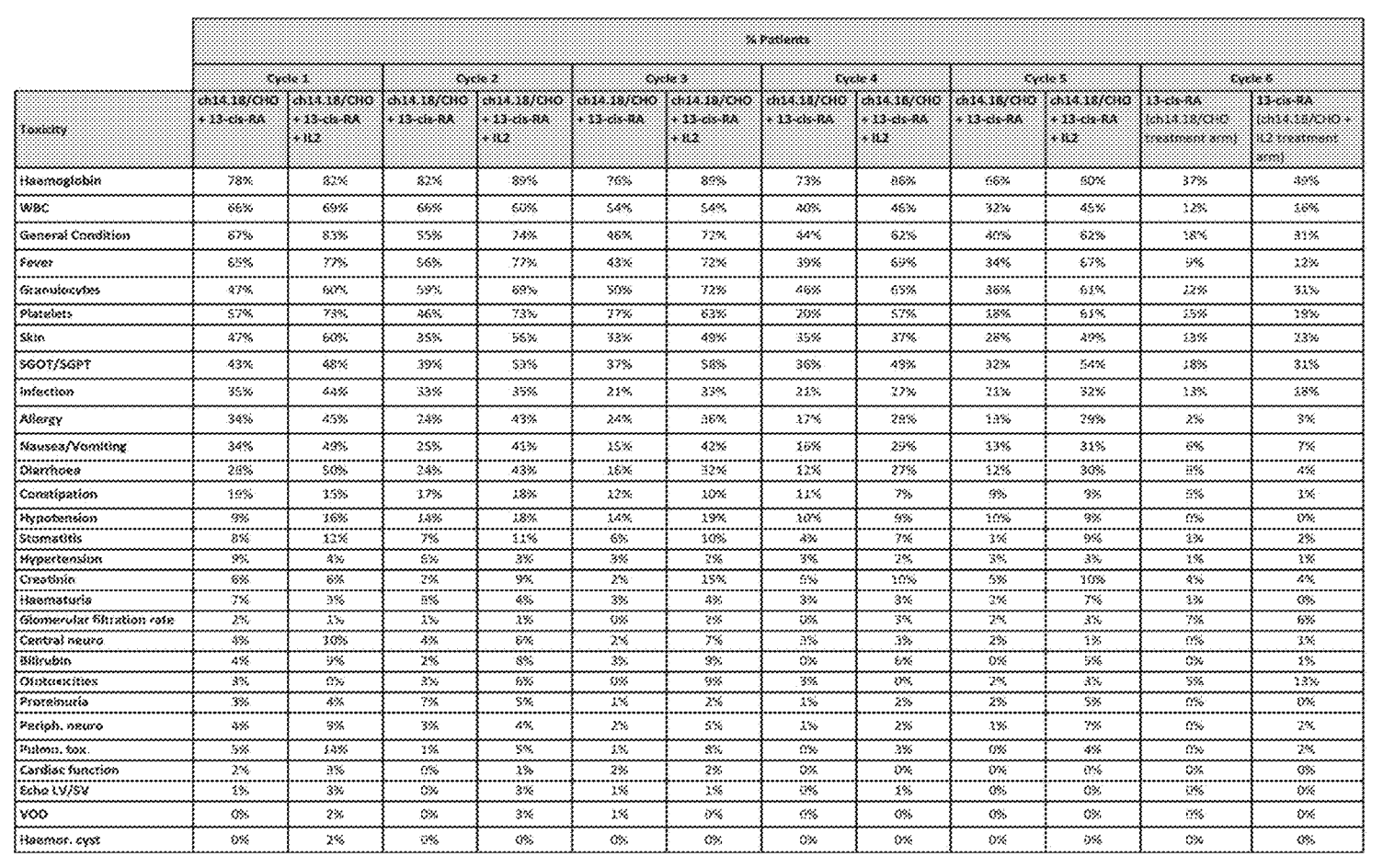

| Toxicity | % Patients | | | | | | | | | | | |
|---|---|---|---|---|---|---|---|---|---|---|---|---|
| | Cycle 1 | | Cycle 2 | | Cycle 3 | | Cycle 4 | | Cycle 5 | | Cycle 6 | |
| | ch14.18/CHO + 13-cis-RA | ch14.18/CHO + 13-cis-RA + IL2 | ch14.18/CHO + 13-cis-RA | ch14.18/CHO + 13-cis-RA + IL2 | ch14.18/CHO + 13-cis-RA | ch14.18/CHO + 13-cis-RA + IL2 | ch14.18/CHO + 13-cis-RA | ch14.18/CHO + 13-cis-RA + IL2 | ch14.18/CHO + 13-cis-RA | ch14.18/CHO + 13-cis-RA + IL2 | 13-cis-RA (ch14.18/CHO treatment arm) | 13-cis-RA (ch14.18/CHO + IL2 treatment arm) |
| Haemoglobin | 78% | 82% | 82% | 89% | 76% | 89% | 73% | 86% | 66% | 60% | 37% | 49% |
| WBC | 66% | 69% | 66% | 60% | 54% | 54% | 40% | 46% | 32% | 45% | 12% | 16% |
| General Condition | 67% | 83% | 55% | 74% | 48% | 72% | 44% | 62% | 40% | 62% | 18% | 31% |
| Fever | 65% | 77% | 56% | 77% | 43% | 72% | 39% | 69% | 34% | 67% | 9% | 12% |
| Granulocytes | 47% | 60% | 59% | 69% | 50% | 72% | 46% | 65% | 36% | 61% | 22% | 31% |
| Platelets | 57% | 73% | 46% | 73% | 27% | 63% | 20% | 57% | 18% | 61% | 15% | 19% |
| Skin | 47% | 60% | 35% | 56% | 33% | 49% | 35% | 37% | 28% | 49% | 13% | 23% |
| SGOT/SGPT | 43% | 48% | 39% | 53% | 37% | 58% | 36% | 49% | 32% | 54% | 18% | 31% |
| Infection | 35% | 44% | 33% | 35% | 21% | 33% | 21% | 27% | 21% | 32% | 13% | 18% |
| Allergy | 34% | 45% | 24% | 43% | 24% | 36% | 17% | 28% | 13% | 29% | 2% | 3% |
| Nausea/Vomiting | 34% | 49% | 25% | 41% | 15% | 42% | 16% | 29% | 13% | 31% | 6% | 7% |
| Diarrhoea | 28% | 50% | 24% | 43% | 18% | 32% | 12% | 27% | 12% | 30% | 8% | 4% |
| Constipation | 19% | 15% | 17% | 18% | 12% | 10% | 11% | 7% | 9% | 9% | 5% | 1% |
| Hypotension | 9% | 16% | 14% | 18% | 14% | 19% | 10% | 9% | 10% | 9% | 0% | 0% |
| Stomatitis | 8% | 12% | 7% | 11% | 6% | 10% | 4% | 7% | 1% | 9% | 1% | 2% |
| Hypertension | 9% | 4% | 6% | 3% | 3% | 2% | 3% | 2% | 3% | 3% | 1% | 1% |
| Creatinin | 6% | 6% | 2% | 9% | 2% | 15% | 5% | 10% | 5% | 10% | 4% | 4% |
| Haematuria | 7% | 3% | 8% | 4% | 3% | 4% | 3% | 3% | 2% | 7% | 1% | 0% |
| Glomerular filtration rate | 2% | 1% | 1% | 1% | 0% | 2% | 0% | 3% | 2% | 3% | 7% | 6% |
| Central neuro | 4% | 10% | 4% | 6% | 2% | 7% | 3% | 3% | 2% | 1% | 0% | 1% |
| Bilirubin | 4% | 9% | 2% | 8% | 3% | 9% | 0% | 6% | 0% | 5% | 0% | 1% |
| Ototoxicities | 3% | 0% | 3% | 6% | 0% | 9% | 3% | 0% | 2% | 3% | 5% | 13% |
| Proteinuria | 3% | 4% | 7% | 5% | 1% | 2% | 1% | 2% | 2% | 5% | 0% | 0% |
| Periph. neuro | 4% | 9% | 3% | 4% | 2% | 5% | 1% | 2% | 1% | 7% | 0% | 2% |
| Pulmo. tox. | 5% | 14% | 1% | 5% | 1% | 8% | 0% | 3% | 0% | 4% | 0% | 2% |
| Cardiac function | 2% | 3% | 0% | 1% | 2% | 2% | 0% | 0% | 0% | 0% | 0% | 0% |
| Echo LV/SV | 1% | 3% | 0% | 3% | 1% | 1% | 0% | 1% | 0% | 0% | 0% | 0% |
| VOD | 0% | 2% | 0% | 3% | 1% | 0% | 0% | 0% | 0% | 0% | 0% | 0% |
| Haemor. cyst | 0% | 2% | 0% | 0% | 0% | 0% | 0% | 0% | 0% | 0% | 0% | 0% |

Fig. 22

A
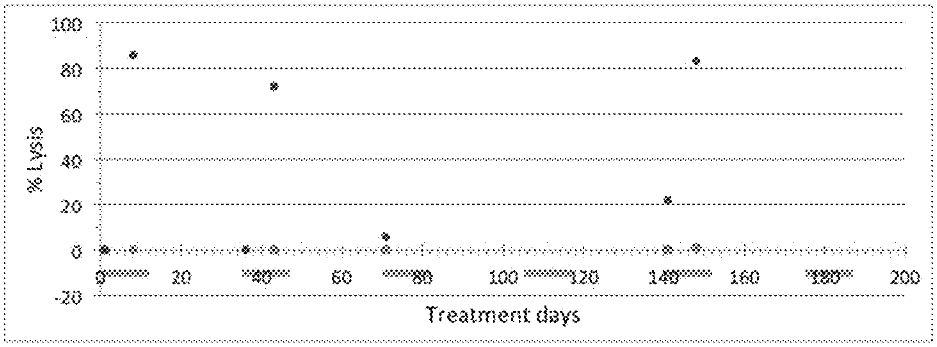
B
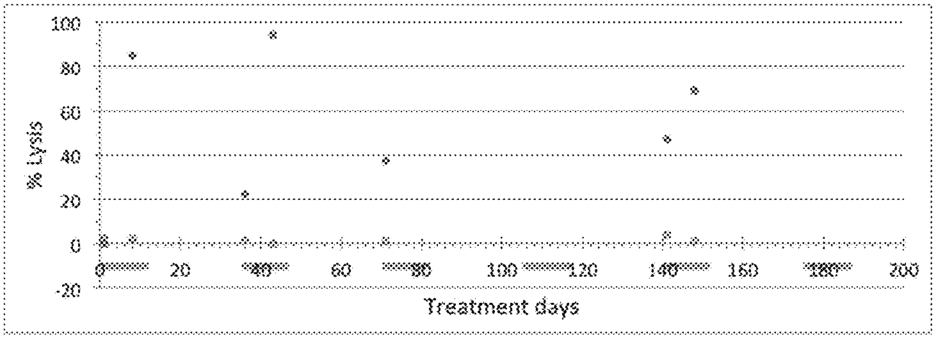
Fig. 33

A
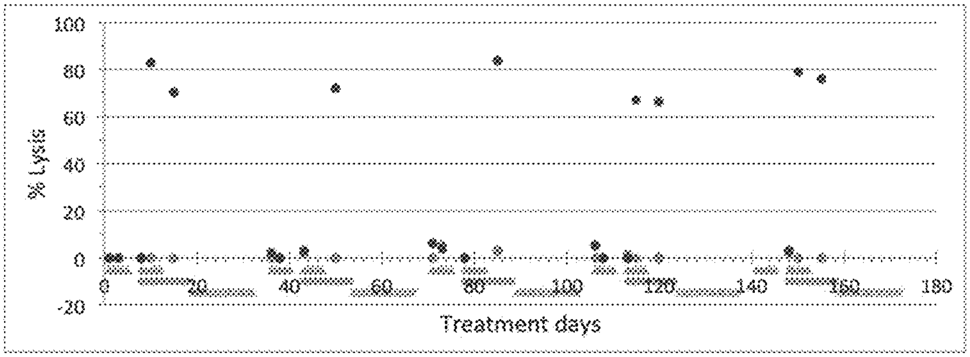
B
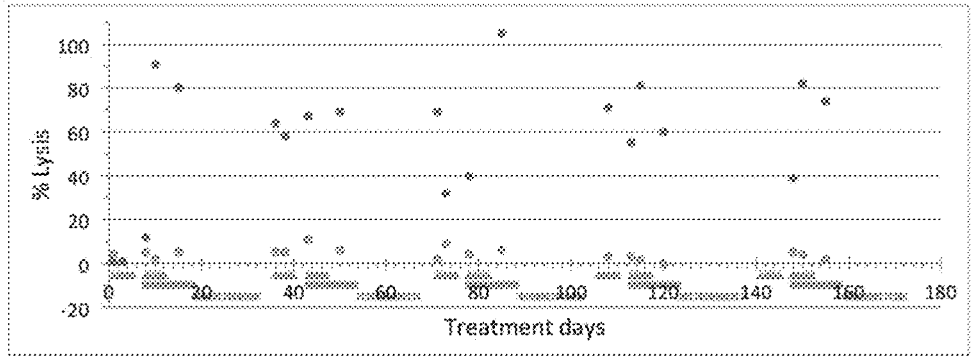
Fig. 34

METHOD FOR TREATING A GD2 POSITIVE CANCER

CROSS-REFERENCE TO RELATED APPLICATIONS

This application is a continuation of U.S. patent application Ser. No. 14/086,696 filed 21 Nov. 2013, abandoned, which is a continuation-in-part of International Application No. PCT/EP2012/064970 filed 31 Jul. 2012, which claims priority to International Application No. PCT/EP2012/061618 filed 18 Jun. 2012. The entire contents of each of the above-referenced disclosures is specifically incorporated by reference herein without disclaimer.

FIELD OF THE INVENTION

In a first aspect, the present invention relates to a method for treating a GD2 positive cancer by administering a preparation comprising an anti-GD2 antibody to a patient as a continuous intravenous infusion over 24 hours per day.

In a second aspect, the present invention relates to preparations and methods for treating a GD2 positive cancer by administering a preparation comprising an anti-GD2 antibody to a patient, wherein the patient is not concomitantly treated with Interleukin-2 (IL-2), and wherein one or more treatment periods with the antibody is/are preceded, accompanied, and/or followed by one or more treatment periods with a retinoid. In particular, the invention relates to preparations and methods for treating a GD2 positive cancer by administering a preparation comprising an anti-GD2 antibody to a patient, wherein the patient is not concomitantly treated with Interleukin-2 (IL-2), Granulocyte-macrophage colony-stimulating factor (GM-CSF), and/or one or more other cytokines. Furthermore, the invention relates to preparations and methods for the treatment of a GD2 positive cancer in a patient, wherein a preparation comprising an anti-GD2 antibody is administered to the patient as a continuous infusion for one or more days and for two or more treatment cycles, without concomitantly administering IL-2. The present invention further relates to preparations and methods for the treatment of a GD2 positive cancer in a patient, wherein a preparation comprising an anti-GD2 antibody is administered to the patient as a continuous infusion without concomitantly administering IL-2, and wherein the anti-GD2 antibody is not a 14G2a antibody.

BACKGROUND OF THE INVENTION

Neuroblastoma, after brain cancer, is the most frequent solid cancer in children under five years of age. In high-risk neuroblastoma, more than half of the patients receiving standard therapy have a relapse and ultimately die from the disease. 90% of cases occur between ages zero to six. The worldwide incidence in industrialized countries is around 2000 cases per year.

Monoclonal antibodies against specific antigens are increasingly being used in oncology. The entirely different mode of action compared to cytotoxic therapies have made them a valuable asset as is shown by forerunners like trastuzumab, cetuximab, bevacizumab, rituximab and others. The disialoganglioside GD2 is a glycosphingolipid expressed primarily on the cell surface. GD2 expression in normal tissues is rare and primarily restricted to the central nervous system (CNS), peripheral nerves and melanocytes. In cancerous cells, GD2 is uniformly expressed in neuroblastomas and most melanomas and to a variable degree in bone and soft-tissue sarcomas, small cell lung cancer, renal cell carcinoma, and brain tumors (Navid et al., Curr Cancer Drug Targets 2010; 10:200-209). Because of the relatively tumor-selective expression combined with its presence on the cell surface, GD2 represents a promising target for antibody-based cancer immunotherapy.

Accordingly, several anti-GD2 antibodies are subject to preclinical or clinical investigation in neuroblastoma, melanoma and other GD2-related cancers.

APN311 is a formulation of the chimeric monoclonal anti-GD2 antibody ch14.18 recombinantly produced in Chinese hamster ovary (CHO) cells, which is the standard mammalian cell line for production of commercially available antibodies. In a Phase I clinical study in relapsed/refractory neuroblastoma patients remissions were achieved with this antibody as single agent. A Phase III trial comprising treatment with APN311 was initiated in 2006 by the International Society of Paediatric Oncology European Neuroblastoma (SIOPEN) and is presently investigating the effects on event-free and overall survival related to treatment with APN311 together with isotretinoin, i.e. cis-retinoic acid (cis-RA), with or without s.c. IL-2. In a comparable US study using a treatment package of 4 drugs, namely a related antibody produced in SP2/0 murine hybridoma cells together with i.v. Interleukin-2 (IL-2 or IL2), Granulocyte-macrophage colony-stimulating factor (GM-CSF) and isotretinoin, interesting survival improvement was seen in children with neuroblastoma in complete remission following initial therapies and no evidence of disease.

APN301 is a formulation of an immunocytokine comprising a humanized anti-GD2 antibody (hu14.18) and IL-2 as a fusion protein. The antibody portion specifically binds to the GD2 antigen that is strongly expressed on neuroblastoma and several other cancers. IL-2 is a cytokine that recruits multiple immune effector cell types. In neuroblastoma patients, APN301 is designed to localize GD2-positive tumor cells via the antibody component. The fused IL-2 then stimulates the patient's immune system against the tumor by activation of both, NK and T cells, whereas the Fc portion of the antibody is designed to trigger tumor cell killing by antibody-dependent cellular cytotoxicity (ADCC) and complement-dependent cytotoxicity (CDC). The immunocytokine has shown activity in a Phase II clinical study in children with relapsed/refractory neuroblastoma (Shusterman et al.; JCO 2010 28 (33):4969-75.) and was also tested in a Phase I/II study in late stage malignant melanoma, showing immune activation.

Other anti-GD2 antibodies in research or development are, for example, the monoclonal antibody 3F8 (murine in phase II, as well as humanized in phase I), and 8B6 (specific to O-acetylated GD2, preclinical). Furthermore, anti-idiotypic antibodies such as e.g. 4B5, 1A7, and A1G4 have been under investigation as potential tumor vaccines, however, their development seems to be abandoned. WO 2008/049643 also describes anti-idiotypic antibodies, which mimic GD2 epitopes, i.e. GD2 mimotopes.

Another version of the 14.18 anti-GD2 antibody is hu14.18K322A as described in WO2005/070967, which has a point mutation in the Fc region in order to reduce CDC, but maintain ADCC, e.g. by expression in a cell line suitable for enhancing ADCC, such as YB2/0. The reduction in CDC is considered to result in reduced pain associated with the antibody treatment.

Anti-tumor activity of antibodies generally occurs via either complement dependent cytotoxicity (CDC or complement fixation) or through antibody dependent cell-mediated cytotoxicity (ADCC). These two activities are known in the art as "effector functions" and are mediated by antibodies, particularly of the IgG class. All of the IgG subclasses except IgG4 (IgG1, IgG2, IgG3) mediate ADCC and complement fixation to some extent, with IgG1 and IgG3 being most potent for both activities. ADCC is believed to occur when Fc receptors on natural killer (NK) cells and/or other Fc receptor bearing immune cells (effector cells) bind to the Fc region of antibodies bound to antigen on a cell's surface. Fc receptor binding signals the effector cell to kill the target cell. CDC is believed to occur by multiple mechanisms; one mechanism is initiated when an antibody binds to an antigen on a cell's surface. Once the antigen-antibody complex is formed, the C1q molecule is believed to bind the antigen-antibody complex. C1q then cleaves itself to initiate a cascade of enzymatic activation and cleavage of other complement proteins, which then bind the target cell surface and facilitate its death through, for example, cell lysis and/or ingestion by macrophages.

However, CDC is considered to cause the side effect of pain, especially for anti-GD2 antibodies. As described in WO2005/070967, neurons may be particularly sensitive to complement fixation because this process involves the creation of channels in a cell membrane, allowing an uncontrolled ion flux. In pain-sensing neurons, even a small amount of complement fixation may be significant to generate action potentials. Thus, any amount of CDC resulting from anti-GD2 antibody binding on neurons will result in pain. Accordingly, the prior art teaches that it is advantageous to reduce complement fixation so as to reduce the level of side effects in a patient and that the antitumor activity of anti-GD2 antibodies results primarily from ADCC, and not substantially from complement fixation (see e.g. WO2005/070967).

In contrast, a key aspect of the invention is that the cytolysis capacity of an anti-GD2 antibody determined by a CDC assay or a whole blood test (WBT) is essential for the anti-tumor effect of the anti-GD2 antibody. Such a WBT assay in contrast to CDC or ADCC assays measures the lytic potential of a heparinized whole blood sample. Thus, it does not only focus on one single effector mechanism but measures a combination of ADCC and CDC (and any other components and/or mechanisms present in the heparinized whole blood sample which might also be relevant to the lytic capacity against tumor cells) in a physiological setting. Accordingly, with the methods of the present invention it is possible to reduce the dose of the antibody to the minimal dose required for target cell lysis as determined by a CDC assay or a WBT. Furthermore, the methods of the invention allow to individually determine the effective antibody dose and thus, take into account the individual differences in anti-tumor responses of the patients. Another key aspect of the invention is that it is possible to reduce and manage the side effect of pain by determining the threshold dose of the anti-GD2 antibody to be administered to induce CDC and/or whole blood cytolytic activity. Another key finding of the invention is that the side effect of pain can be substantially reduced by administering the anti-GD2 antibody as a continuous infusion until the predetermined overall patient dose has been administered. Accordingly, with the methods according to the invention it is possible to substantially reduce the analgesic administration, especially the administration of strong analgesics such as morphine, during the antibody treatment, and thus, also substantially reduce the side effects of such analgesic administration.

As stated above, it is believed that antibody-dependent cellular cytotoxicity (ADCC) plays an important role in immunotherapy. Unfortunately, ADCC is often depressed in cancer patients. Cytokines are considered to augment ADCC by direct activation of immune cells or by enhancement of tumor-associated antigens (TAA) on tumor cells. For example, Aldesleukin (IL-2) causes activation of natural killer (NK) cells, generation of lymphokine-activated killer (LAK) cells, and augments ADCC. Aldesleukin (IL-2) has been effective at inducing measurable antitumor responses in patients with renal cell carcinoma and melanoma. Furthermore, GM-CSF has been shown both in vitro and in vivo to enhance antitumor immunity through direct activation of monocytes, macrophages, dendritic cells, and antibody-dependent cellular cytotoxicity (ADCC), and indirect T cell activation via TNF, interferon and interleukin 1 (IL-1). GM-CSF is considered to enhance functions of cells critical for immune activation against tumor cells, alone or with other cytokines or monoclonal antibodies.

Thus, in current clinical trials investigating anti-GD2 antibodies, in particular ch14.18, the antibody treatment is combined with cytokine treatment (and retinoid treatment), especially with IL-2 and/or GM-CSF. Accordingly, the prior art teaches that it is advantageous to administer cytokines to GD-2 positive cancer patients, in particular in combination with anti-GD2 antibody treatment.

In contrast, another key aspect of the invention is that such patients can be treated with an anti-GD2 antibody without IL-2, especially without any cytokine treatment.

The treatment with one or more cytokines in combination with the antibody may have severe side effects, such as e.g. fever, allergic reactions, hypotension, capillary leak syndrome etc., which may even lead to death. The accompanying cytokine treatment even potentiates adverse events of the antibody treatment, e.g. pain, since there is a synergy in adverse effects of both drugs. However, with the preparations and methods of the present invention, it is possible to completely omit any cytokine(s), especially IL-2. Thus, the present invention results in substantially reduced adverse effects of the treatment with the antibody.

SUMMARY OF THE INVENTION

In a first aspect, the present invention relates to a method for treating a GD2 positive cancer by administering a preparation comprising an anti-GD2 antibody to a patient as a continuous intravenous infusion over 24 hours per day. Said preparation comprising an anti-GD2 antibody may be administered by using a mini-pump, and may be administered for a treatment period until the predetermined overall patient dose has been administered.

Furthermore, the present invention relates to a method for treating a GD2 positive cancer by administering a preparation comprising an anti-GD2 antibody to a patient, wherein the preparation is administered in a dose sufficient to induce tumor cell lysis (cytolysis threshold dose), and wherein said cytolysis threshold dose is administered for a treatment period until the predetermined overall patient dose has been administered.

Moreover, the invention provides an anti-GD2 antibody for use in said treatment. In addition, the invention provides the use of an anti-GD2 antibody in the preparation of a medicament for said treatment.

In a second aspect, the present invention relates to preparations comprising an anti-GD2 antibody for use in the treatment of a GD2 positive cancer in a patient, wherein the preparation comprising an anti-GD2 antibody is administered to the patient without concomitantly administering IL-2, and wherein one or more treatment periods with the antibody is/are preceded, accompanied, and/or followed by one or more treatment periods with a retinoid.

Furthermore, the present invention relates to preparations comprising an anti-GD2 antibody for use in the treatment of a GD2 positive cancer in a patient, wherein the preparation comprising an anti-GD2 antibody is administered to the patient as a continuous infusion for one or more days and for two or more treatment cycles, without concomitantly administering IL-2.

Also, the present invention relates to preparations comprising an anti-GD2 antibody for use in the treatment of a GD2 positive cancer in a patient, wherein the preparation comprising an anti-GD2 antibody is administered to the patient as a continuous infusion without concomitantly administering IL-2, and wherein the anti-GD2 antibody is not a 14G2a antibody.

Moreover, the invention relates to methods of using the preparations for the treatment of a GD2 positive cancer in a patient.

The invention is further defined by the claims. All preferred embodiments of the invention as further described herein relate to all aspects of the invention equally and all of these aspects may be combined, e.g. the first with the second or third, the first with the second and third, the second with the third, to form a preparation for a method of the combined elements of these aspects; or to form combined methods.

BRIEF DESCRIPTION OF THE FIGURES

FIG. 17 shows the initial infusion rate of morphine administered during the antibody infusion in two different schedules (for the SIOPEN phase I trial: 8 h antibody infusion for 5 subsequent days; for the continuous infusion pilot schedule 24 h antibody infusion for 10 subsequent days), as well as the additional morphine administrations (given as a bolus) and the increases in the morphine infusion rate or the morphine dose that were required.

FIG. 18 shows Kaplan-Meier curves of the event-free survival (EFS, FIG. 18 A) and overall survival (OS, FIG. 18 B) data (in percent over time) of 328 neuroblastoma patients treated with APN311 and isotretinoin, but without IL-2 (in red) and patients treated with APN311 and isotretinoin and IL-2 (in blue).

FIG. 19 B shows a chart overlay for comparison.

FIG. 20 B shows a chart overlay for comparison.

FIGS. 21 and 22 show overview tables of the toxicities (FIG. 21: all grades of toxicities versus grade 3 and 4 only; FIG. 22: all grades of toxicities for each treatment cycle) observed in percent of total evaluated patients treated in the respective schedules with and without IL-2.

FIG. 24: grades 3 and 4 only) observed in all treatment cycles in percent of total evaluated patients treated in the respective schedules with and without IL-2.

FIG. 33 shows results of a complement-dependent cytotoxicity (CDC) assay (blue dots, FIG. 33 A) and a whole blood test (red dots, WBT, FIG. 33 B) of blood samples of a neuroblastoma patient during treatment with an anti-GD2 antibody, but without IL-2 and cis-retinioc acid treatment. The purple and grey dots are aliquots of patient samples treated with an anti-id antibody for differentiation of any potential non-specific lysis (i.e. target cell lysis that is not mediated by the antibody). The orange bars indicate the treatment periods with the antibody.

FIG. 34 shows results of a complement-dependent cytotoxicity (CDC) assay (blue dots, FIG. 34 A) and a whole blood test (red dots, WBT, FIG. 34 B) of blood samples of a neuroblastoma patient during treatment with an anti-GD2 antibody and with a usual IL-2 dose and cis-retinioc acid treatment. The purple and grey dots are aliquots of patient samples treated with an anti-id antibody for differentiation of any potential non-specific lysis (i.e. target cell lysis that is not mediated by the antibody). The orange bars indicate the treatment periods with the antibody, the green triangles the IL-2 treatment periods, and the light blue asterisks the cis-retinioc acid treatment periods.

DETAILED DESCRIPTION OF THE INVENTION

Figure 1:
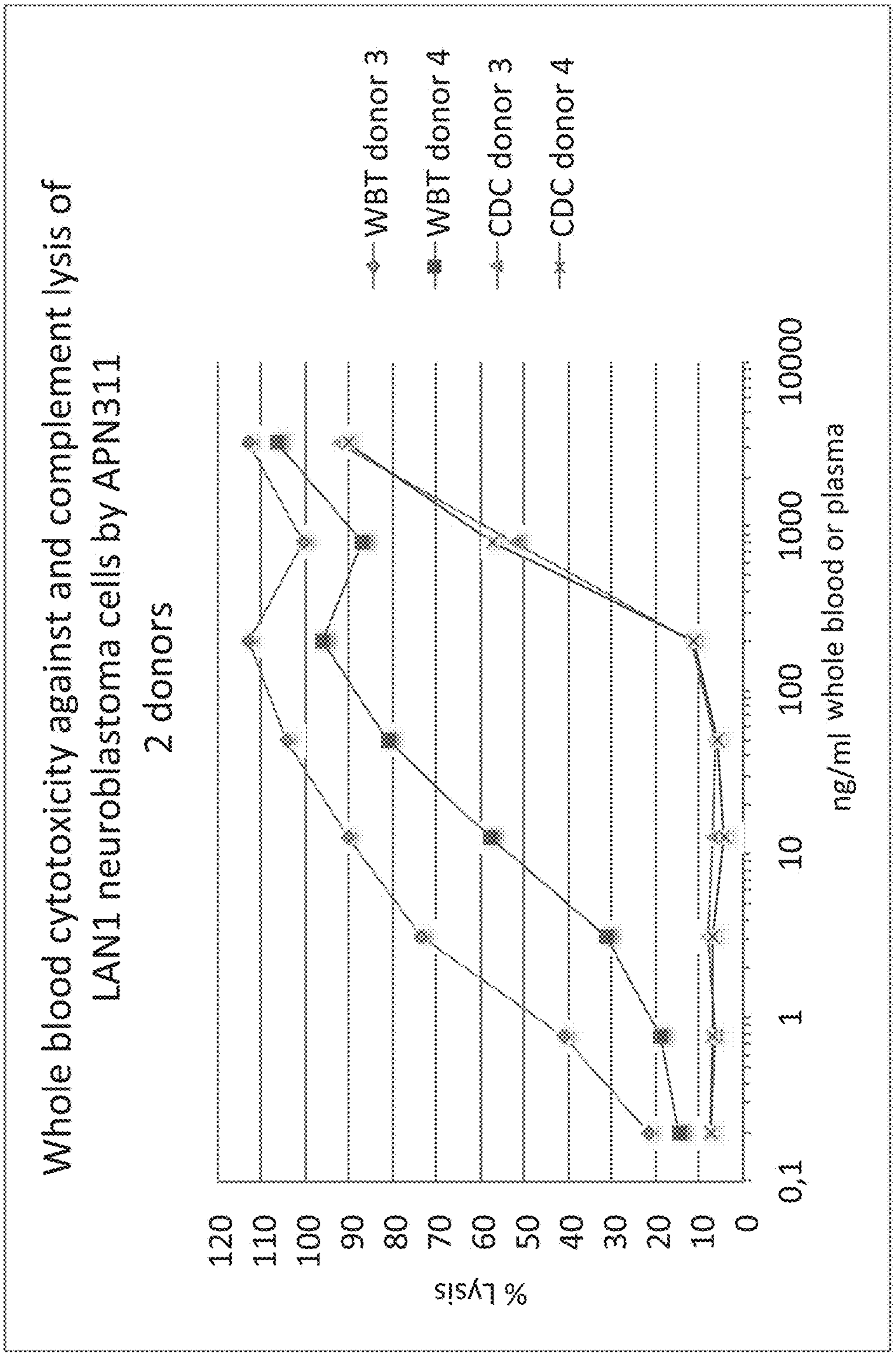
FIG. 1 shows the results of a WBT (with heparinized whole blood, using $^{51}$Cr labeled target human neuroblastoma cells) and a CDC assay (with heparinized plasma, also using $^{51}$Cr labeled target human neuroblastoma cells) of two healthy donors in the presence of APN311. As can be seen, there is a substantial difference in WBT lysis between the two donors: 50% lysis is reached at APN311 concentrations of 2 versus 10 ng/mL whole blood. However, there is no difference in CDC: 50% lysis of both donors is reached at APN311 concentrations of 1000 ng/ml plasma. In both assays (WBT and CDC assay), the same incubation time (20 h) has been used, as well as the same final concentration of complement.

In a first aspect, it has surprisingly turned out that a treatment with a preparation comprising an anti-GD2 antibody in a dose determined by cytolysis capacity, e.g. either measured by a CDC assay or by a WBT, has a beneficial effect in cancer therapy, especially on side effects such as pain. If the preparation comprising an anti-GD2 antibody is administered in a dose as low as possible but sufficient to induce CDC and/or whole blood cytolysis, and is administered in said cytolysis threshold dose for a treatment period until the predetermined overall patient dose has been administered, pain can be substantially reduced and thus, the administration of morphine or other analgesics can be substantially reduced or even stopped.

In this first aspect, the invention concerns a method for treating a GD2 positive cancer by administering a preparation comprising an anti-GD2 antibody to a patient as a continuous intravenous infusion over 24 hours per day. The preparation comprising an anti-GD2 antibody may be administered for a treatment period until the predetermined overall patient dose has been administered.

Furthermore, the invention concerns a method for treating a GD2 positive cancer by administering a preparation comprising an anti-GD2 antibody to a patient, wherein the preparation is administered in a dose sufficient to induce tumor cell lysis (cytolysis threshold dose), and wherein said cytolysis threshold dose is administered until the predetermined overall patient dose has been administered.

In a second aspect, it has surprisingly turned out that treatment with one or more cytokines in combination with an anti-GD2 antibody and a retinoid does not provide any clinical benefit over the treatment with the anti-GD2 antibody and a retinoid, but without any cytokine, especially without IL-2.

Thus, in this second aspect, the invention concerns a preparation comprising an anti-GD2 antibody (also referred to as antibody preparation) for use in the treatment of a GD2 positive cancer in a patient, wherein the preparation comprising an anti-GD2 antibody is administered to the patient without concomitantly administering IL-2, and wherein one or more treatment periods with the antibody is/are preceded, accompanied, and/or followed by one or more treatment periods with a retinoid. Furthermore, the present invention concerns a method for treating a GD2 positive cancer by administering a preparation comprising an anti-GD2 antibody to a patient, wherein the patient is not concomitantly treated with Interleukin-2 (IL-2), and wherein one or more treatment periods with the antibody is/are preceded, accompanied, and/or followed by one or more treatment periods with a retinoid.

The term "patient" as used herein shall mean an animal or human subject suffering from cancer, especially a GD2 positive cancer. In an embodiment, the patient is a human subject suffering from a GD2 positive cancer. The term "treatment" or "treating" as used herein shall mean that a drug or treatment is administered to patient in need thereof.

The terms "concomitantly treated with" or "concomitantly administering" as used herein shall mean that one treatment (e.g. with an anti-GD2 antibody and/or a preparation comprising an anti-GD2 antibody, referred to as antibody treatment) is preceded, accompanied, and/or followed by the other one or more treatments (such as e.g. treatment with one or more analgesics, and/or one or more other drugs or treatments), in particular within the same treatment cycle and/or within the same overall treatment time (e.g. in which the anti-GD2 antibody is administered). The treatment period of a concomitant treatment may or may not overlap with the other treatment period (e.g. the antibody treatment period), either partially or entirely. Accordingly, the treatment period of a concomitant treatment (e.g. the analgesic treatment) may precede, accompany, and/or follow the treatment period with the other treatment (e.g. the antibody treatment period). In one embodiment, the treatment periods of concomitant treatments are within the same treatment cycle.

Accordingly, the terms "not concomitantly treated with", "without concomitantly administering" or "not concomitantly administering" as used herein shall mean that one treatment is not preceded, accompanied, and/or followed by the one or more other treatments, respectively. In one embodiment, the above defined terms shall mean that a patient is not treated with said drug or treatment (i.e. that said drug or treatment is not administered to said patient) within the same treatment cycle and/or within the same overall treatment time. Accordingly, the treatment period of such a non-concomitant treatment (e.g. cytokine treatment) may not overlap with the other treatment period (e.g. the antibody treatment period), either partially or entirely. In an embodiment, the treatment period of a non-concomitant treatment may not precede, accompany, and/or or follow the treatment period with the other treatment (e.g. the antibody treatment period). In one embodiment, the treatment periods of non-concomitant treatments are not within the same treatment cycle. However, a patient who is not concomitantly treated with a drug or treatment (e.g. one or more cytokines) may have been treated with said drug or treatment (e.g. one or more cytokines) in previous treatment cycles and/or previous overall treatment times.

The term "cytokines" as used herein shall mean proteins, peptides, or glycoproteins which act as hormonal regulators or signaling molecules at nanomolar to picomolar concentrations and help in cell signaling. In an embodiment, the one or more cytokines are selected from immunomodulating agents, such as e.g. interleukins and/or interferons.

In an embodiment, the one or more cytokines are selected from the group consisting of IL-2, GM-CSF, Granulocyte colony-stimulating factor (G-CSF), IL-12, and/or IL-15. In one embodiment, the one or more cytokines are not fused to an antibody, in particular not to an anti-GD2 antibody.

The term "reduced dose" or "low-dose" as used herein refers to a dose of the respective drug that is significantly lower, e.g. at least 10%, 20%, 30%, 40%, 50%, 60%, 70%, 80%, 90%, or 100% (or any range in between these doses) lower than the usual dose of the same drug administered in the same or similar setting, i.e. in the same or similar patient groups with the same or similar treatment(s). The usual dose may be the dose that has frequently been used in the past and/or is mainly used in the same or similar setting, i.e. in the same or similar patient groups with the same or similar treatment(s). The dose may be reduced by reducing the daily dose, and/or by reducing the frequency and/or duration of administration. For example, for a 50% reduced dose, the respective drug may be administered in the same frequency or duration as usual, but with only half of the usual daily dose, or the respective drug may be given in the usual daily dose, but e.g. only on every second day, if it has usually been given every day. In another example, 50% of the usual daily dose may be given every second day instead of the usual daily administration, thus, resulting in a reduced dose that is 75% lower than the usual dose. Accordingly, a person skilled in the art can easily determine suitable doses and administration schedules according to the invention.

A "treatment period" with a specific preparation or treatment as used herein means the period of time in which said specific preparation or treatment is administered to the patient within one treatment cycle, e.g. the time period of subsequent treatment days. For example, if the preparation comprising a cytokine is usually administered for 5 consecutive days, followed by one or more days of no administration of the preparation comprising a cytokine, then the treatment period with the preparation comprising a cytokine comprises 5 days. In another example, if the preparation comprising the anti-GD2 antibody is administered continuously over 24 h for 10 consecutive days, followed by one or more days of no administration of the preparation comprising the anti-GD2 antibody, then the treatment period with the preparation comprising the anti-GD2 antibody comprises 10 days. In another example, if isotretinoin is administered twice a day for 14 days, followed by one or more days of no isotretinoin administration, then the treatment period with isotretinoin comprises 14 days.

Figure 8:
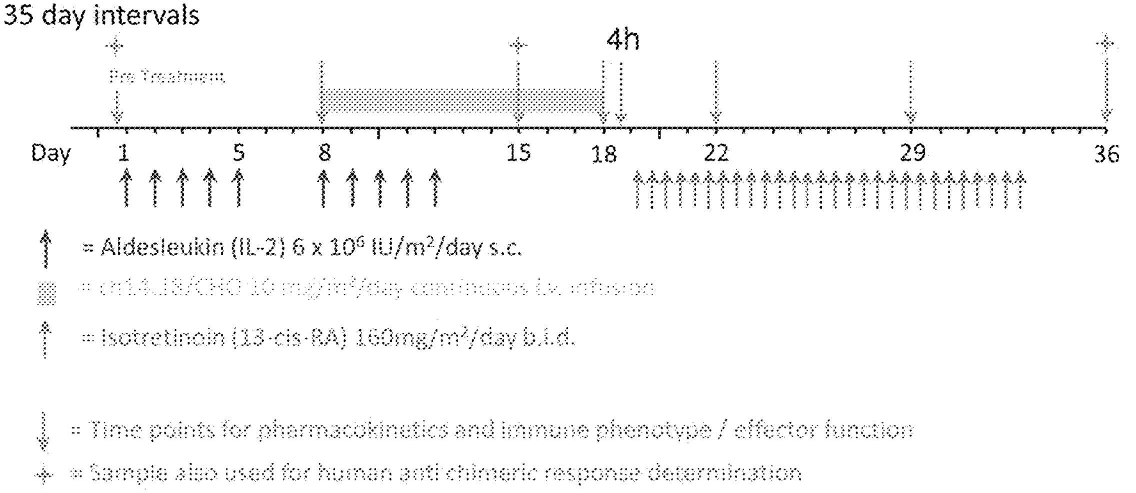
FIGS. 8 and 9 show examples of schematic treatment schedules for the treatment with a preparation comprising an anti-GD2 antibody combined with other treatments.
Figure 9:
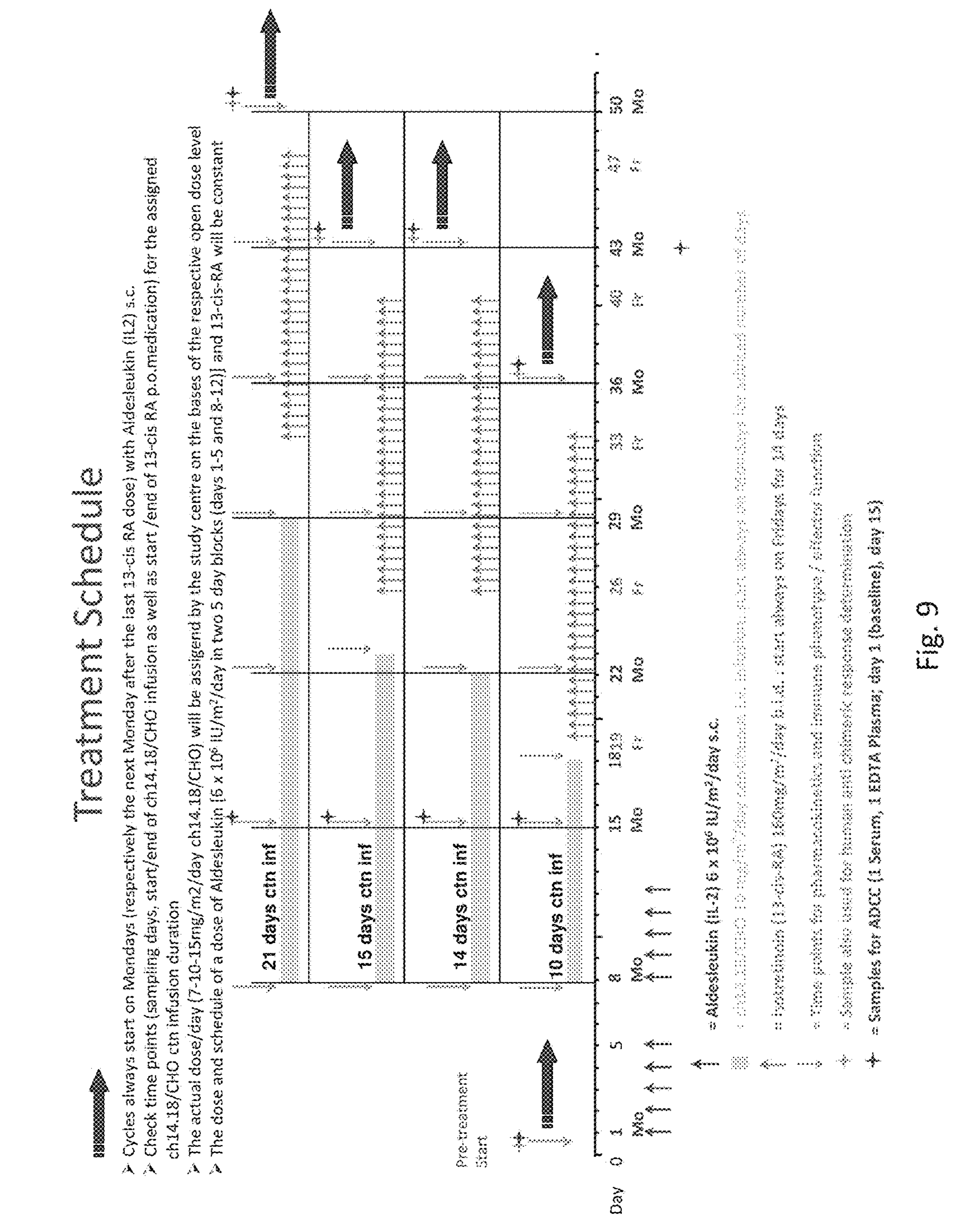

Any such treatment periods may be repeated, entirely or partially overlap with other treatment periods with other drugs or treatments, and/or may be preceded and/or followed by periods of no treatment. For example, a treatment cycle (e.g. as depicted in FIGS. 8 and 9) may comprise two 5-day treatment periods with IL-2, the second of which is overlapping with a 10-day (or 14-, 15-, or 21-day) treatment period with ch14.18 (APN311), followed by a 14-day treatment period with isotretinoin.

The terms "combined" or "combination" as used herein in relation to treatment periods shall mean that two or more treatment periods with the same and/or different drugs or treatments are comprised in one treatment cycle. Said two or more treatment periods with different drugs or treatments may partially or entirely overlap, or may not overlap. Any such treatment periods may be combined with (or separated by) one or more intervals of no treatment with the same and/or different drugs or treatments.

The term "treatment cycle" as used herein means a course of one or more treatments or treatment periods that is repeated on a regular schedule, optionally with periods of rest (no treatment) in between. For example, a treatment given for one week followed by three weeks of rest is one treatment cycle. In one embodiment, one treatment cycle comprises one treatment period with the preparation comprising an anti-GD2 antibody. The treatment cycle comprising one treatment period with the preparation comprising an anti-GD2 antibody may further comprise one or more treatment periods with one or more other drugs or treatments (for the second aspect of the invention except for cytokine treatment), such as e.g. retinoids, and/or analgesics. Any such treatment periods with one or more drugs or treatments within one treatment cycle may entirely and/or partially overlap. A treatment cycle may also comprise one or more time periods without any treatment. The periods of rest may e.g. be at least 1 day, or 2, 3, 4, 5, 6, 7, 8, 9, 10, 12, 13, or 14 days or more. Alternatively or in combination, the periods of rest may e.g. be at most 8 weeks, 7 weeks, 6 weeks, 5 weeks, 4 weeks, 3 weeks, 2 weeks, 1 week or less. Each treatment in a treatment cycle may preferably be a treatment according to the first, second, third or any combined aspect as defined in the brief description.

The term "overall treatment time" as used herein shall mean the continuous treatment period comprising one or more subsequent treatment cycles. A treatment cycle may be repeated, either identically or in an amended form, e.g. with a different dose or schedule, or with one or more different and/or additional treatments (e.g. with one or more other analgesics). The overall treatment time may comprise at least 1, or 2 or more cycles, e.g. up to 10 or up to 20 or even more treatment cycles. In one embodiment, the overall treatment time comprises 1, 2, 3, 4, 5, 6, 7, 8, 9, or 10 cycles. As described above, treatment cycles may comprise time periods of no treatment (intervals in which no treatment is administered to the patient, i.e. no antibody, no cytokine, and no other drug). Thus, as used herein, the overall treatment time may also comprise said intervals of no treatment within a treatment cycle and/or between treatment cycles. In one embodiment, a treatment cycle may directly follow after the previous treatment cycle, i.e. with no time period in between treatment cycles. However, the end of a treatment cycle may comprise a time period of no treatment, before the next treatment cycle begins. Example overall treatment times are e.g. at least 6 months, 8 months, 10 months, 12 months, 14 months, 16 months, 18 months, 20 months, 22 months, 24 months, 26 months, 30 months or more.

In some embodiments, the preparation comprising an anti-GD2 antibody is administered to a patient in a dose sufficient to induce tumor cell lysis (cytolysis threshold dose), and the preparation is administered as a continuous intravenous infusion over 24 hours per day. In other embodiments, the preparation comprising an anti-GD2 antibody is administered to a patient in a dose sufficient to induce tumor cell lysis (cytolysis threshold dose), and the preparation is administered as a continuous intravenous infusion over 24 hours per day, and said cytolysis threshold dose is administered until the predetermined overall patient dose has been administered.

Figure 2:
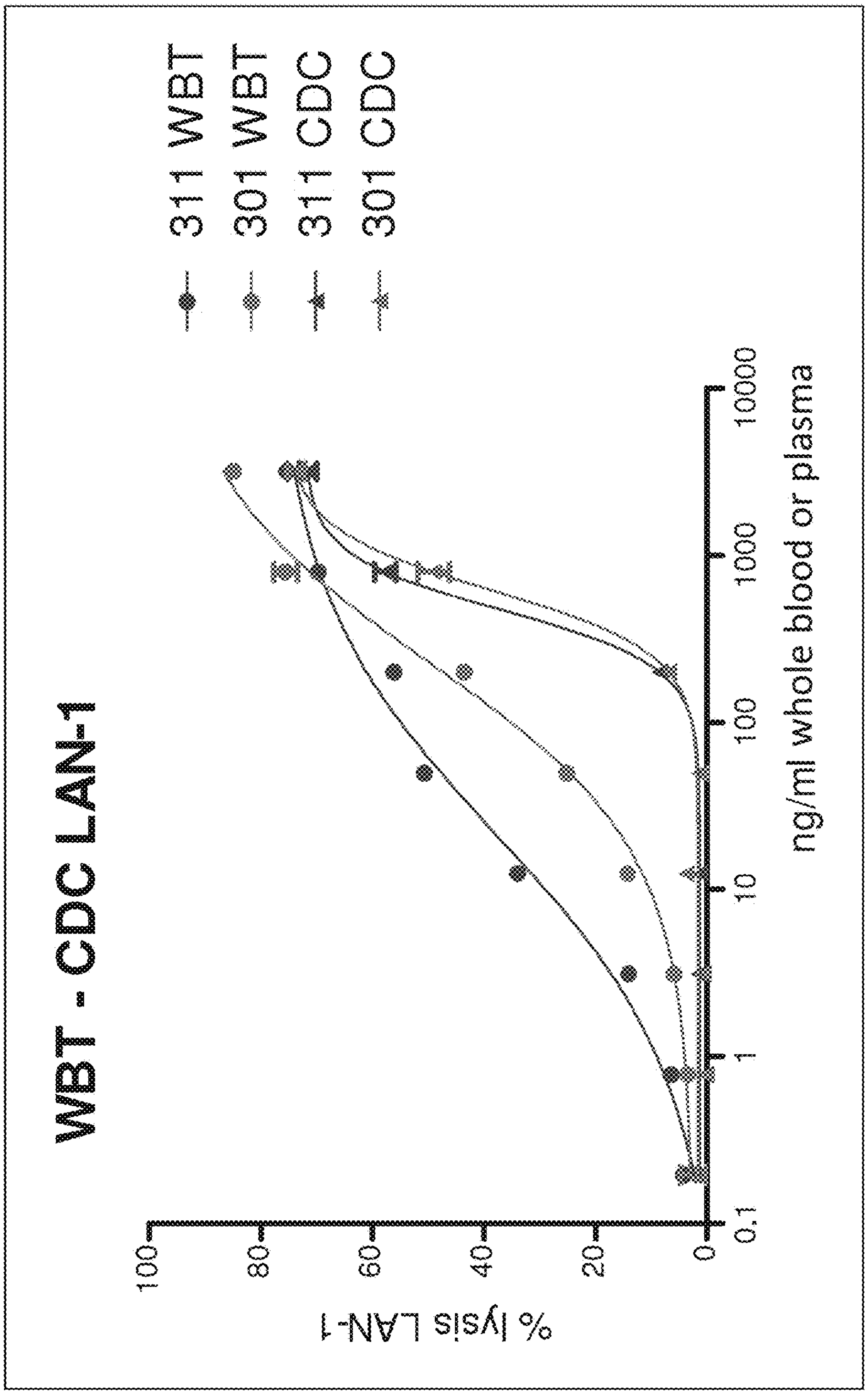
FIG. 2 shows the results of a WBT (with heparinized whole blood, using $^{51}$Cr labeled target human neuroblastoma cells) and a CDC assay (with heparinized plasma, using $^{51}$Cr labeled target human neuroblastoma cells) of one healthy donor in the presence of APN301 or APN311. There is a substantial difference in WBT lysis between the two preparations: 50% lysis is reached at an APN311 concentration of 21 ng/mL whole blood versus an APN301 concentration of 234 ng/mL. However, the difference in CDC is less substantial: 50% lysis is reached at an APN311 concentration of 470 ng/mL plasma versus an APN301 concentration of 619 ng/mL plasma.
Figure 3:
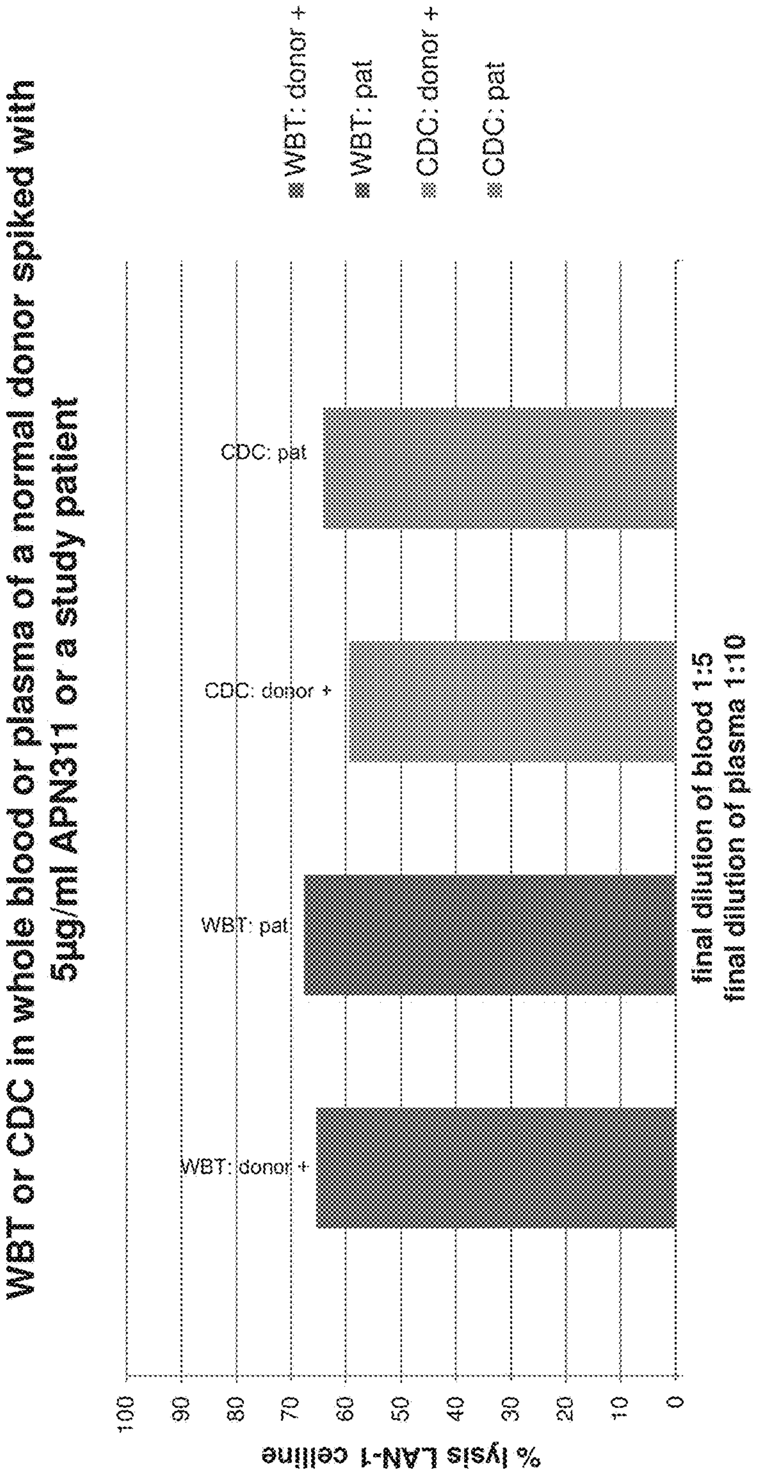
FIG. 3 shows the results of a WBT and CDC assay with whole blood or plasma of a healthy donor spiked with 5 μg/mL APN311 compared to the whole blood or plasma of a patient treated with APN311. The patient sample was collected on day 17 of the treatment cycle, i.e. at the end of the treatment period with APN311, which in this case is from day 8 to 18 of the treatment cycle.
Figure 4:
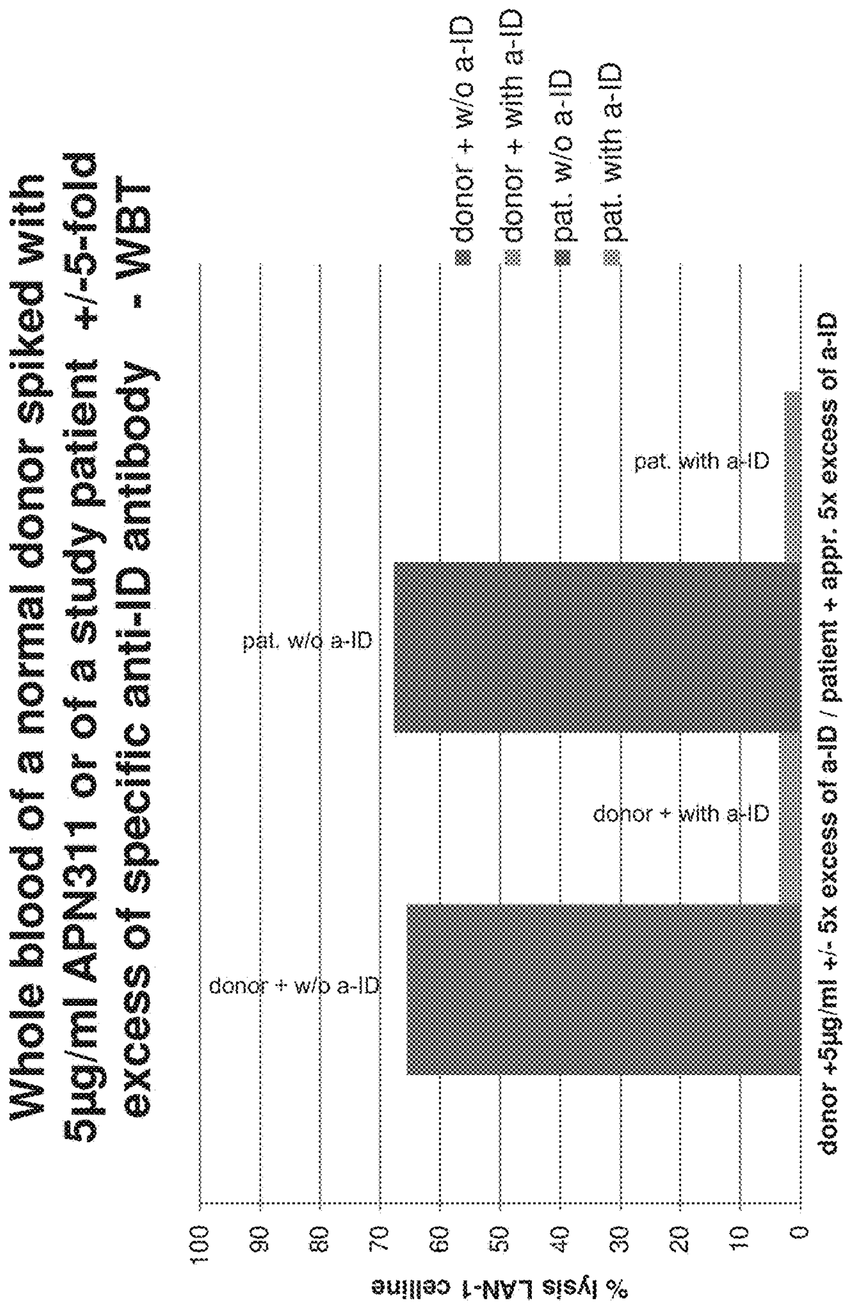
FIG. 4 shows the results of the WBT as shown in FIG. 3 compared to the same samples with the addition of a 5-fold excess of a specific anti-idiotypic (anti-ID) antibody, which inhibits the target cell lysis.
Figure 5:
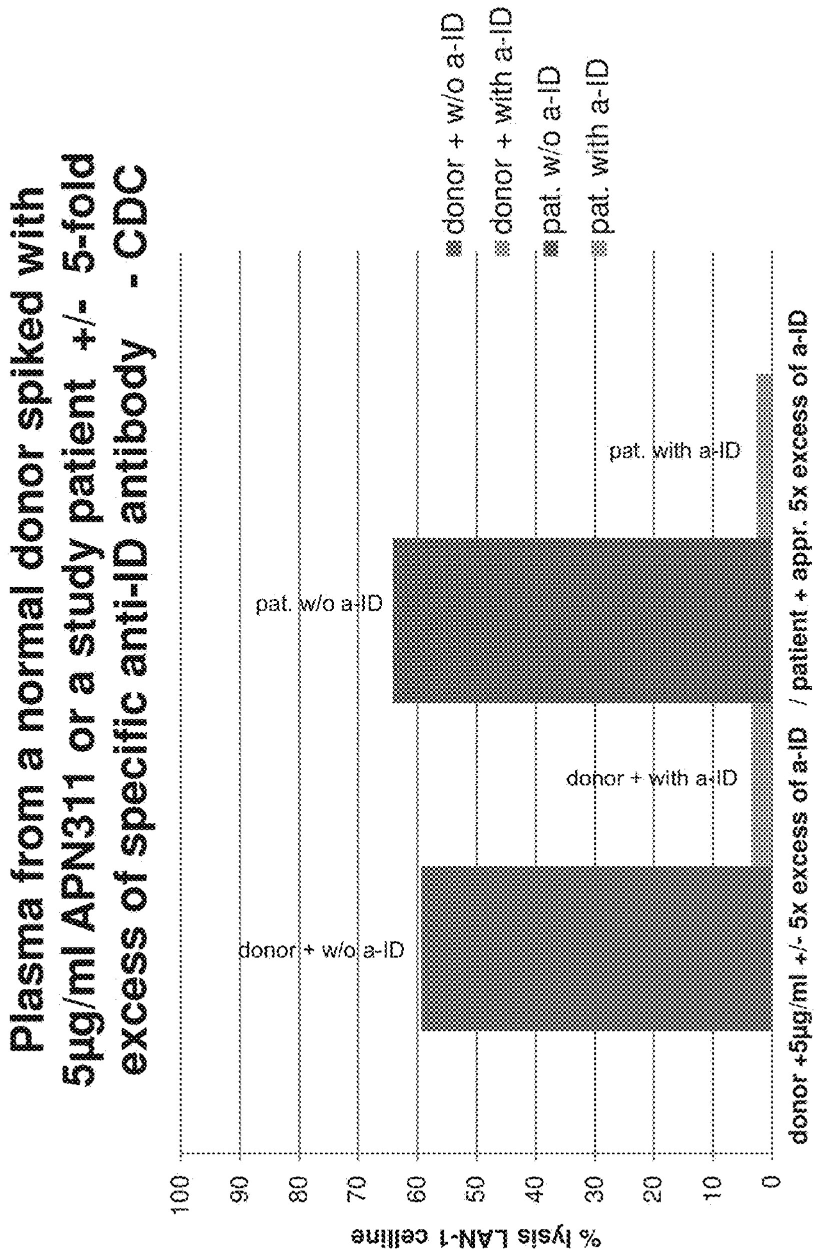
FIG. 5 shows the results of the CDC assay as shown in FIG. 3 compared to the same samples with the addition of a 5-fold excess of specific anti-ID antibody, which inhibits the target cell lysis.
Figure 7:
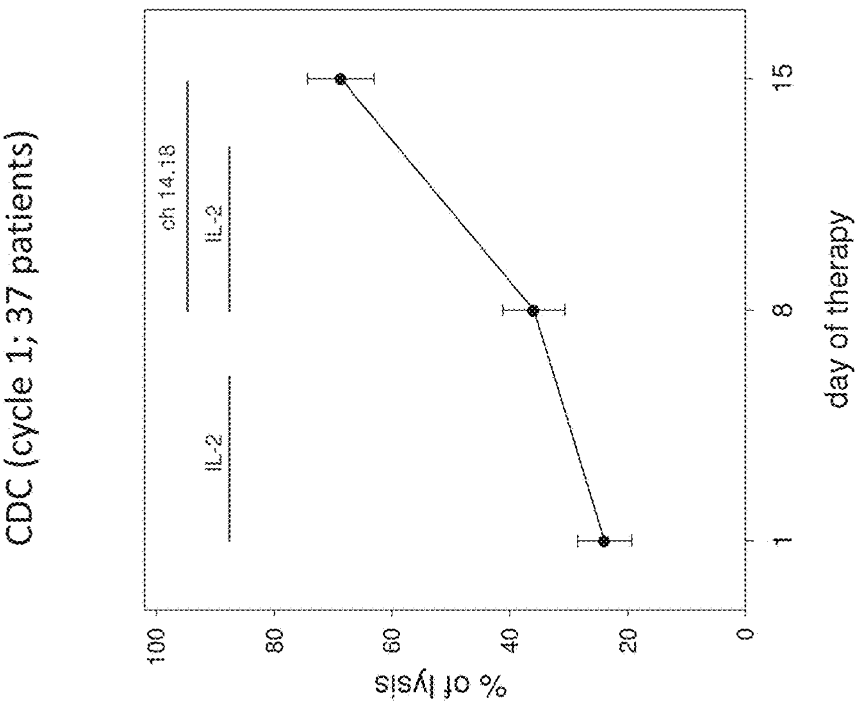
FIG. 7 shows the CDC assay results on day 1, 8, and 15 of the treatment cycle of 37 patients treated with APN311, as measured by a calcein release CDC assay. The treatment period with APN311 was from day 8 to 18, the two treatment periods with IL-2 were on days 1 to 5 and 8 to 12.

In certain embodiments, the cytolysis threshold dose is a therapeutically effective amount of the preparation comprising an anti-GD2 antibody. The therapeutically effective amount may be determined by a CDC assay or a WBT using patient's serum or plasma or heparinized whole blood. In some embodiments, the cytolysis threshold dose is a minimal cytolysis threshold dose, such as e.g. the lowest dose determined to induce a certain level of cytolysis in a CDC assay or a WBT. In one embodiment, the cytolysis threshold dose is the dose determined in a specific CDC assay or WBT to induce 30% of the maximal possible target cell lysis in that respective assay. In certain embodiments, the cytolysis threshold dose is the dose that achieves 35%, 40%, 45%, 50%, 55%, 60%, 65%, 70%, 75%, 80%, 85%, 90%, 95%, 100%, or any range in between these levels, of the maximal possible cell lysis in the respective assay (a specific CDC assay or WBT). For example, as done in Examples 2 and 3 and as shown in FIGS. 1, 2 and 7, several concentrations of the preparation comprising the anti-GD2 antibody are either spiked into the blood or plasma of the donor or already present in the blood or plasma of the patient who has been treated with the preparation comprising an anti-GD2 antibody, to determine a CDC or whole blood lysis curve. By drawing a curve between the measured concentrations of anti-GD2 antibody, the dose or concentration of anti-GD2 antibody achieving a certain threshold cytolysis (e.g. 50% of the maximal possible target cell lysis) can be determined. In the example of FIG. 1, a threshold of 50% cytolysis (e.g. 50% of the maximal possible target cell lysis) is achieved with concentrations of 2 or 10 ng/mL whole blood of the respective donor in the WBT, or with 1000 ng/mL serum or plasma in the CDC assay. In this example, the threshold cytolysis is 50%.

The terms "threshold cytolysis" and/or "level of cytolysis" as used herein means the level of target cell lysis in a specific CDC assay or WBT specified to determine the cytolysis threshold dose in serum, plasma or whole blood in said CDC assay or WBT.

In some embodiments, the threshold cytolysis is maintained even for one or more time periods within the overall treatment time, where the patient is not treated with the preparation comprising an anti-GD2 antibody, i.e. in the intervals between the treatment periods with the preparation comprising an anti-GD2 antibody (if any, i.e. if the patient is not treated continuously over the overall treatment time with the preparation comprising an anti-GD2 antibody). In certain embodiments, the level of cytolysis is maintained over the entire treatment cycle. In some embodiments, the level of cytolysis is maintained over the overall treatment time.

Figure 11:
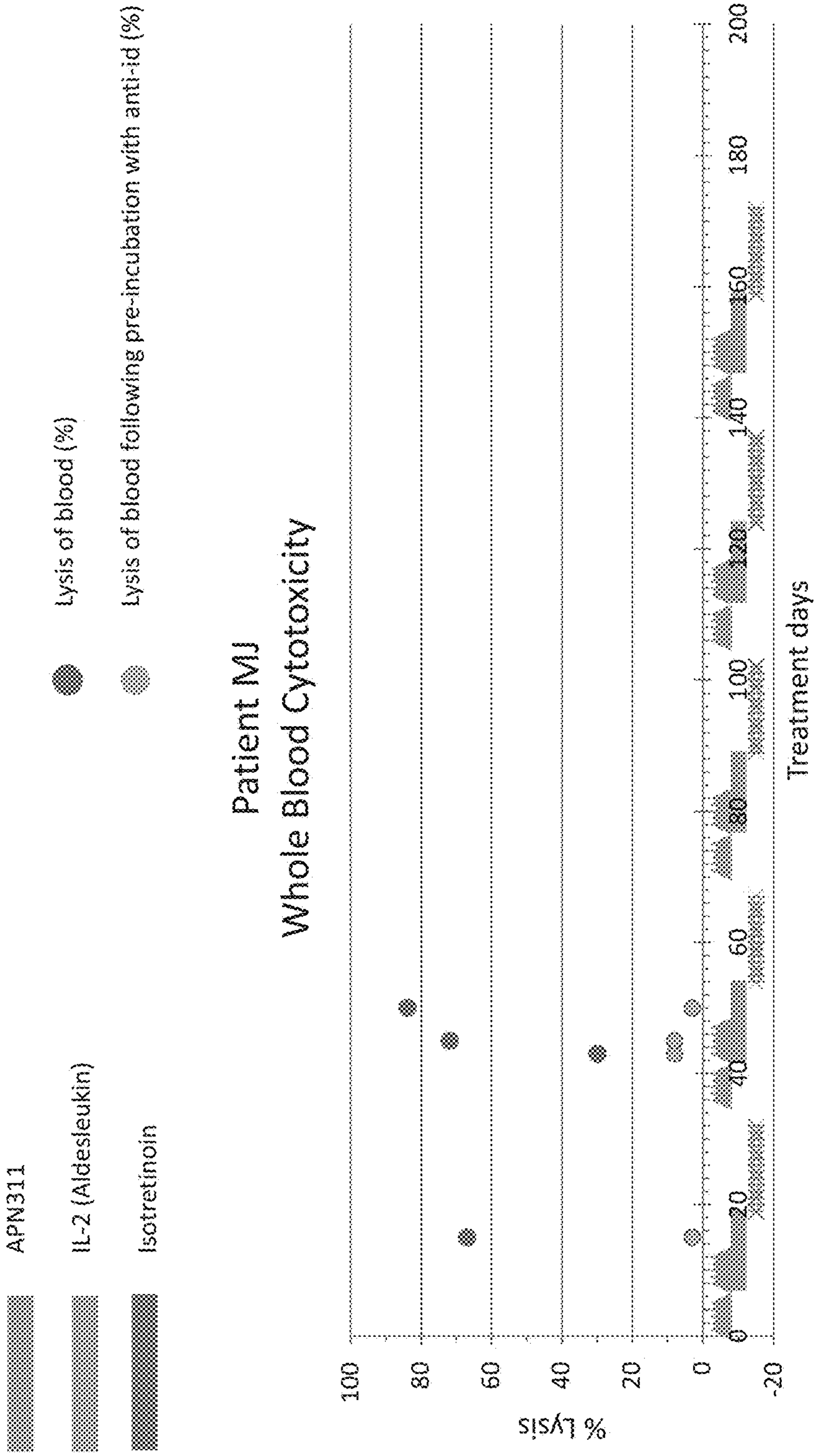
FIGS. 11 to 16 show cytolysis results obtained with blood samples from patients who are in different stages of their treatment cycles. The data are shown in a standardized format that represents the treatment schedule as applied, namely APN311 in a dose of 100 mg/m$^2$/cycle, 10 days continuous infusion by mini-pump, i.v.; aldesleukin (IL2) in a dose of 60×106 IU/m$^2$/cycle, 10 days per cycle, administered in two 5-day periods, in a dose of 6×106 IU/m$^2$/day s.c.; and 13-cis retinoid acid (isotretinoin) in a dose of 2240 mg/m$^2$/cycle, administered for 14 days (once a day) in a dose of 160 mg/m$^2$/day p.o. (per os, or oral administration). The overall treatment time comprises 5 cycles comprising 35 days per cycle, and day 36 is the first day of the second treatment cycle. The blood samples taken at the beginning (i.e. on the first day) of the treatment period with APN311 (corresponding to day 8 of the treatment cycle) were taken prior to the start of the APN311 treatment, see also table 8.
Figure 12:
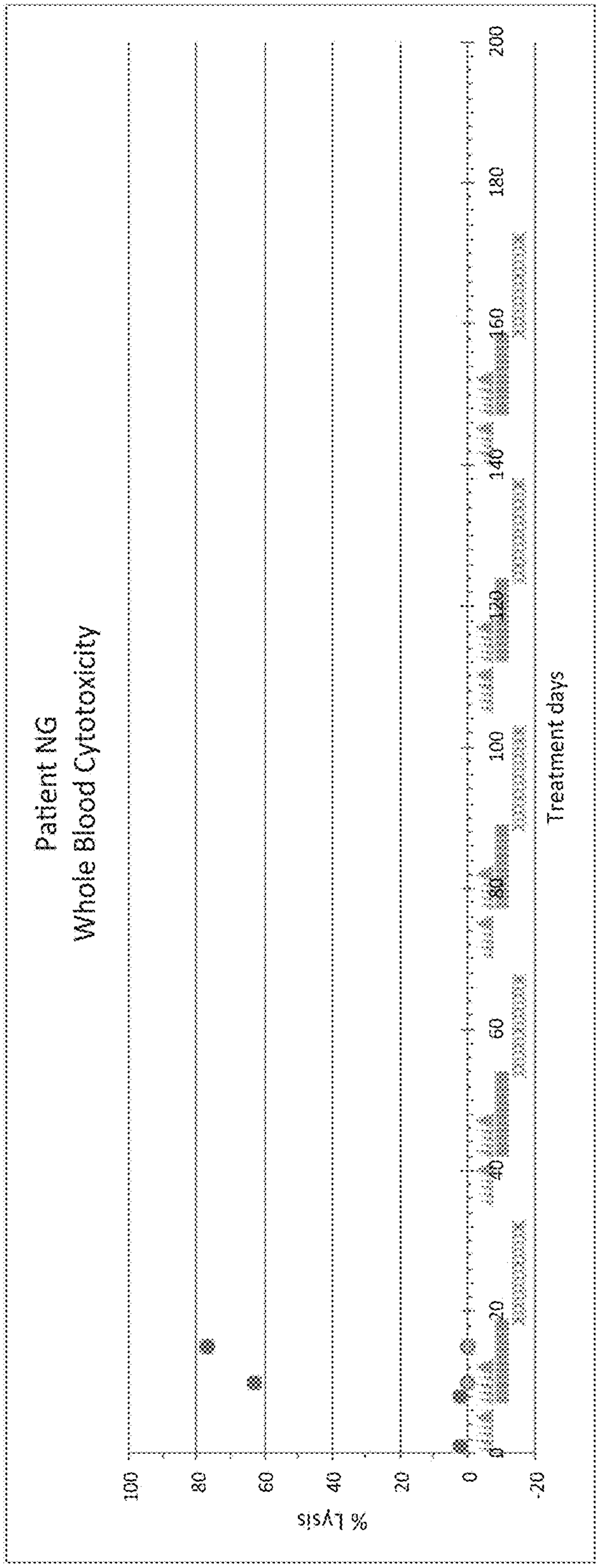
Figure 13:
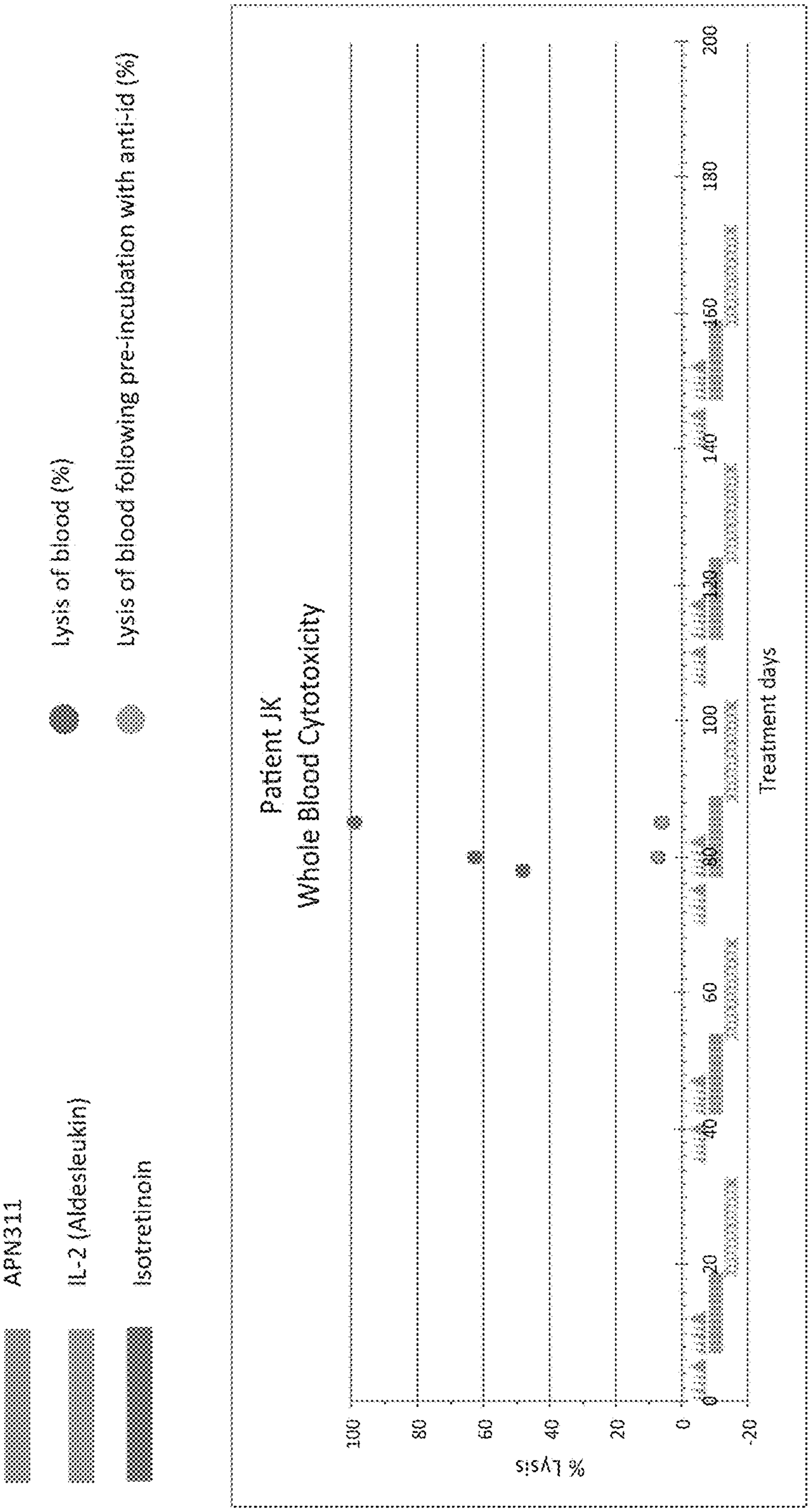
Figure 14:
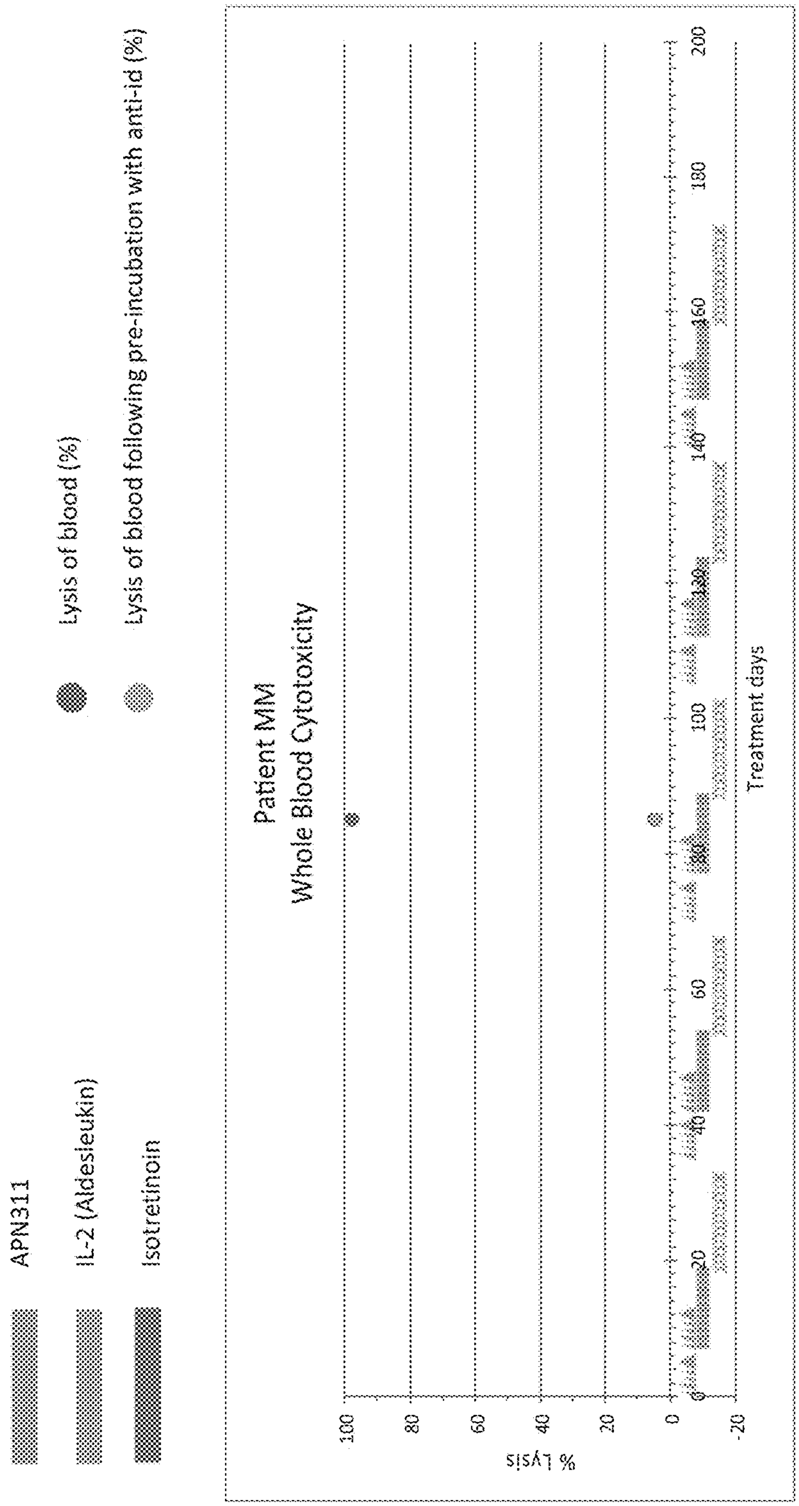
Figure 15:
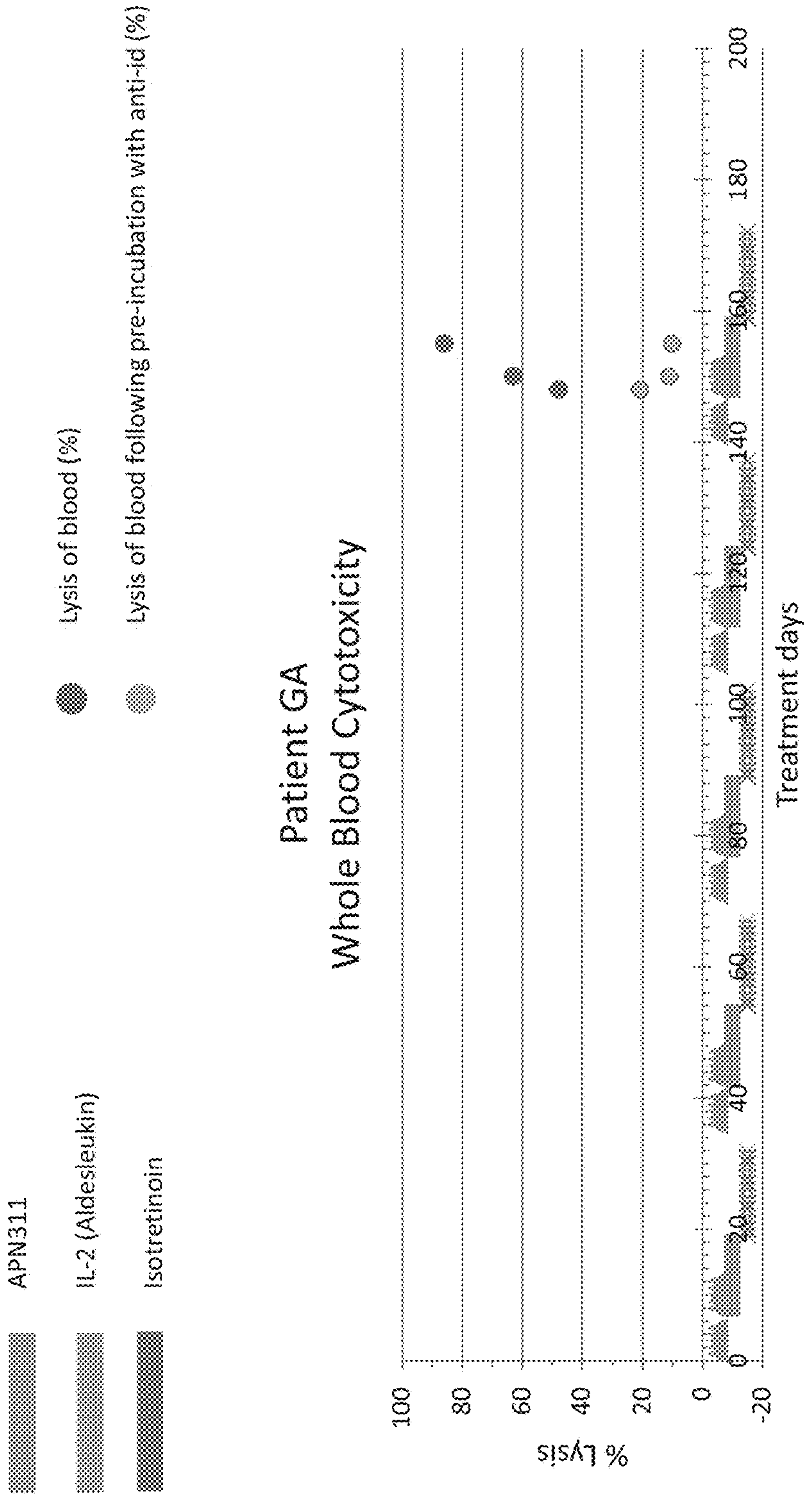
Figure 16:
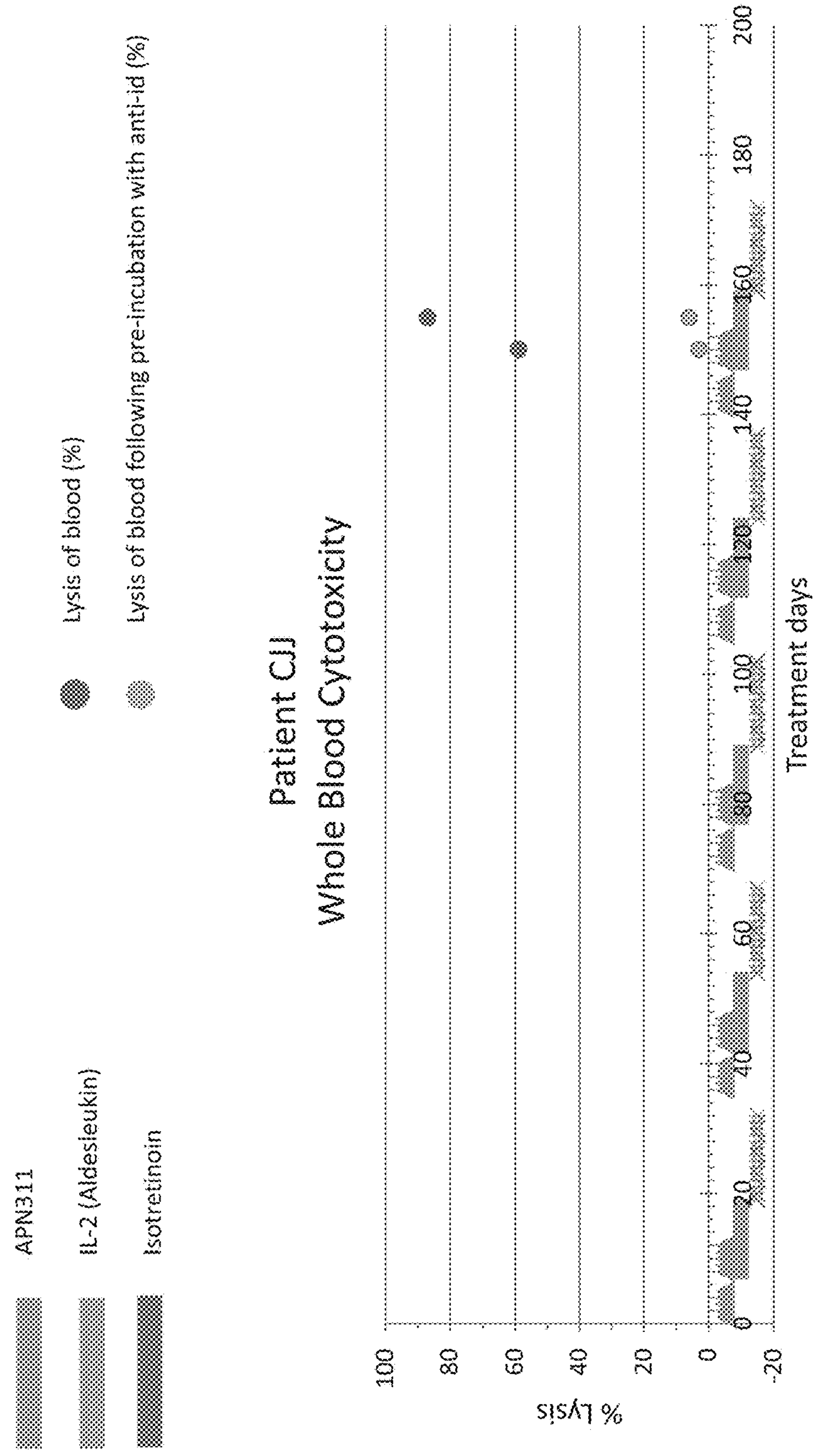

As can be seen in FIGS. 11, 13, and 15, an increased level of cytolysis between 30% and 50% has been maintained even over the interval, where the patients have not been treated with the preparation comprising an anti-GD2 antibody.

In one embodiment, the cytolysis threshold dose is determined individually for each patient.

The term "predetermined overall patient dose" as used herein shall mean the overall patient dose per treatment cycle, as further specified below.

If a range is given herein, any such range shall include any range in between the given ranges (i.e. the lower and the upper limit of the range). For example, if a range is given of e.g. 1 to 5 days, this shall include 1, 2, 3, 4, and 5 days. The same applies to any other ranges, including but not limited to other time periods (e.g. infusion time in hours), any dose ranges (e.g. per $m^2$ body surface area, per kg body weight, per day, per treatment cycle etc.), infusion rates, concentrations, percentages, factors, ratios, and numbers.

The cytolysis threshold dose may be determined by a complement dependent cytolysis (CDC) assay or a whole blood test (WBT). The WBT is an assay in which the target cells or target components (i.e. cells, liposomes or other cell-like compartments to be lysed) are contacted with appropriately anti-coagulated whole blood from the patient. The CDC assay can be, for example, a standard CDC assay as known in the art (e.g. as described in Indusogie et al., J Immunol 2000; Zeng et al., Molecular Immunology 2005; or in WO2005/070967). The CDC assay and/or the WBT may be done with GD2 positive target cells, such as tumor cell lines of the GD2 positive cancer to be treated. For example, if the patient to be treated suffers from neuroblastoma, the cell line may be a neuroblastoma cell line, such as e.g. LAN-1 human neuroblastoma cells. In another example, if the patient to be treated suffers from melanoma, the cell line may be a melanoma cell line, such as e.g. M21 human melanoma cells. In still another embodiment, the target cells of the CDC assay and/or the WBT are tumor cells obtained from the patient, i.e. autologous tumor cells of the patient. In another embodiment, the target component of the CDC assay and/or WBT is a liposome displaying GD2 on the surface. The target cells or target components are labeled with a signaling component, e.g. with a radioactive component, such as $^{51}$Cr, or with a fluorescent component, such as calcein. The signaling component is comprised by the target cell or target component, i.e. is inside of the target cell or target component (e.g. a liposome packed with the signaling component and displaying GD2 on the surface), and is released upon lysis of the target cell or target component. Thus, the signaling component provides the assay readout. The target cells or components loaded with the signaling compound are contacted with the whole blood, serum, or plasma in a certain ratio. The whole blood, plasma, or serum may be diluted for the CDC or WBT, e.g. in a ratio of 1:2 or higher, e.g. 1:4, 1:5, or 1:10, or any range in between these ratios prior to adding it to the sample. However, it may also be added to the sample un-diluted. The final concentration of the whole blood, plasma, or serum in the CDC or WBT sample may e.g. be in the range of 10 to 50%. Target cell or target component lysis can be measured by release of said signaling component by a scintillation counter or spectrophotometry. For example, the target cell or target component lysis can be measured by determining the amount of $^{51}$Cr released into the supernatant by a scintillation counter. The percentage of lysis may be determined by the following equation: 100×(experimental release−spontaneous release)/(maximum release−spontaneous release).

For the CDC assay, the cytolytic components (or effector components) are provided by serum or appropriately anti-coagulated plasma obtained from the patient or donor comprising the complement system components. For the WBT, the cytolytic components (or effector components) are provided by appropriately anti-coagulated whole blood obtained from the patient or donor comprising the complement system components as well as all cellular components, and also any further components comprised in whole blood which might be relevant to the target cell lysis, as well as the interplay of all components (e.g. complement activation is known to activate certain effector cells such as granulocytes). For the CDC and/or WBT, the serum, plasma, or whole blood may be added to the target cells or target components in different dilutions.

Furthermore, one or more samples of the CDC assay and/or WBT may be spiked with an anti-GD2 antibody in different dilutions, e.g. for generation of a standard curve.

In another embodiment, one or more anti-idiotypic (anti-id) anti-GD2 antibodies recognizing the variable domain of anti-GD2 antibodies may be added to a sample to inhibit the target cell lysis mediated by the antibody, e.g. as a negative control or to prove specificity of the assay and that the target cell lysis measured without the anti-id antibody is antibody-mediated or antibody dependent.

If the cytolysis threshold dose is determined for a patient before the start of the treatment with the preparation comprising an anti-GD2 antibody, the anti-GD2 antibody or the preparation comprising the anti-GD2 antibody is added in different dilutions to the CDC assay and/or WBT samples (in addition to the patient serum, plasma, or blood), so that the cytolysis threshold dose can be determined.

As further described herein, target cells for determination of the threshold dose may be human tumor cell lines of the same indication (e.g. human neuroblastoma cells in case of a neuroblastoma patient), or—if feasible—autologous tumor cells of the patient.

If the cytolysis threshold dose is determined for a patient during the treatment with the preparation comprising an anti-GD2 antibody, the serum, plasma, or whole blood of the patient (which comprises the anti-GD2 antibody) is added in different dilutions to the CDC assay and/or WBT samples (without the addition of separate anti-GD2 antibody), so that the cytolysis threshold dose can be determined.

The dose sufficient to induce CDC and/or whole blood cytolysis may be defined as the dose that achieves at least 20, 25, 30, 35, 40, 45, or 50%, or any range in between these levels of the maximal possible target cell lysis in that respective assay (a specific CDC assay or WBT). In one embodiment, the dose is defined as the dose that achieves at least 55%, at least 60%, at least 65%, at least 70%, at least 75%, at least 80%, at least 85%, at least 90%, at least 95%, or 100%, or any range in between these levels of maximal possible cell lysis in the respective assay (a specific CDC assay or WBT).

The cytolysis threshold dose determined in a specific CDC assay or WBT is a serum-, plasma-, and/or blood-level of anti-GD2 antibody. The dose of the preparation comprising the anti-GD2 antibody to be administered to patient to achieve such blood, plasma and/or serum antibody levels has then to be determined accordingly based on pharmacokinetic data for said preparation. As shown in FIGS. 1 and 2, antibody levels as low as 470 to 1000 ng/mL serum or plasma are sufficient to induce at least 50% tumor cell lysis in that CDC assay, e.g. 470 ng/mL (FIG. 2), or 1000 ng/mL (FIG. 1) of APN311, and 619 ng/mL of APN301 (FIG. 2). Accordingly, in one embodiment of the invention, the cytolysis threshold dose is 470 to 1000 ng/mL serum or plasma, or 470 to 10000 ng/mL serum or plasma, or any range in between these levels.

If a certain cytolysis threshold dose is determined in a CDC assay or a WBT, especially such assays in which target cells other than the patient's tumor cells are used, said cytolytic threshold determined in vitro (in vitro cytolytic threshold dose) may be increased by a certain margin of safety to ensure that the antibody dose is sufficient to induce cytolysis of the patient's tumor cells in vivo (in vivo cytolysis threshold dose). Accordingly, the in vitro cytolysis threshold dose may be increased by a factor of 1 to 10, or any range in between these factors.

In certain embodiments, the cytolysis threshold dose is 1410 to 3000 ng/mL or 2350 to 5000 ng/mL serum or plasma, or any range in between these levels.

The dose of the preparation comprising the anti-GD2 antibody to be administered to the patient is determined accordingly, i.e. it is administered in a dose to achieve said serum or plasma levels within the first 1-4 days of treatment with the preparation comprising the anti-GD2 antibody (e.g. on day 1, 2, 3, or 4 of the treatment period with the preparation comprising the anti-GD2 antibody), and said serum or plasma level is maintained over the entire treatment period with the preparation comprising the anti-GD2 antibody. As shown in FIGS. 1 and 2, antibody levels as low as 2 to 234 ng/mL in whole blood are sufficient to induce at least 50% tumor cell lysis in that WBT, e.g. 2 ng/mL (FIG. 1), or 10 ng/mL (FIG. 1), or 21 ng/mL (FIG. 2), of APN311, and 234 ng/mL of APN301 (FIG. 2). Accordingly, in one embodiment of the invention, the cytolysis threshold dose is 2 to 250 ng/mL whole blood, or 2 to 2500 ng/mL whole blood, or any range in between these levels. In certain embodiments, the cytolysis threshold dose is 2 to 100 ng/mL whole blood, or 5 to 200 ng/mL whole blood, or any range in between these levels. In some embodiments, the cytolysis threshold dose is 6 to 750, 6 to 7500, 10 to 1250, 10 to 12500, 6 to 300, 10 to 500, 15 to 600, or 25 to 1000 ng/mL whole blood.

Figure 6:
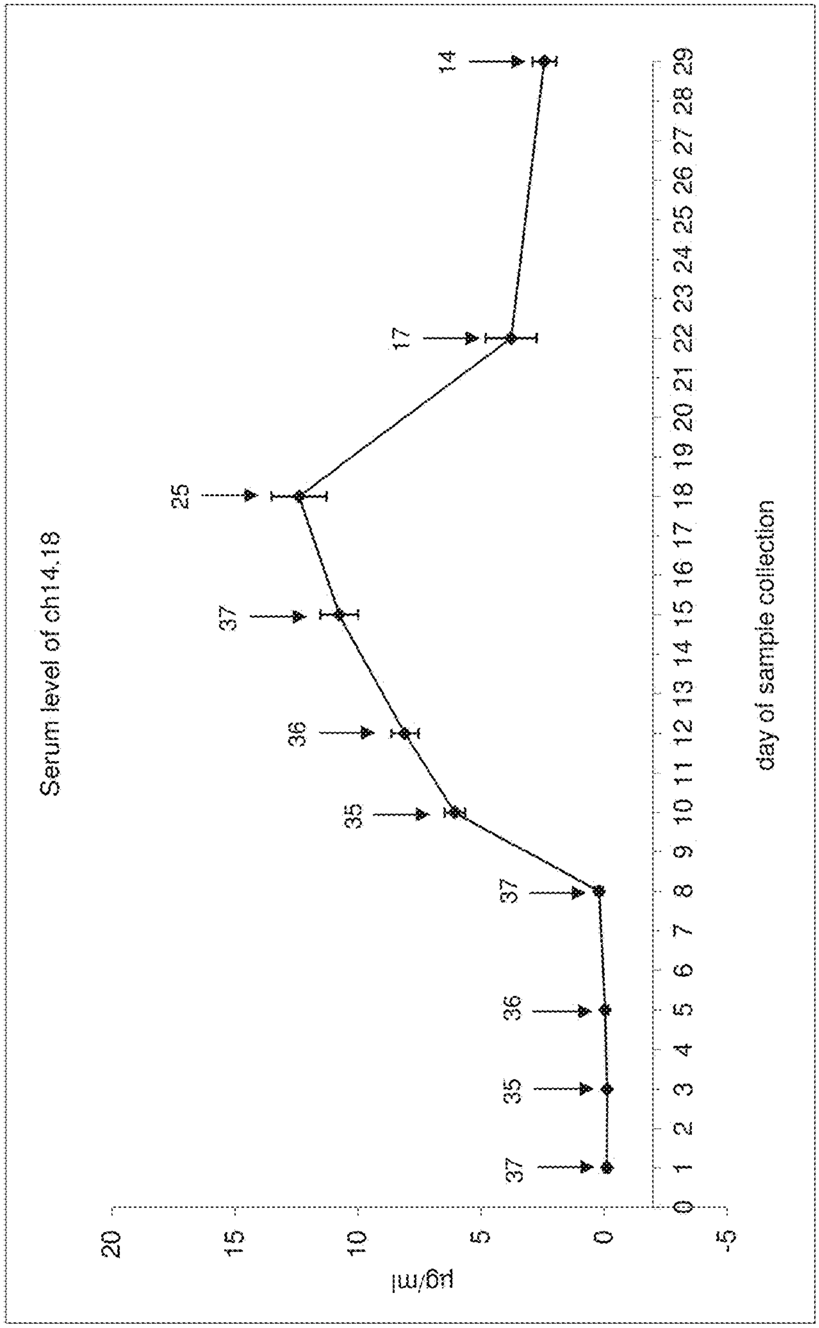
FIG. 6 shows the pharmacokinetics of APN311 in serum of patients. The numbers above the mean serum levels indicate the number of patients included in said mean at this day of sample collection. The treatment period with APN311 was from day 8 to 18, the two treatment periods with IL-2 were on days 1 to 5 and 8 to 12 of the treatment cycle.

The dose of the preparation comprising the anti-GD2 antibody to be administered to the patient is determined accordingly, i.e. it is administered in a dose to achieve said whole blood levels within the first 1-4 days of treatment with the preparation comprising the anti-GD2 antibody (e.g. on day 1, 2, 3, or 4 of the treatment period with the preparation comprising the anti-GD2 antibody), and said serum or plasma level is maintained over the entire treatment period with the preparation comprising the anti-GD2 antibody. As can be seen in FIG. 6, serum levels of 1000 ng/mL (or 1 μg/mL) can be achieved within the first one or two days of anti-GD2 antibody treatment, if the preparation comprising the anti-GD2 antibody is administered in a dose of 10 $mg/m^2$/day as a continuous intravenous (i.v.) infusion, i.e. for 24 h per day, using a mini-pump. Thus, in one embodiment, the preparation comprising the anti-GD2 antibody is administered in a dose of 5, 7, 10 or 15, especially 10 $mg/m^2$/day or any range in between these doses as a continuous intravenous infusion (24 h per day). In one embodiment, the cytolysis threshold dose is achieved within the first, second, third or fourth day of the treatment with the preparation comprising the anti-GD2 antibody. FIG. 7 shows that 50% of cytolysis can be achieved within the first three or four days of the treatment with the preparation comprising the anti-GD2 antibody, if the preparation comprising the anti-GD2 antibody is administered in a dose of 10 $mg/m^2$/day as a continuous intravenous (i.v.) infusion, i.e. for 24 h per day, using a mini-pump.

With the methods of the present invention it is possible to reduce the antibody dose to the minimum dose required for tumor cell lysis and/or target cell lysis as determined by a CDC assay or a WBT. In certain embodiments, the cytolysis threshold dose of the antibody determined by a CDC assay and/or a WBT is lower than 50, 40, 30, 25, 20, 15, 10, 7, 5 $mg/m^2$/day, or lower than any range in between these doses. Furthermore, the methods of the invention allow to individually determine the cytolysis threshold dose by a CDC assay and/or a WBT and thus, take into account the individual differences in the lytic capacity against tumor cells of the patients. Accordingly, each patient may receive his or her optimal antibody dose that is as low as possible to minimize potential side effect, especially pain, but is effective in tumor cell lysis.

The antibody preparation may be administered to a subject or patient in need thereof. In one embodiment, the subject or patient is a GD2 positive cancer patient. A GD2 positive cancer is a type of cancer, in which GD2 is expressed on tumor cells and comprises, for example, neuroblastoma, glioblastoma, medulloblastoma, astrocytoma, melanoma, small-cell lung cancer, desmoplastic small round cell tumor, osteosarcoma, rhabdomyosarcoma, and other soft tissue sarcomas. In an embodiment, the patient has been diagnosed with neuroblastoma, in particular high risk neuroblastoma. In one embodiment, the patient has been diagnosed with stage 4 neuroblastoma (according to the International Neuroblastoma Staging System (INSS)). In an embodiment, the patient has been diagnosed with minimal residual disease. In an embodiment, the patient has been diagnosed as a complete responder, i.e. as a patient showing a complete response to treatment. In another embodiment, the patient has been diagnosed with relapsed or refractory disease. In one embodiment, the patient suffers from primary refractory or relapsed high risk-neuroblastoma, or from minimal residual disease in high-risk neuroblastoma. The patient may have previously been treated or may be simultaneously treated with one or more other therapies, such as e.g. surgery, chemotherapy, radiation, myeloablative therapy, metaiodobenzylguanidine scintigraphy (mIBG), vaccine therapy, stem cell transplantation, cytokine treatment (e.g. with IL-2 and/or GM-CSF), and/or retinoid treatment (e.g. with isotretinoin).

In an embodiment, the patient is not enrolled in a clinical trial of phase I, II or III. In another embodiment, the patient is not enrolled in any clinical trial. In particular, the patient is not enrolled in any clinical trial in any country of the world. Accordingly, the patient is not participating in any systematic investigation and/or officially granted (e.g. by any competent national or regional health authority) tests in medical research and drug development that generate safety and efficacy data for any drug or treatment. In an embodiment, the patient is not participating in any systematic investigation and/or officially granted (e.g. by any competent national or regional health authority) testing for any health interventions (including diagnostics, devices, etc.). The former clinical trials described in the prior art with an anti-GD2 antibody without concomitant treatment with IL-2 and/or any other cytokine have been done to investigate general effects, adverse effects, and doses of the antibody as a basis for further investigation. However, the prior art clearly teaches to finally treat patients with an anti-GD2 antibody in combination with at least one cytokine, especially IL-2. Accordingly, any currently used treatment regimes with an anti-GD2 antibody comprise at least one cytokine, in particular IL-2, also in combination with GM-CSF (see e.g. Yu et al., cited above).

The antibody can be selected from the group of recombinant or artificial, including single chain antibodies, mammalian antibodies, human or humanized antibodies. It may comprise or be selected from constant and/or variable portions of an antibody in particular selected from Fc, Fc-like, Fv, Fab, $F(ab)_2$, Fab', $F(ab')_2$, scFv, scfc, VHH. However, any such antibody fragment should comprise the Fc portion that is responsible for complement binding, and thus, can mediate the natural (or in vivo) effector functions. Preferably the antibody comprises a light and heavy chain of an antibody. The antibody may comprise one or two antigen binding regions, which may bind the same or different antigen, e.g. GD2, that may be bound specifically. The inventive antibodies can be directed—e.g. generated by immunization against—the antigens as defined above. The anti-GD2 antibody may be a humanized or chimeric GD2 antibody, e.g. a humanized or chimeric 14.18, 3F8 or 8B6 antibody, or a murine antibody with the same specificity, or an antigen-binding fragment of any of these which mediates the natural effector functions. In one embodiment, the antibody is not a 14G2a antibody. The anti-GD2 antibody may have one or more amino acid modifications, such as e.g. a modified Fc region. In one embodiment, the anti-GD2 antibody is hu14.18K322A. In another embodiment, the anti-GD2 antibody is a chimeric 14.18 antibody. In one embodiment, the anti-GD2 antibody has the light chain nucleotide sequence of SEQ ID NO:1 (see also Example 1) and the heavy chain nucleotide sequence of SEQ ID NO:2 (see also Example 1). In one embodiment, the anti-GD2 antibody has the light chain amino acid sequence of SEQ ID NO:3 (see also Example 1) and the heavy chain amino acid sequence of SEQ ID NO:4 (see also Example 1). The relative molecular mass of the antibody comprising of two light and two heavy chains may be approximately 150,000 Dalton. In one embodiment, the preparation comprising the anti-GD2 antibody is APN311. The anti-GD2 antibody may be expressed in CHO cells, in SP2/0 cells, or in other suitable cell lines, such as e.g. HEK-293, MRC-5, Vero, PerC6, or NS0. In one embodiment, the anti-GD2 antibody is a chimeric 14.18 antibody expressed in SP2/0 cells (ch14.18/SP2/0). In another embodiment, the anti-GD2 antibody is a chimeric 14.18 antibody expressed in CHO cells (ch14.18/CHO).

In certain embodiments of the first aspect, the anti-GD2 antibody may also be an immunocytokine comprising a fusion protein of an anti-GD2 antibody (or an antigen-binding fragment thereof which mediates the natural effector functions) and a cytokine. The antibody part of the immunocytokine may be a humanized or chimeric GD2 antibody, e.g. a humanized or chimeric 14.18, 3F8 or 8B6 antibody. The antibody part of the immunocytokine protein may have one or more amino acid modifications, such as e.g. a modified Fc region. In one embodiment, the antibody part of the immunocytokine is hu14.18K322A. In another embodiment, the antibody part of the immunocytokine is a humanized 14.18 antibody. The cytokine part of the anti-GD2 antibody-cytokine fusion protein may be, for example, IL-2 or Interleukin-12 (IL-12), or IL-15 or GM-CSF. The antibody and the cytokine are fused together and may comprise a linker sequence. In one embodiment, the immunocytokine has the light chain nucleotide sequence of SEQ ID NO:5 (see also Example 1) and the heavy chain nucleotide sequence of SEQ ID NO:6 (see also Example 1). In one embodiment, the immunocytokine has the light chain amino acid sequence of SEQ ID NO:7 (see also Example 1) and the heavy chain amino acid sequence of SEQ ID NO:8 (see also Example 1). In one embodiment, the immunocytokine is APN301. The immunocytokine may be expressed in NS0 cells, or in other suitable cell lines, such as e.g. CHO, HEK-293, MRC-5, Vero, or PerC6.

In certain embodiments, the anti-GD2 antibody is not fused to any other moiety. In certain embodiments, the anti-GD2 antibody is not an immunocytokine. In certain embodiments, the preparation comprising an anti-GD2 antibody does not comprise an immunocytokine. In certain embodiments, the patient is not concomitantly treated with an immunocytokine, in particular not within the same treatment cycle and/or within the same overall treatment time comprising the antibody treatment.

The preparation comprising an anti-GD2 antibody may further comprise salts and WFI, and optionally amino acids, in particular basic amino acids, such as e.g. histidine, arginine and/or lysine. In one embodiment, the preparation comprising an anti-GD2 antibody may further comprise a buffer, e.g. phosphate buffered saline, comprising said salts and WFI.

The preparation comprising an anti-GD2 antibody may further comprise stabilizing agents, preservatives and other carriers or excipients. The preparation comprising an anti-GD2 antibody may be freeze-dried. In one embodiment according to the first aspect of the invention, the preparation comprising an anti-GD2 antibody comprises an anti-GD2 antibody-cytokine fusion (e.g. hu14.18-IL-2) and further comprises sucrose, L-arginine, citric acid monohydrate, polysorbate 20, and hydrochloric acid. In an embodiment, the preparation comprising an anti-GD2 antibody is APN301, the anti-GD2 antibody is hu14.18-IL-2 and the preparation comprises 4 mg/mL immunocytokine, 20 mg/mL sucrose, 13.9 mg/mL L-arginine, 2 mg/mL polysorbate 20, and 2.1 mg/mL citric acid monohydrate. In an embodiment, said preparation comprising an immunocytokine and other excipients is freeze-dried, can be reconstituted in 4 mL of 0.9% sodium chloride, and the resulting solution has a pH of 5.5 (pH can be adjusted with hydrochloric acid (HCL)). In an embodiment, the preparation comprising an anti-GD2 antibody is APN311, the anti-GD2 antibody is ch14.18/CHO and the preparation further comprises sucrose, polysorbate 20, histidine, and hydrochloric acid. In an embodiment, the antibody is ch14.18/CHO, the preparation comprising the antibody is APN311 (in an amended formulation), and said preparation comprises 4.5 mg/mL antibody, 50 mg/mL sucrose, 0.1 mg/mL polysorbate 20, and 3.1 mg/mL histidine. The preparation comprising an anti-GD2 antibody may be freeze-dried. The reconstituted solution may have a pH of 6±0.5. In one embodiment, the preparation comprising an anti-GD2 antibody does not comprise stabilising agents, preservatives and other excipients. The preparation comprising an anti-GD2 antibody may be added to an infusion bag, e.g. an infusion bag containing normal saline, i.e. a physiologic NaCl solution (0.9%), optionally with human serum albumin (HAS, also referred to as human albumin). In an example, the infusion bag comprises normal saline and 0.25-5% human serum albumin, or any range in between these concentrations. In an example, the infusion bag comprises a final volume of 250 ml NaCl 0.9% and 5 ml human albumin 20%, or 100 ml NaCl 0.9% and 5 ml human albumin 20%, or 50 ml NaCl 0.9% and 2 ml human albumin 20%.

The anti-GD2 antibody or the preparation comprising an anti-GD2 antibody may be administered in daily antibody doses of 1 to 30 mg/m$^2$, 1 to 35 mg/m$^2$, 1 to 50 mg/m$^2$, or 1 to 60 mg/m$^2$, e.g. 1, 2, 3, 4, 5, 6, 7, 7.5, 8, 9, 10, 12, 15, 20, 25, 30, 32, 35, 40, 45, 50, or 60 mg/m$^2$ or any range in between these periods. For example, a daily dose of 10 mg/m$^2$ means that the patient receives 10 mg anti-GD2 antibody per m$^2$ of body surface per day. As used herein, a dose (e.g. given in mg or microgram) refers to the dose of the active ingredient, i.e. to the amount of active ingredient in the preparation. For example, the given dose may refer to the amount of anti-GD2 antibody in the preparation comprising an anti-GD2 antibody, or the immunocytokine in the preparation comprising the immunocytokine, or the cytokine in the preparation comprising the cytokine, or the morphine or other analgesic in the preparation comprising morphine or other analgesics etc. As specified in the example above, a daily dose of 10 mg/m$^2$ means that the patient receives 10 mg anti-GD2 antibody (optionally contained in a certain volume of the preparation comprising the anti-GD2 antibody) per m$^2$ of body surface per day. As used herein, a dose given per m$^2$ means per m$^2$ of body surface area (BSA) of the patient. As used herein, a dose given per kg means per kg of body weight of the patient.

In some embodiments, the preparation comprising an anti-GD2 antibody is administered in daily doses of 1 to 15, 1 to 20, 1 to 25, 1 to 30, or 1 to 35 mg/m$^2$, or any range in between these daily doses. In certain embodiments, the preparation comprising an anti-GD2 antibody is administered in daily doses of less than 50, 40, 30 or 25 mg/m$^2$. In certain embodiments, the preparation comprising an anti-GD2 antibody is administered in daily doses of up to 7, 10, 15, or 20 mg/m$^2$. In one embodiment, the antibody preparation is administered in a dose of 25 mg/m$^2$/day for 4 days. In one embodiment, the antibody preparation is administered in a dose of 50 mg/m$^2$/day for 4 days. The anti-GD2 antibody may be administered in a dose of 10, 20, 25, 50, 60, 75, 80, 100, 120, 150, 200, 210, 250, or 300 mg/m$^2$/cycle or any range in between these doses. The total dose per patient per treatment cycle may be defined as the predetermined overall patient dose.

In some embodiments, especially in embodiments of the second aspect of the invention, the preparation comprising an anti-GD2 antibody is administered as an intravenous infusion over 5 h or more per day, e.g. 5.75 h or more per day, 8 h or more per day, 10 h or more per day, or up to 20 h per day, or any range in between these time periods, e.g. for 4 or 5 days or more. In other embodiments, the preparation comprising an anti-GD2 antibody is administered as a continuous intravenous infusion over 24 h per day, e.g. for 10, 14, 15, or for up to 21 or more days.

In some embodiments, the preparation comprising an anti-GD2 antibody is administered for a treatment period until a certain therapeutic effect has been reached. In some embodiments, the therapeutic effect may be an increase in immune response to the tumor, as determined, for example, by an increase in immune system biomarkers (e.g. blood parameters, such as lymphocyte counts and/or NK cell numbers; and/or cytokines). In some embodiments, the therapeutic effect may be a reduction in tumor markers (e.g. catecholamines). In some embodiments, the therapeutic effect may be determined by methods such as metaiodobenzylguanidine scintigraphy (mIBG), magnetic resonance imaging (MRI) or X-ray computed tomography (CT), and/or bone marrow histology (assessed by aspirate or trephine biopsy), and/or CDC assays and/or WBTs.

In certain embodiments, the therapeutic effect may be defined as stable disease (i.e. no further increase in lesions, tumor tissue and/or size), partial response (i.e. reduction in lesions, tumor tissue and/or size), and/or complete response (i.e. complete remission of all lesions and tumor tissue.

Complete Response (CR) may be further defined as follows:

- Complete disappearance of all measurable and evaluable disease;
- no new lesions;
- no disease-related symptoms; and/or
- no evidence of evaluable disease, including e.g. normalization of markers and/or other abnormal lab values.

In some embodiments, all measurable, evaluable, and non-evaluable lesions and sites must be assessed using the same technique as baseline.

Partial Response (PR) may be further defined as follows:

Applies only to patients with at least one measurable lesion;

Greater than or equal to 50% decrease under baseline in the sum of products of perpendicular diameters of all measurable lesions;

No progression of evaluable disease;

No new lesions.

In some embodiments, all measurable and evaluable lesions and sites must be assessed using the same techniques as baseline.

The preparation comprising an anti-GD2 antibody may be administered as described in WO2013/189516 or WO2013/189554. For example, the preparation comprising an anti-GD2 antibody may be administered as continuous intravenous infusion for 24 hours per day. Accordingly, in an embodiment the invention relates to a preparation comprising an anti-GD2 antibody for use in the treatment of a GD2 positive cancer in a patient, wherein the preparation comprising an anti-GD2 antibody is administered to the patient as a continuous infusion for one or more days and for two or more treatment cycles, without concomitantly administering IL-2. In another embodiment, the invention relates to a preparation comprising an anti-GD2 antibody for use in the treatment of a GD2 positive cancer in a patient, wherein the preparation comprising an anti-GD2 antibody is administered to the patient as a continuous infusion without concomitantly administering IL-2, and wherein the anti-GD2 antibody is not a 14G2a antibody.

The preparation comprising an anti-GD2 antibody may be administered for 4, 5, 10, 14, 15, or 21 consecutive days or any range in between these periods. The preparation comprising an anti-GD2 antibody may also be administered for 1, 2, 3, 4, 5, 6, 7, 8, 9, 10, 11, 12, 13, 14, 15, 16, 17, 18, 19, 20, 21, or more consecutive days. In certain embodiments, the preparation comprising an anti-GD2 antibody is administered over the entire treatment cycle, e.g. for 35 days. In some embodiments, the preparation comprising an anti-GD2 antibody is administered as a continuous intravenous infusion for the overall treatment time, e.g. over 5 treatment cycles with 35 days each, i.e. over 180 days in total. The daily antibody dose may be reduced accordingly, so that the predetermined patient dose of the antibody is administered. In one embodiment, the predetermined patient dose of the antibody is 100 $mg/m^2$/cycle. In one embodiment, the overall treatment time comprises 5 cycles. Accordingly, in this example, the antibody dose per overall treatment time is 500 $mg/m^2$. In an embodiment, this total antibody dose of 500 $mg/m^2$ per overall treatment time is administered over 180 days, i.e. in 2.77 $mg/m^2$/day. The preparation comprising an anti-GD2 antibody may be administered as a continuous intravenous infusion over a time period of 24 hours per day. For such continuous infusion, an osmotic mini-pump may be used. In one embodiment, the preparation comprising an anti-GD2 antibody is administered as continuous intravenous infusion for 24 hours per day for 4, 5, 10, 14, 15 or 21 consecutive days or any range in between these periods, in daily doses as specified above (e.g. 7, 10, 15, 20, or 25 $mg/m^2$/day), e.g. 25 $mg/m^2$/day for 4 days, 20 $mg/m^2$/day for 5 days, 10 $mg/m^2$/day for 10 days, 15 $mg/m^2$/day for 10 days, 7 $mg/m^2$/day for 14 days, 15 $mg/m^2$/day for 14 days, 10 $mg/m^2$/day for 15 days, 7 $mg/m^2$/day for 21 days, or 10 $mg/m^2$/day for 21 days or any range in between these doses. In certain embodiments, the preparation comprising an anti-GD2 antibody is not administered as continuous intravenous infusion for 5 days in a daily dose of 40 $mg/m^2$. In certain embodiments, the preparation comprising an anti-GD2 antibody is not administered as continuous intravenous infusion for 5 days, i.e. not as a 120-hour-infusion. In some embodiments, the preparation comprising an anti-GD2 antibody is administered as continuous intravenous infusion for more than 5 days. In some embodiments, the preparation comprising an anti-GD2 antibody is administered as continuous intravenous infusion for 6 or more days.

In one embodiment, the preparation comprising the anti-GD2 antibody is APN311 and is administered in a dose of 10 $mg/m^2$/day for 10 days. In one embodiment, the preparation comprising the anti-GD2 antibody is APN311 and is administered in a dose of 10 $mg/m^2$/day for 10 consecutive days for 1, 2, 3, 4, 5, or 6 or more treatment cycles.

According to the second aspect of the present invention, the patient is not concomitantly treated with IL-2, GM-CSF, and/or another cytokine. In an embodiment, the antibody treatment period is not preceded, accompanied, and/or followed by one or more treatment periods with IL-2, GM-CSF, and/or one or more other cytokines, i.e. the preparation comprising an anti-GD2 antibody is administered to the patient without concomitantly administering IL-2, GM-CSF, and/or one or more other cytokines. In one embodiment, the treatment period with the preparation comprising an anti-GD2 antibody is not accompanied by one or more treatment periods with a cytokine (or a preparation comprising one or more cytokines), in particular not within the same treatment cycle and/or within the same overall treatment time (comprising the antibody treatment). For example, the patient is not concomitantly treated with Granulocyte colony-stimulating factor (G-CSF), GM-CSF, IL-2, IL-12, and/or IL-15. In an embodiment, the preparation comprising an anti-GD2 antibody is administered to the patient without concomitantly administering IL-2. In an embodiment, the preparation comprising an anti-GD2 antibody is administered to the patient without concomitantly administering GM-CSF. In an embodiment, IL-2 and/or GM-CSF (or a preparation comprising IL-2 and/or GM-CSF) is not administered to the patient within the same treatment cycle that comprises the antibody treatment period(s). In an embodiment, the preparation comprising an anti-GD2 antibody is administered to the patient without concomitantly administering IL-2 and/or GM-CSF. In an embodiment, the preparation comprising an anti-GD2 antibody is administered to the patient without concomitantly administering a cytokine.

The treatment period with the preparation comprising an anti-GD2 antibody may be preceded, accompanied, and/or followed by one or more treatment periods with a retinoid (or a preparation comprising a retinoid). In an embodiment, the one or more treatment periods with the preparation comprising an anti-GD2 antibody is/are followed by one or more treatment periods with a retinoid. Said one or more treatment periods with a retinoid may follow within the same one or more treatment cycles comprising one or more antibody treatment periods, or thereafter, i.e. after the end of the one or more treatment cycles comprising the one or more antibody treatment period, in particular, after the end of the last treatment cycle comprising one or more antibody treatment periods, i.e. at the end of the overall treatment time with the antibody. Accordingly, in an embodiment, there is a time period in between the antibody treatment period and the retinoid treatment period, which may be a time period of no treatment, or may comprise one or more treatment periods with one or more other drugs or treatments. In one embodiment, the retinoid is a retinoic acid (RA), e.g. isotretinoin (cis-RA). The retinoid may be a first generation retinoid (e.g. retinol, retinal, tretinoin (retinoic acid, Retin-A), isotretinoin, and alitretinoin), a second generation retinoid (e.g. etretinate and its metabolite acitretin), and/or a third generation retinoid (e.g. tazarotene, bexarotene and Adapalene). The retinoid may also be a retinoid derivative, in particular a synthetic retinoid derivative, such as e.g. fenretinide. The preceding or following one or more treatment periods with a retinoid may be a treatment period without antibody and/or IL-2 (or other cytokine) administration.

In certain embodiments of the first aspect of the invention, the immunocytokine or the preparation comprising the immunocytokine may be administered in daily immunocytokine doses of 0.8 to 50 mg/$m^2$, e.g. 0.8, 1.6, 2, 3.2, 4, 4.8, 5, 6, 7, 7.5, 8, 9, 10, 12, 14.4, 15, 20, 25, 30, 32, 40, 45, or 50 mg/$m^2$ or any range in between these doses. For example, a daily dose of 10 mg/$m^2$ means that the patient receives 10 mg immunocytokine per $m^2$ of body surface per day. In one embodiment, one milligram of fusion protein contains approximately 0.8 mg of hu14.18 antibody and approximately $3\times10^6$ U of IL-2. The preparation comprising an immunocytokine may be administered subcutaneously or as intravenous infusion, e.g. once a day. The preparation comprising an immunocytokine may be administered i.v. over a time period of 24 hours per day. The preparation comprising an immunocytokine may be administered for 2, 3, 4, 5, 10, 14, 15, or 21 consecutive days or any range in between these periods. In another embodiment, the preparation comprising an immunocytokine is administered as continuous intravenous infusion for 24 hours per day for 10, 14, 15 or 21 consecutive days. For such continuous infusion, an osmotic mini-pump may be used. In one embodiment, the immunocytokine is administered in a dose of 12 mg/$m^2$/day for 3 consecutive days in 28-day cycles (in up to 10 cycles).

In the first aspect of the invention, the treatment period with the preparation comprising an anti-GD2 antibody may be preceded and/or accompanied by one or more treatment periods with a cytokine. In one embodiment, the cytokine is Granulocyte colony-stimulating factor (G-CSF), GM-CSF, IL-2, IL-12, and/or IL-15. The cytokine may be administered subcutaneously (e.g. once a day), or as intravenous infusion. In one embodiment, the cytokine is IL-2 and is administered subcutaneously once a day in a dose of $6\times10^6$ IU/$m^2$/day, e.g. on days 1 and 2 and on days 8 to 14 of the treatment cycle, or e.g. on days 1 to 5 and on days 8 to 12 of the treatment cycle. In one embodiment, the overall patient dose of IL-2 is $60\times10^6$ IU/$m^2$/cycle. In another embodiment, the cytokine is GM-CSF and is administered intravenously once a day over 2 hours in a dose of 250 micrograms/$m^2$/day, e.g. on days 1 and 2 and 8 to 14 of the treatment cycle.

As described herein, the treatment period with the preparation comprising an anti-GD2 antibody may be followed by one or more treatment periods with a retinoid. In one embodiment, the retinoid is a retinoic acid (RA), e.g. isotretinoin.

Any such treatment period may be repeated. Any such treatment period may be followed by an interval of no treatment, either with the same and/or with different drugs or treatments. In one embodiment, the interval may be an interval free of any treatment. In another embodiment, the interval is free of administration of the same preparation or treatment, however, other preparations or treatments may be administered during the interval.

Furthermore, the treatment according to the present invention may be preceded and/or accompanied by a treatment with one or more analgesics (or a preparation comprising one or more analgesics), such as e.g. non-steroidal anti-inflammatory drugs (NSAIDs, e.g. indometacin), and/or one or more opioids, and/or one or more other analgesics, or any combination thereof. In one embodiment, the analgesic is an opioid, e.g. morphine and/or morphine derivatives, such as e.g. hydromorphone. Other opioids are, for example, tramadol, pethidine, codeine, piritramide, levomethadone, as well as fentanyl, alfentanil, remifentanil and sufentanil.

As described above, an anti-GD2 antibody has usually been administered to a patient in combination with one or more cytokines (in the usual doses), especially IL-2 and/or GM-CSF. However, the combination of the antibody treatment with the usual cytokine treatment has potentiated side effects of the antibody treatment, in particular pain. Thus, the treatment with one or more analgesics, especially morphine, was required. It has now surprisingly turned out that anti-GD2 antibody treatment is efficient even without cytokine treatment. Accordingly, by the total omission of any cytokine treatment the pain side effect (and other side effects) can be significantly reduced and thus, the administration of morphine and/or other analgesics can be reduced as well.

The dose of analgesics can be further reduced by a long-term infusion of the anti-GD2 antibody, e.g. as continuous i.v. infusion over 24 h per day, as described in the first aspect of the invention and in WO2013/189516 or WO2013/189554. Thus, the analgesic dose can be substantially reduced in an inventive treatment schedule with no cytokine(s) together with a continuous infusion of the antibody.

With the preparations and methods of the invention, it is possible to reduce the dose, to change the route of administration (e.g. from intravenous infusion to oral), to reduce the duration of the analgesic treatment period(s), and/or to change the kind of preparation of the one or more analgesics. Thus, the present invention even allows for an outpatient management, at least for a part of the treatment cycle, of patients on treatment with a preparation comprising an anti-GD2 antibody.

The one or more analgesics may be administered orally. The one or more analgesics may also be administered as intravenous infusion, especially as continuous intravenous infusion for 24 hours per day. The treatment period with the one or more analgesics may precede and/or accompany the treatment period with the preparation comprising an anti-GD2 antibody.

In some embodiments, the one or more analgesics may be selected from GABA-analogues, such as e.g. gabapentin. Accordingly, the patient may be treated with gabapentin, e.g. three days prior to the start of the antibody treatment period.

The following doses and examples of analgesic treatment are usual doses that may be reduced as described herein. Usually, in this setting Gabapentin is administered orally in a dose of 10 mg/kg/dose once, twice or three times a day. Gabapentin may be given in a dose of up to 300 mg/kg/dose. Gabapentin is available and may be administered as oral solution containing 250 mg/5 mL of gabapentin, or in capsules (100 mg, 300 mg, and 400 mg). The gabapentin treatment may be administered instead of or in addition to the treatment with morphine and/or other analgesics. Furthermore, the patient may be treated with paracetamol (10 to 15 mg/kg/dose, every 4 hours or four times a day, orally or intravenously), ibuprofen (5 to 10 mg/kg/dose orally every 6 to 12 hours), metamizol (10 to 15 mg/kg/dose orally every 4 hours), diphenhydramine (0.5 to 1 mg/kg/dose orally or intravenously), and/or indometacin (e.g. 0.3 to 0.5 mg/kg/dose, or 25 or 50 mg/dose, orally or intravenously every 6 hours). Said treatment with paracetamol, ibuprofen, metamizol, and/or indometacin may be administered instead of or in addition to the treatment with morphine and/or gabapentin, and/or other analgesics.

In some embodiments, the daily dose of the one or more analgesics on one or more antibody treatment days according to the invention (continuous infusion) is lower than the usual daily dose administered during the treatment with a preparation comprising an anti-GD2 antibody that is administered as a non-continuous intravenous infusion, or that is administered as a continuous intravenous infusion for 5 days in a daily dose of 40 mg/$m^2$.

In certain embodiments, the dose (e.g. the daily dose) of the one or more analgesics (e.g. morphine) is reduced over time, e.g. within the overall treatment time, within a treatment cycle, during the antibody treatment period within a treatment cycle, from one antibody treatment day to the next antibody treatment day within a treatment cycle, and/or from one treatment cycle to the next. Examples of such morphine dose reductions are given in Table 9. For example, the morphine dose can be reduced by 10% from day 9 to 10 of the third treatment cycle, namely from 28% to 18% of the standard infusion rate (which in this example is 30 mcg/kg/h), or from 8.1 to 4.53 mg/kg/h, or from 0.19 to 0.11 mg/kg/day. In some embodiments, the morphine dose is continuously reduced within a treatment cycle, during the antibody treatment period within a treatment cycle, and/or from one antibody treatment day to the next antibody treatment day within a treatment cycle.

In some embodiments, morphine is used as analgesic, optionally in combination with one or more other analgesics.

For example, such usual morphine doses administered before and/or during a non-continuous infusion (or bolus infusion, i.e. an infusion for less than 24 hours a day) treatment period with a preparation comprising an anti-GD2 antibody are given in table 1. In this example of usual doses, the ch14.18/CHO (APN311) is given as an 8 hour infusion per day on 5 subsequent days in a dose of 20 mg/$m^2$/day and thus 100 mg/$m^2$/cycle, and IL-2 is given s.c. in 6 MIU/$m^2$/day for 5 consecutive days two times per cycle (i.e. 60 MIU/$m^2$/cycle), for 5 cycles, and morphine hydrochloride is given on each antibody treatment day (i.e. each day of a treatment cycle on which the preparation comprising an anti-GD2 antibody is administered to the patient) in a bolus dose of 0.05 mg/kg/h for 2 hours prior to starting the APN311 infusion, in an infusion rate of 0.03 mg/kg/h for 8 hours during the APN311 infusion, and in an interval infusion rate of 0.01 mg/kg/h for 14 hours on the first day of APN311 treatment, and for 4 hours on subsequent treatment days, if tolerated (with an interval of 10 hours with no morphine treatment). The dose was increased (e.g. increase in infusion rate during antibody infusion) and/or additional bolus doses were administered on an as needed basis. Accordingly, the prescribed morphine dose was at least 0.38 mg/kg per day, at least 2 mg/kg per treatment cycle (comprising 5 antibody treatment days), and at least 10 mg/kg per overall treatment time (comprising three cycles).

In certain embodiments, the one or more daily morphine doses and/or the one or more morphine infusion rates and/or the one or more percentages of the standard morphine doses are as specified in Table 9. For example, in one embodiment the percentage of the standard morphine dose administered on day 12 of the first treatment cycle is 41%, the morphine infusion rate on day 12 of the first treatment cycle is 12.26 mg/kg/h, and the daily morphine dose on day 12 of the first treatment cycle is 0.29 mg/kg.

TABLE 1

Morphine infusion schedule
Prepare 10 mg morphine in 40 mL glucose 5% (0.25 mg = 1 mL)

| | duration of morphine infusion (h) | morphine infusion rate (mg/kg/h) | morphine dose mg/kg |
|---|---|---|---|
| pre-infusion | 2 | 0.05 | 0.1 |
| infusion during APN311 treatment | 8 | 0.03 | 0.24 |
| interval infusion | 14 or 4 | 0.01 | 0.14 or 0.04 |
| total dose per treatment day (mg/kg/24 h) | | | 0.48 or 0.38 |

In another example of usual doses, APN311 is given as an 8 hour infusion per day on 5 subsequent days for 3 cycles in a dose of 10, 20, and 30 mg/$m^2$/day and 50, 100, 150 mg/$m^2$/cycle, and IL-2 is given s.c. in 6 MIU/$m^2$/day for 5 consecutive days two times per cycle (i.e. 60 MIU/$m^2$/cycle), and morphine hydrochloride is given on each antibody treatment day in a bolus dose of 0.5-1.0 mg/kg/dose (just prior to the start of infusion of the antibody), and in a rate of 0.05 mg/kg/hour continuous infusion during the APN311 infusion. The dose is increased (e.g. increase in infusion rate during antibody infusion) and/or additional bolus doses are administered on an as needed basis. Accordingly, the prescribed morphine dose (or usual morphine dose) is at least 0.9 mg/kg per day, at least 4.5 mg/kg per treatment cycle (comprising 5 antibody treatment days), and at least 13.5 mg/kg per overall treatment time (comprising three cycles).

In other examples of usual treatment with non-continuous (or bolus) infusions of ch14.18 and one or more cytokines, morphine has been administered in infusion rates up to 1.2 mg/kg/h over 24 hours.

In still another example of usual doses, ch14.18/Sp2/0 is given in a dose of 25 mg/$m^2$/day on four consecutive days. In one embodiment, Each dose of ch14.18/Sp2/0 is infused i.v. over 5.75 or more (maybe extended to up to 20 h), or 10 hours or more (maybe extended to up to 20 h), starting at 1.25 mg/$m^2$/h×0.5 h, then 2.5 mg/$m^2$/h×0.5 h, and optionally further increasing the infusion rate to then 3.75 mg/$m^2$/h×0.5 h, and then to 5 mg/$m^2$/h for the remaining dose, if tolerated. IL-2 is given every second cycle (e.g. cycle 2 and 4) as a continuous i.v. infusion over 4 days (96 h) in 3 MIU/$m^2$/day in week 1 of the treatment cycle and in 4.5 MIU/$m^2$/day in week 2 of the treatment cycle (i.e. 30 MIU/$m^2$/cycle). GM-CSF is given s.c. in a daily dose of 250 mcg/$m^2$. In an embodiment, each treatment cycle starts on day 0, and day 0 of a treatment cycle is the first day of treatment with the respective cytokine. The overall treatment time may comprise 1, 2, 3, 4, or 5 or more treatment cycles. Tables 2, 3, and 4 show examples of usual treatment schedules.

TABLE 2

Schema for the usual administration of 5 cycles of ch14.18/Sp2/0, cytokines, and isotretinoin (retinoic acid or RA).

| Cycle 1 | Cycle 2 | Cycle 3 | Cycle 4 | Cycle 5 |
|---|---|---|---|---|
| Ch14.18<br>GM-CSF | Ch14.18<br>Aldesleukin (IL-2) | Ch14.18<br>GM-CSF | Ch14.18<br>Aldesleukin (IL-2) | Ch14.18<br>GM-CSF |
| RA | RA | RA | RA | RA |

In said example of usual doses, Ch14.18/SP2/0 treatment is administered every 28 days at 25 mg/m$^2$/day×4 days for all 5 cycles; GM-CSF at 250 micrograms/m$^2$/day for 14 days; Aldesleukin (IL-2) at 3 MIU/m$^2$/day for first week, and at 4.5 MIU/m$^2$/day for second week.

TABLE 3

Treatment schema for cycles with GM-CSF

| | Day | | | | | | | | | | | | | | |
|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14-23 | 24 |
| GM-CSF | X | X | X | X | X | X | X | X | X | X | X | X | X | X | | Begin Cycle 2&4 |
| ch14.18 | | | | ⇧ | ⇧ | ⇧ | ⇧ | | | | | | | | | |
| RA | | | | | | | | | | | ⇧ | ⇧ | ⇧ | ⇧ | ⇧ | |

Note:
In variation to the treatment schema above, the RA treatment is started on day 11 of the first cycle, but according to the schema on day 10 of the third and fifth cycle. Accordingly, in variation to the treatment schema above, day 24 of the first treatment cycle is also the last day of RA treatment of the first cycle.

In said example of usual doses, GM-CSF is given at 250 micrograms/m$^2$/day as subcutaneous injection (strongly recommended) or i.v. as a 2 hour infusion daily from Day 0 through 13 (daily with the infusion of ch14.18/SP2/0 and for 3 days before and 7 days after the antibody treatment).

TABLE 4

Treatment schema for cycles with aldesleukin (IL-2)

| | Day | | | | | | | | | | | | | | |
|---|---|---|---|---|---|---|---|---|---|---|---|---|---|---|---|
| | 0 | 1 | 2 | 3 | 4-6 | 7 | 8 | 9 | 10 | 11-13 | 14 | 15 | 16 | 17 | 18-27 |
| IL-2 | X | X | X | X | | X | X | X | X | | | | | | |
| ch14.18 | | | | | | ⇧ | ⇧ | ⇧ | ⇧ | | | | | | |
| RA | | | | | | | | | | | ⇧ | ⇧ | ⇧ | ⇧ | ⇧ |

On days 28-31 of the aldesleukin cycles no treatment is administered. On day 32, the next treatment cycle (with GM-CSF) is started (day 32=day 0 of the following cycle).

As an example of usual doses, Aldesleukin (Interleukin-2, IL-2) may be given in a dose of 3 MIU/m$^2$/day by continuous infusion (using a CADD® Ambulatory Infusion Pump or a similar infusion pump) for 4 days (on Days 0-3) during the first week of each cycle. During the second week of each cycle, Aldesleukin (IL-2) may be given at 4.5 MIU/m$^2$/day for 4 days (on Days 7 to 10, with the infusion of ch14.18/SP2/0). Aldesleukin may be continuously infused i.v. over 96 hours through a catheter via an ambulatory infusion pump in 5% dextrose in water (may contain 0.1% human serum albumin if needed), total volume dependent upon the pump.

A sixth treatment cycle may be added with 14 days of no treatment (starting on day 24 of the fifth cycle, which is day 0 of the sixth cycle) followed by 14 days of the administration of isotretinoin only.

In an example of usual doses in this setting (i.e. with the treatments as described above), hydroxyzine (1 mg/kg; max dose 50 mg) or diphenhydramine (0.5-1.0 mg/kg; max dose 50 mg) are given i.v. over 10 minutes to start 20 minutes prior to ch14.18/SP2/0 infusion; acetaminophen (10 mg/kg; max dose 650 mg) p.o. is given 20 minutes prior to ch14.18/SP2/0 infusion; and/or a morphine sulfate loading dose of 50 mcg/kg is given immediately prior to ch14.18/SP2/0 administration and then continued with morphine sulfate drip with an infusion rate of 20-50 micrograms/kg/h to continue for two hours after completion of the ch14.18/SP2/0 infusion. Additionally, other narcotics such as hydromorphone or fentanyl may be used. Alternatively, lidocaine infusion may be used in conjunction with an i.v. bolus of morphine, if required. The usual administration guidelines for lidocaine infusion are shown below:

Administration of Lidocaine (in Usual Doses):

a. Give lidocaine i.v. bolus at 2 mg/kg in 50 cc normal saline (NS) over 30 min prior to the start of ch14.18/SP2/0 infusion.
b. At the beginning of ch14.18/SP2/0 infusion, start i.v. lidocaine infusion at 1 mg/kg/h and continue until two hours after the completion of ch14.18/SP2/0 infusion.
c. May give morphine i.v. bolus 25-50 microgram/kg every 2 h, if needed.

In said example of usual doses, one may also consider the administration of gabapentin with loading doses of morphine, and give morphine infusion/bolus as needed; may start with gabapentin 10 mg/kg/day and titrate up to 30-60 mg/kg/day depending on the clinical response.

In said example of usual doses, doses of hydroxyzine (or diphenhydramine) and acetaminophen can be repeated every 6 h, if needed; i.v. or p.o.

In said example of usual doses, additional morphine doses can be given during the ch14.18/SP2/0 infusion to treat neuropathic pain followed by an increase in the morphine sulfate infusion rate, but patients should be monitored closely. If patients cannot tolerate morphine (e.g., itching), fentanyl or hydromorphone can be substituted for morphine. Alternatively, lidocaine infusion may be used in conjunction with i.v. bolus of morphine, if needed.

The term “morphine dose” as used herein refers to the amount of morphine (in mg or mcg) per kg of body weight of the patient. Accordingly, if it is referred to a daily morphine dose, it is the amount of morphine (in mg or mcg) per kg of body weight of the patient per day, or if it is referred to a morphine dose per hour, it is the amount of morphine (in mg or mcg) per kg of body weight of the patient per hour (or morphine infusion rate), or if it is referred to a morphine dose per treatment cycle, it is the amount of morphine (in mg or mcg) per kg of body weight of the patient per treatment cycle, or if it is referred to a morphine dose per overall treatment time, it is the amount of morphine (in mg or mcg) per kg of body weight of the patient per overall treatment time.

In some embodiments, the morphine and/or other analgesics may be administered in a usual daily dose, but with a reduced frequency of administration, e.g. only every other day, if it has usually been administered each day. In another example, in which the morphine and/or other analgesics have usually been administered as continuous i.v. infusion over several days, either the infusion time per day may be reduced (resulting in a non-continuous infusion), or the total duration of the continuous infusion is reduced, i.e. the number of continuous infusion days.

In some embodiments, the daily dose of the one or more analgesics on one or more antibody treatment days (i.e. a day of a treatment cycle on which the preparation comprising an anti-GD2 antibody is administered to the patient) in a treatment cycle according to the invention (with no cytokine treatment and/or in a continuous antibody infusion schedule) is lower than the usual daily dose administered on one or more antibody treatment days in a usual treatment cycle (with usual cytokine treatment and/or in a non-continuous antibody infusion schedule). In some embodiments, the daily dose of the one or more analgesics on one or more analgesic treatment days (i.e. a day of a treatment cycle on which one or more analgesics, e.g. morphine, is administered to the patient, which may also be days prior to or after antibody administration) in a treatment cycle according to the invention (with no cytokine(s) treatment and/or in a continuous antibody infusion schedule) is lower than the usual daily dose administered on one or more analgesic treatment days in a usual treatment cycle (with usual cytokine treatment and/or in a non-continuous antibody infusion schedule).

In certain embodiments, the dose (e.g. the daily dose) of the one or more analgesics (e.g. morphine) is reduced over time, e.g. within the overall treatment time, within a treatment cycle, during the antibody treatment period within a treatment cycle, from one antibody or analgesic treatment day to the next antibody or analgesic treatment day within a treatment cycle, and/or from one treatment cycle to the next. In some embodiments, the analgesics dose, in particular the morphine dose, is continuously reduced within a treatment cycle, during the antibody treatment period within a treatment cycle, and/or from one antibody or analgesic/morphine treatment day to the next antibody or analgesic/morphine treatment day within a treatment cycle.

In some embodiments, the daily morphine dose administered during one or more days of administration of the antibody in a continuous antibody infusion schedule and/or an antibody administration schedule with no cytokine according to the invention, and/or the morphine dose of all antibody or morphine treatment days is lower than the daily morphine dose during administration of the antibody with the usual doses of one or more cytokines and/or in a non-continuous antibody administration schedule. In certain embodiments, the daily morphine dose (and/or the morphine dose per treatment cycle) administered in an antibody infusion schedule according to the invention (e.g. with no cytokine and/or as continuous antibody infusion) is 90% or less, 80% or less, 70% or less, 60% or less, or 50% or less, or 40% or less, or 30% or less, or 20% or less, or 10% or less of the morphine dose administered in or prescribed for a usual antibody infusion schedule (e.g. with usual cytokine doses and/or in a non-continuous antibody infusion). In some embodiments, the daily morphine dose administered during one or more days of continuous intravenous infusion of the antibody with no cytokine according to the invention and/or of all antibody or morphine treatment days is lower than 0.9, 0.72, 0.48, 0.38, 0.4375, and/or 0.205 mg/kg/day.

In some embodiments, the daily morphine dose administered during one or more days of continuous intravenous infusion of the antibody according to the invention and/or of all morphine treatment days is lower than the daily morphine dose during non-continuous administration of the antibody, e.g. in one or more of the examples described above. In certain embodiments, the daily morphine dose administered in a continuous antibody infusion schedule is 80% or less of the morphine dose administered in or prescribed for a non-continuous antibody infusion schedule in the first treatment cycle, 58% or less in the second treatment cycle, 57% or less in the third treatment cycle, 42% or less in the fourth treatment cycle, 34% or less in the fifth treatment cycle. In one embodiment, the daily morphine dose administered in an antibody treatment schedule according to the invention (e.g. with no cytokine and/or as continuous antibody infusion) is lower than the daily morphine dose administered in an antibody treatment schedule of a continuous intravenous antibody infusion for 5 days in a daily dose of 40 $mg/m^2$. In some embodiments, the daily morphine dose administered during one or more days of continuous intravenous infusion of the antibody according to the invention and/or of all antibody or morphine treatment days is lower than 0.9, 0.72, 0.48, 0.38, 0.4375, and/or 0.205 mg/kg/day.

In certain embodiments, the daily morphine dose administered on the fifth, sixth, seventh, eighths, ninth, and/or tenth day of administration of the antibody in the first treatment cycle (applying a continuous intravenous infusion of the antibody according to the invention) is lower than the daily morphine dose in a non-continuous infusion schedule, e.g. 78% or less. In certain embodiments, the morphine dose administered on said day and any following days of the treatment cycle and/or of the overall treatment time is lower than the daily morphine dose in a non-continuous infusion schedule. In certain embodiments, the daily morphine dose administered on the third, fourth, fifth, sixth, seventh, eighths, ninth, and/or tenth day of administration of the antibody in the second treatment cycle (applying a continuous intravenous infusion of the antibody according to the invention) is lower than the daily morphine dose in a non-continuous infusion schedule, e.g. 60% or less. In certain embodiments, the morphine dose administered on said day and any following days of the treatment cycle and/or of the overall treatment time is lower than the daily morphine dose in a non-continuous infusion schedule. In some embodiments, the daily morphine dose administered on the first day of administration of the antibody in the third and any following treatment cycles (applying a continuous intravenous infusion of the antibody according to the invention) is lower than the daily morphine dose in a non-continuous infusion schedule, e.g. 57% or less. In certain embodiments, the morphine dose administered on said day and any following days of the treatment cycle and/or of the overall treatment time is lower than the daily morphine dose in a non-continuous infusion schedule.

In some embodiments of inventive treatment schedules, morphine is administered only for some but not all days on which the antibody is administered, e.g. only on the first 1, 2, 3, 4, 5, 6, or 7 days (e.g. in treatment cycles two, three, four, and/or five) of continuous antibody infusion and/or of antibody administration with no cytokine. In some embodiments, no morphine is administered on one or more days of the inventive antibody administration schedule, or even within the entire treatment cycle. In some embodiments, morphine is administered only in some but not all treatment cycles. In an embodiment, in cycle 6 of continuous antibody infusion, no morphine is administered.

In some embodiments, the morphine infusion rate, i.e. the morphine amount per kg body weight of the patient (or morphine dose) per hour, administered during one or more hours or days of the continuous intravenous infusion of the antibody according to the invention and/or the antibody administration with no cytokine according to the invention and/or of all hours or days of morphine treatment is lower than the standard morphine infusion rate prescribed for a usual schedule with non-continuous infusion and/or with usual cytokine doses, and/or lower than the morphine infusion rate in the examples with non-continuous infusion and/or usual cytokine doses described above. In some embodiments, the morphine infusion rate, i.e. the morphine amount per kg body weight of the patient (or morphine dose) per hour, administered during one or more hours or days of the continuous intravenous infusion of the antibody according to the invention and/or of all hours or days of morphine treatment is lower than the standard morphine infusion rate prescribed for said usual schedule and/or the morphine infusion rate during non-continuous administration of the antibody in the examples described above, e.g. 96% or less on the second, 84% or less on the third, 65% or less on the fourth, 41% or less on the fifth, 14% on the sixth, 5% or less on the seventh, 3% on the eighth, 2% or less on the ninth, and/or 1% on the tenth day in the first treatment cycle, 72% or less in the second treatment cycle, 30% or less in the third treatment cycle, 22% or less in the fourth treatment cycle, 18% or less in the fifth treatment cycle. In some embodiments, the morphine infusion rate administered during one or more days of intravenous infusion of the antibody with no cytokine according to the invention and/or of all antibody or morphine treatment days is lower than 50, 40, 30, 20, 10, and/or 5 mcg/kg/h, and/or lower than any range in between these infusion rates. In some embodiments, the morphine infusion rate administered during one or more days of continuous intravenous infusion of the antibody according to the invention and/or of all antibody or morphine treatment days is lower than 50, 40, 30, 20, 10, and/or 5 mcg/kg/h, and/or lower than any range in between these infusion rates. In some embodiments, the morphine infusion rate administered during one or more days of continuous intravenous infusion of the antibody according to the invention and/or of all antibody or morphine treatment days is lower than 30 mcg/kg/h in the first and optionally any following treatment cycles, lower than 22 mcg/kg/h in the second and optionally any following treatment cycles, lower than 10 mcg/kg/h in the third and optionally any following treatment cycles, lower than 7 mcg/kg/h in the fourth and optionally any following treatment cycles, and/or lower than 6 mcg/kg/h in the fifth and optionally any following treatment cycles. In some embodiments, the morphine infusion rate administered during one or more days of intravenous infusion of the antibody with no cytokine according to the invention and/or of all antibody or morphine treatment days is lower than 50 mcg/kg/h in the first and optionally any following treatment cycles, lower than 40 mcg/kg/h in the second and optionally any following treatment cycles, lower than 30 mcg/kg/h in the third and optionally any following treatment cycles, lower than 20 mcg/kg/h in the fourth and optionally any following treatment cycles, and/or lower than 10 mcg/kg/h in the fifth and optionally any following treatment cycles.

In certain embodiments, the morphine dose per treatment cycle administered during one or more treatment cycles comprising the continuous intravenous infusion of the antibody according to the invention is lower than the morphine dose per treatment cycle in a non-continuous infusion schedule, e.g. 66% or less in the first treatment cycle; 64% or less, or 28% or less in the second treatment cycle; 29% or less, or 13% or less in the third treatment cycle; 16% or less, or 7% or less in the fourth treatment cycle; and/or 15% or less, or 6% or less in the fifth treatment cycle.

In certain embodiments, the morphine dose per treatment cycle administered during one or more treatment cycles comprising the intravenous infusion of the antibody with no cytokine according to the invention is lower than the morphine dose per treatment cycle in an infusion schedule with usual cytokine treatment, e.g. 90%, 80%, 70%, or less in the first treatment cycle; 80%, 70%, 60%, or less in the second treatment cycle; 60%, 50%, 40%, or less in the third treatment cycle; 45%, 35%, 25%, or less in the fourth treatment cycle; and/or 30%, 20%, 10% or less in the fifth treatment cycle.

In certain embodiments, the morphine dose per treatment cycle of the second and any following treatment cycles administered during one or more treatment cycles comprising the continuous intravenous infusion of the antibody and/or the antibody administration with no cytokine according to the invention is lower than the morphine dose per treatment cycle in a non-continuous infusion schedule and/or in an administration schedule of an antibody with usual cytokine doses. In certain embodiments, the morphine dose of said treatment cycle and any following treatment cycles, and/or of the overall treatment time is lower than the morphine dose per treatment cycle in a usual infusion schedule (e.g. non-continuous and/or with usual cytokine doses). In some embodiments, the morphine dose per treatment cycle administered during one or more treatment cycles comprising the continuous intravenous infusion of the antibody and/or the antibody administration with no cytokine according to the invention is lower than 7.2, 4.8, 4.5, 2, 1.75, and/or 0.82 mg/kg/cycle, or lower than any range in between these doses.

In some embodiments, the morphine dose of the overall treatment time in an inventive infusion schedule (e.g. applying a continuous intravenous infusion of the antibody and/or applying an antibody administration schedule with no cytokine(s)) is lower than the morphine dose of the overall treatment time in a usual infusion schedule (e.g. an antibody infusion schedule with the usual cytokine dose(s) and/or a non-continuous antibody infusion schedule).

In one embodiment, the morphine dose of the overall treatment time (applying a continuous intravenous infusion of the antibody according to the invention) is 55% or less, 50% or less, 45% or less, 40% or less, 30% or less, 20% or less, 10% or less, of the morphine dose of the overall treatment time in a non-continuous infusion schedule, and/or lower than any range in between these doses. In some embodiments, the morphine dose of the overall treatment time (applying a continuous intravenous infusion of the antibody according to the invention) is lower than 43.2, 28.8, 13.5, 10, 8.75, and/or 4.1 mg/kg/overall treatment time, and/or lower than any range in between these doses.

In one embodiment, the morphine dose of the overall treatment time in an inventive infusion schedule (with no cytokine(s) treatment and/or in a continuous antibody infusion schedule) is 90% or less, 80% or less, 70% or less, 60% or less, or 50% or less, 40% or less, 30% or less, 20% or less, 10% or less, of the morphine dose of the overall treatment time in a usual infusion schedule (with usual cytokine(s) treatment and/or in a non-continuous antibody infusion schedule), and/or lower than any range in between these doses. In some embodiments, the morphine dose of the overall treatment time in an inventive infusion schedule without cytokine treatment and/or with continuous antibody infusion is lower than 43.2, 28.8, 13.5, 10, 8.75, and/or 4.1 mg/kg/overall treatment time, and/or lower than any range in between these doses.

In some embodiments, the reference morphine doses in usual infusion schedules (with usual cytokine(s) treatment schedules and/or in a non-continuous antibody infusion schedule), as referred to herein in comparison to the morphine doses in infusion schedules according to the present invention (with no cytokine(s) treatment and/or in a continuous antibody infusion schedule), refer to the standard morphine doses for said schedule, or morphine doses prescribed for said schedule (e.g. as specified in the clinical study protocols). In some embodiments, the reference morphine doses as referred to herein refers to the morphine dose administered on the first day of treatment with the preparation comprising an anti-GD2 antibody in a treatment cycle with an inventive and/or usual antibody infusion schedule, and is referred to as "starting morphine dose".

Accordingly, the term "reference morphine dose" as used herein shall comprise the morphine doses of treatment schedules other than those according to the present invention (e.g. treatment schedules described in the prior art, e.g. with usual cytokine treatment and/or non-continuous antibody infusion), and/or starting morphine doses (e.g. of treatment schedules with or without cytokine treatment and/or with or without continuous antibody infusion); and shall encompass all examples of such morphine doses as referred to herein in comparison to the other morphine doses in antibody infusion schedules with no cytokine(s) and/or with continuous antibody infusion according to the present invention.

In certain embodiments, the reference morphine dose per hour infusion, i.e. the reference infusion rate, during the administration period of the antibody is 50 mcg/kg/h. In certain embodiments, the reference morphine dose per hour infusion, i.e. the reference infusion rate, during the administration period of the antibody is 30 mcg/kg/h. In certain embodiments, the reference morphine dose is 50, 40, 30, and/or 20 mcg/kg/h. In certain embodiments, the reference morphine dose is 0.9, 0.72, 0.48, 0.38, 0.4375, and/or 0.205 mg/kg/day. In certain embodiments, the reference morphine dose is 7.2, 4.8, 4.5, 2, 1.75, and/or 0.82 mg/kg/cycle. In certain embodiments, the reference morphine dose is 43.2, 28.8, 13.5, 10, 8.75, and/or 4.1 mg/kg/overall treatment time. In certain embodiments, the reference indometacin dose is 0.3 to 0.5 mg/kg/dose, or 25 or 50 mg/dose, orally or intravenously every 6 hours. In some embodiments, the reference morphine doses in usual infusion schedules, as referred to above in comparison to the morphine doses in inventive infusion schedules, refer to the morphine doses as actually administered to the patients (e.g. the respective mean of the morphine doses administered to all treated patients of a group treated in the same setting).

The morphine doses in inventive infusion schedules, as referred to herein in comparison to the morphine doses in usual infusion schedules, may refer to the reduced standard morphine doses for said inventive schedule, or reduced morphine doses prescribed for said schedule (e.g. as specified in the clinical study protocols). In certain embodiments, the reduced morphine dose in an inventive infusion schedule per hour infusion, i.e. the infusion rate, during one or more hours or days of the inventive administration of the antibody with no cytokine(s) and/or in a continuous infusion is lower than 50 mcg/kg/h. In certain embodiments, the morphine dose per hour infusion, i.e. the infusion rate, during one or more hours or days of the inventive administration of the antibody is lower than 30 mcg/kg/h. In some embodiments, the morphine doses in infusion schedules according to the present invention (e.g. without cytokine(s) and/or as continuous infusion), as referred to above in comparison to the morphine doses in usual infusion schedules (e.g. with cytokine(s) and/or in non-continuous infusion), refer to the morphine doses as actually administered to the patients (e.g. the respective mean of the morphine doses administered to all treated patients of a group treated in the same setting).

In some embodiments, the reference morphine doses in non-continuous infusion schedules, as referred to above in comparison to the morphine doses in continuous infusion schedules according to the present invention, refer to the morphine doses as actually administered to the patients (e.g. the respective mean of the morphine doses administered to all treated patients of a clinical study and/or in the same setting).

The morphine doses in continuous infusion schedules according to the present invention, as referred to herein in comparison to the morphine doses in non-continuous infusion schedules, may refer to the standard morphine doses for said schedule, or morphine doses prescribed for said schedule (e.g. as specified in the clinical study protocols). In certain embodiments, the morphine dose per hour infusion, i.e. the infusion rate, during one or more hours or days of the continuous administration of the antibody is lower than 50 mcg/kg/h. In certain embodiments, the morphine dose per hour infusion, i.e. the infusion rate, during one or more hours or days of the continuous administration of the antibody is lower than 30 mcg/kg/h.

In general, individual analgesic doses may vary depending on the individual patient's pain tolerance. Dosing may be adapted to obtain optimal analgesia.

The treatment period with the preparation comprising an anti-GD2 antibody may be combined with one or more treatment periods with a cytokine (according to the first aspect of the invention), one or more treatment periods with a retinoid, one or more treatment periods with an analgesic, and/or one or more treatment periods with another drug or treatment (except for cytokine treatment in the second aspect of the invention), and/or one or more treatment periods with no treatment. In one embodiment, the treatment period with the preparation comprising an anti-GD2 antibody combined with one or more of any such other treatment periods represent one treatment cycle. Accordingly, in an embodiment, a treatment cycle comprises a treatment period with the preparation comprising an anti-GD2 antibody and optionally one or more treatment periods with other drugs, agents, and/or treatments. Any such treatment periods within one treatment cycle may partially and/or entirely overlap, as further described herein.

In one embodiment, a patient who is treated with the antibody is also treated with a retinoid (e.g. isotretinoin), and optionally with one or more cytokines (according to the first aspect of the invention), such as IL-2 and/or GM-CSF, and optionally morphine and/or one or more morphine derivatives, and/or one or more other analgesics. In one embodiment, the treatment period with the preparation comprising an anti-GD2 antibody is not accompanied by a treatment period with morphine and/or one or more analgesics. In one embodiment, the treatment period with the preparation comprising an anti-GD2 antibody is not accompanied by a treatment period with one or more cytokines. In one embodiment, the treatment period with the preparation comprising an anti-GD2 antibody is not preceded and/or followed by a treatment period with one or more cytokines.

In one embodiment, the treatment period with the preparation comprising an anti-GD2 antibody is not preceded and/or followed by a treatment period with one or more cytokines and not accompanied by a treatment period with one or more cytokines.

In one embodiment, one treatment cycle comprises 28 to 49 days, e.g. 28, 35, 42, or 49 days or any range in between these periods. The treatment cycle starts with the day when the patient first receives any of the treatments comprised in said cycle (may be designated as day 0 or day 1), e.g. the administration of a preparation comprising an anti-GD2 antibody, and/or any other preparation or treatment.

The treatment period with the anti-GD2 antibody may be preceded, accompanied, and/or followed by a treatment period with a retinoid (e.g. isotretinoin), either directly or with an interval of one or more days of no treatment, e.g. 1, 2, 3, 4, or 5 days of no treatment. In one embodiment, the retinoid (e.g. isotretinoin) is administered orally twice a day in a dose of 160 $mg/m^2/day$ (in equal doses, i.e. 2×80 $mg/m^2$). In one embodiment, the retinoid (e.g. isotretinoin) is administered for 14 days, e.g. from day 1 to day 14 of a treatment cycle, or from day 19 to day 32 of the treatment cycle. The treatment period with the retinoid (e.g. isotretinoin) may be followed by an interval of one or more days of no treatment, e.g. 1, 2, 3, 4, or 5 days of no treatment.

In one embodiment, the treatment cycle comprises one 14-day treatment period with the retinoid (e.g. isotretinoin), e.g. on days 1 to 14 of the treatment cycle, followed by 7 days of no treatment (day 15-21 of the treatment cycle), and a 5-day treatment period with the anti-GD2 antibody (e.g. with 20 $mg/m^2/day$ infused over 8 hours to administer a dose of 100 $mg/m^2/cycle$), e.g. on days 22 to 26 of the treatment cycle, before the next cycle begins on day 29, which is then day 1 of the next treatment cycle. In other embodiments, the treatment cycle comprises one 14-day treatment period with a retinoid (e.g. isotretinoin), e.g. on days 1 to 14 of the treatment cycle, followed by one 5-day treatment period with the anti-GD2 antibody (e.g. with 20 $mg/m^2/day$ infused over 8 hours to administer a dose of 100 $mg/m^2/cycle$), e.g. on days 22 to 28 of the treatment cycle, before the next cycle begins on day 29, which is then day 1 of the next treatment cycle.

In one embodiment, the treatment cycle comprises one 10-day treatment period with the anti-GD2 antibody (e.g. with 10 or 15 $mg/m^2/day$ to administer a dose of 100 or 150 $mg/m^2/cycle$), e.g. on days 8 to 17 of the treatment cycle, and one 14-day treatment period with a retinoid (e.g. isotretinoin), e.g. on days 19 to 32 of the treatment cycle, followed by 3 days of no treatment, before the next cycle begins on day 36, which is then day 1 of the second treatment cycle.

In one embodiment of the first aspect of the invention, the treatment cycle comprises two 5-day treatment periods with the cytokine, e.g. on days 1 to 5 and 8 to 12 of the treatment cycle, one 10-day treatment period with the anti-GD2 antibody (e.g. with 10 or 15 $mg/m^2/day$ to administer a dose of 100 or 150 $mg/m^2/cycle$), e.g. on days 8 to 17 of the treatment cycle, and one 14-day treatment period with a retinoid (e.g. isotretinoin), e.g. on days 19 to 32 of the treatment cycle, followed by 3 days of no treatment, before the next cycle begins on day 36, which is then day 1 of the second treatment cycle.

In one embodiment, the treatment cycle optionally comprises two 5-day treatment periods with the cytokine, e.g. on days 1 to 5 and 8 to 12 of the treatment cycle, and comprises one 14-day treatment period with the anti-GD2 antibody (e.g. with 7 or 15 $mg/m^2/day$ to administer a dose of 100 or 210 $mg/m^2/cycle$), e.g. on days 8 to 21 of the treatment cycle, and further comprises one 14-day treatment period with a retinoid (e.g. isotretinoin), e.g. on days 26 to 39 of the treatment cycle, followed by 3 days of no treatment, before the next cycle begins on day 43, which is then day 1 of the second treatment cycle.

In one embodiment, the treatment cycle optionally comprises two 5-day treatment periods with the cytokine, e.g. on days 1 to 5 and 8 to 12 of the treatment cycle, and comprises one 15-day treatment period with the anti-GD2 antibody (e.g. with 10 $mg/m^2/day$ to administer a dose of 150 $mg/m^2/cycle$), e.g. on days 8 to 22 of the treatment cycle, and one 14-day treatment period with a retinoid (e.g. isotretinoin), e.g. on days 26 to 39 of the treatment cycle, followed by 3 days of no treatment, before the next cycle begins on day 43, which is then day 1 of the second treatment cycle.

In one embodiment, the treatment cycle optionally comprises two 5-day treatment periods with the cytokine, e.g. on days 1 to 5 and 8 to 12 of the treatment cycle, and comprises one 21-day treatment period with the anti-GD2 antibody (e.g. with 7 or 10 $mg/m^2/day$ to administer a dose of 150 or 210 $mg/m^2/cycle$), e.g. on days 8 to 28 of the treatment cycle, and one 14-day treatment period with a retinoid (e.g. isotretinoin), e.g. on days 33 to 46 of the treatment cycle, followed by 3 days of no treatment, before the next cycle begins on day 50, which is then day 1 of the second treatment cycle.

In one embodiment of the first aspect of the invention, the treatment cycle comprises one 3-day treatment period with the immunocytokine (e.g. APN301), e.g. on days 4 to 6 of the treatment cycle, two treatment periods with the cytokine, e.g. GM-CSF, e.g. on days 1 and 2 and on 8 to 14 of the treatment cycle, and one 14-day treatment period with isotretinoin, e.g. on days 11 to 24 of the treatment cycle, followed by 4 days of no treatment, before the next cycle begins on day 29, which is then day 1 of the second treatment cycle.

In one embodiment, the treatment cycle comprises one 4-day treatment period with the preparation comprising the anti-GD2 antibody (e.g. ch14.18/SP2/0), for example administered in a dose of 25 $mg/m^2/day$, e.g. on days 3 to 6 of a 24-day treatment cycle beginning with day 0, or on days 7 to 10 of a 32-day treatment cycle beginning with day 0, e.g. for 5 cycles; and one treatment period with RA, e.g. isotretinoin on days 10 to 23 of a treatment cycle beginning with day 0, or on days 14 to 27 of a treatment cycle beginning with day 0. In one embodiment of the first aspect of the invention, the treatment cycle comprises one 4-day treatment period with the preparation comprising the anti-GD2 antibody (e.g. ch14.18/SP2/0), for example administered in a dose of 25 $mg/m^2/day$, e.g. on days 3 to 6 of a 24-day treatment cycle beginning with day 0 (if GM-CSF is used as cytokine), or e.g. on days 7 to 10 of a 32-day treatment cycle beginning with day 0 (if IL-2 is used as cytokine), for 5 cycles (e.g. the first with GM-CSF, the second with IL-2, the third with GM-CSF, the fourth with IL-2, and the fifth with GM-CSF); one or two treatment periods with a cytokine (e.g. GM-CSF at 250 micrograms/$m^2$/day for 14 days, on days 0 to 13 of a treatment cycle beginning with day 0; or Aldesleukin (IL-2) in a dose of 3 MIU/$m^2$/day on days 0 to 3 and 4.5 MIU/$m^2$/day on days 7 to 10 of a treatment cycle beginning with day 0, and one treatment period with RA, e.g. isotretinoin on days 10 to 23 of a treatment cycle beginning with day 0 (if GM-CSF is used as cytokine), or on days 14 to 27 of a treatment cycle beginning with day 0 (if IL-2 is used as cytokine). In an embodiment, the treatment schedule is as specified in Table 2, 3 and/or 4 (but with continuous antibody infusion and/or without cytokine(s)).

The treatment cycle may be repeated, either identically or in an amended form, e.g. with a different dose or schedule, or with different additional treatments (e.g. with one or more other analgesics and/or cytokines). Thus, the overall treatment time (e.g. the time period comprising all subsequent treatment cycles, or the overall continuous treatment period) may comprise at least 1, or 2 or more cycles, or 10 or more cycles. In one embodiment, the preparation comprising an anti-GD2 antibody is administered to the patient in two or more treatment cycles. In an embodiment, the preparation comprising an anti-GD2 antibody is administered to the patient as a continuous infusion in two or more treatment cycles. In an embodiment, the preparation comprising an anti-GD2 antibody is administered to the patient as a continuous infusion in two or more treatment cycles without concomitantly administering IL-2. In one embodiment, the overall treatment time comprises 1, 2, 3, 4, 5, 6, 7, 8, 9, 10, 11, 12, 13, 14, 15, 16, 17, 18, 19, or 20 cycles, or more. The overall treatment time may even comprise up to 20 or more treatment cycles. As described above, treatment cycles may comprise time periods of no treatment (intervals in which no treatment is administered to the patient, i.e. no antibody, no cytokine, no other drug). Thus, as used herein, the overall treatment time may also comprise said intervals of no treatment within treatment cycles.

In one embodiment, the 35, 42, or 49 day treatment cycle as specified above is repeated at least 4 or 5 times, so that the overall continuous treatment period comprises at least 5 or 6 treatment cycles.

The effect of the antibody treatment (e.g. as continuous infusion and/or without one or more cytokines) may be determined by a complement dependent cytolysis (CDC) assay or a whole blood test (WBT). The WBT is an assay in which the target cells or target components (i.e. cells, liposomes or other cell-like compartments to be lysed) are contacted with appropriately anti-coagulated whole blood from the patient. The CDC assay can be, for example, a standard CDC assay as known in the art (e.g. as described in Indusogie et al., J Immunol 2000; 164 (8):4178-84; Zeng et al. Molecular Immunology 2005; 42 (11):1311-9; or in WO2005/070967). The CDC assay and/or the WBT may be done with GD2 positive target cells, such as tumor cell lines of the GD2 positive cancer to be treated. For example, if the patient to be treated suffers from neuroblastoma, the cell line may be a neuroblastoma cell line, such as e.g. LAN-1 human neuroblastoma cells. In another example, if the patient to be treated suffers from melanoma, the cell line may be a melanoma cell line, such as e.g. M21 human melanoma cells. In still another example, the target cells of the CDC assay and/or the WBT are tumor cells obtained from the patient, i.e. autologous tumor cells of the patient. In another embodiment, the target component of the CDC assay and/or WBT is a liposome displaying GD2 on the surface. The target cells or target components are labeled with a signaling component, e.g. with a radioactive component, such as $^{51}Cr$, or with a fluorescent component, such as calcein. The signaling component is comprised by the target cell or target component, i.e. is inside of the target cell or target component (e.g. a liposome packed with the signaling component and displaying GD2 on the surface), and is released upon lysis of the target cell or target component. Thus, the signaling component provides the assay readout. The target cells or components loaded with the signaling compound are contacted with the whole blood, serum, or plasma in a certain ratio. The whole blood, plasma, or serum may be diluted for the CDC or WBT, e.g. in a ratio of 1:2 or higher, e.g. 1:4, 1:5, or 1:10, or any range in between these ratios prior to adding it to the sample. However, it may also be added to the sample un-diluted. The final concentration of the whole blood, plasma, or serum in the CDC or WBT sample may e.g. be in the range of 10 to 50%. Target cell or target component lysis can be measured by release of said signaling component by a scintillation counter or spectrophotometry. For example, the target cell or target component lysis can be measured by determining the amount of $^{51}Cr$ released into the supernatant by a scintillation counter. The percentage of lysis may be determined by the following equation: 100×(experimental release−spontaneous release)/(maximum release−spontaneous release).

For the CDC assay, the cytolytic components (or effector components) are provided by serum or appropriately anti-coagulated plasma obtained from the patient or donor comprising the complement system components. For the WBT, the cytolytic components (or effector components) are provided by appropriately anti-coagulated whole blood obtained from the patient or donor comprising the complement system components as well as all cellular components, and also any further components comprised in whole blood which might be relevant to the target cell lysis, as well as the interplay of all components (e.g. complement activation is known to activate certain effector cells such as granulocytes) For the CDC and/or WBT, the serum, plasma, or whole blood may be added to the target cells or target components in different dilutions.

Furthermore, one or more samples of the CDC assay and/or WBT may be spiked with an anti-GD2 antibody in different concentrations, e.g. for generation of a standard curve.

In another embodiment, one or more anti-idiotypic (anti-id) anti-GD2 antibodies recognizing the variable domain of anti-GD2 antibodies may be added to a sample to inhibit the target cell lysis mediated by the antibody, e.g. as a negative control or to prove specificity of the assay and that the target cell lysis measured without the anti-id antibody is antibody-mediated or antibody dependent.

In certain embodiments, the increased level of cytolysis after the one or more initial antibody treatment days (compared to the level of cytolysis prior to antibody treatment) is maintained over the entire treatment cycle. In some embodiments, said increased level of cytolysis is maintained over the overall treatment time, i.e. even for time periods, where the patient is not treated with the preparation comprising an anti-GD2 antibody, i.e. in the intervals between the treatment periods with the preparation comprising an anti-GD2 antibody (if any, i.e. if the patient is not treated continuously over the overall treatment time with the preparation comprising an anti-GD2 antibody). In one embodiment, the level of cytolysis (level of target cell lysis, e.g. measured in a CDC assay or WBT) of a blood sample of a patient treated according to the present invention is increased compared to the level of cytolysis prior to the first treatment period with the preparation comprising the antibody over the entire time period starting from the end of the first antibody treatment period to the end of the last treatment cycle, i.e. even between the time periods of antibody treatment. In one embodiment, said level of cytolysis is at least 10%, 20%, 30%, 40%, 50%, 60%, 70%, 80%, 90% or 100%, or any range in between these levels, over the entire time period starting from the end of the first antibody treatment period to the end of the last treatment cycle. In an embodiment, the level of cytolysis after the first, second, third, fourth, fifth, sixth, seventh, eights, ninths, and/or tenth treatment period with the anti-GD2 antibody is at least 10%, 20%, 30%, 40%, 50%, 60%, 70%, 80%, 90% or 100%, or any range in between these levels. In an embodiment, the level of cytolysis prior to the second, third, fourth, fifth, sixth, seventh, eights, ninths, and/or tenth treatment period with the anti-GD2 antibody is at least 10%, 20%, 30%, 40%, 50%, 60%, 70%, 80%, 90% or 100%, or any range in between these levels.

DEFINITIONS OF SPECIFIC EMBODIMENTS

The present invention may be more specifically defined as follows:

Definition 1: A method for treating a GD2 positive cancer by administering a preparation comprising an anti-GD2 antibody to a patient as a continuous intravenous infusion over 24 hours per day.

Definition 2: A method according to definition 1, wherein the preparation comprising an anti-GD2 antibody is administered in a dose sufficient to induce tumor cell lysis (cytolysis threshold dose).

Definition 3: A method according to definition 2, wherein the cytolysis threshold dose is determined individually for each patient.

Definition 4: A method according to definitions 2 or 3, wherein the cytolysis threshold dose is determined by a complement dependent cytolysis assay.

Definition 5: A method according to definitions 2 or 3, wherein the cytolysis threshold dose is determined by a whole blood test.

Definition 6: A method according to any of definitions 1 to 5, wherein the cytolysis threshold dose is the dose determined in a specific CDC assay or WBT to induce at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% of the maximal possible target cell lysis in that respective assay.

Definition 7: A method according to any of definitions 1 to 6, wherein the cytolysis threshold dose is the dose determined in a specific CDC assay or WBT to induce 30%, 35%, 40%, 45%, 50%, 55%, 60%, 65%, 70%, 75%, 80%, 85%, 90%, 95%, or 100% of the maximal possible target cell lysis in that respective assay.

Definition 8: A method according to any of definitions 1 to 7, wherein the cytolysis threshold dose is 470 to 1000, 470 to 10000, 1410 to 3000, or 2350 to 5000 ng/mL serum or plasma.

Definition 9: A method according to any of definitions 1 to 8, wherein the cytolysis threshold dose is 2 to 250, 2 to 2500, 2 to 100, 5 to 200, 6 to 750, 6 to 7500, 10 to 1250, 10 to 12500, 6 to 300, 10 to 500, 15 to 600, or 25 to 1000 ng/mL whole blood.

Definition 10: A method according to any of definitions 1 to 9, wherein the preparation comprising an anti-GD2 antibody is administered in a dose to achieve the cytolysis threshold dose in the patient's serum, plasma or whole blood within 1, 2, 3, or 4 days of the treatment with the preparation comprising an anti-GD2 antibody.

Definition 11: A method according to any of definitions 1 to 10, wherein the threshold cytolysis is maintained even for one or more time periods within the overall treatment time, where the patient is not treated with the preparation comprising an anti-GD2 antibody.

Definition 12: A method according to any of definitions 1 to 11, wherein the level of cytolysis is maintained over the entire treatment cycle.

Definition 13: A method according to any of definitions 1 to 12, wherein the level of cytolysis is maintained over the overall treatment time.

Definition 14: A method according to any of definitions 1 to 13, wherein the preparation comprising an anti-GD2 antibody is administered in a daily dose of 1 to 30 $mg/m^2$, 1 to 35 $mg/m^2$, 1 to 50 $mg/m^2$, or 1 to 60 $mg/m^2$.

Definition 15: A method according to any of definitions 1 to 14, wherein the preparation comprising an anti-GD2 antibody is administered in a daily dose of 1, 2, 3, 4, 5, 6, 7, 7.5, 8, 9, 10, 12, 15, 20, 25, 30, 32, 35, 40, 45, 50, or 60 $mg/m^2$.

Definition 16: A method according to any of definitions 1 to 15, wherein the preparation comprising an anti-GD2 antibody is administered for a treatment period until the predetermined overall patient dose has been administered.

Definition 17: A method according to any of definitions 1 to 16, wherein the preparation comprising an anti-GD2 antibody is administered for a treatment period until a certain therapeutic effect has been reached.

Definition 18: A method according to any of definitions 1 to 17, wherein the preparation comprising an anti-GD2 antibody is administered by using a mini-pump.

Definition 19: A method according to any of definitions 1 to 18, wherein the anti-GD2 antibody is a chimeric or humanized antibody.

Definition 20: A method according to any of definitions 1 to 19, wherein the anti-GD2 antibody is ch14.18/CHO or ch14.18/SP2/0.

Definition 21: A method according to any of definitions 1 to 20, wherein the preparation comprising the anti-GD2 antibody is APN311 or APN301.

Definition 22: A method according to any of definitions 1 to 21, wherein the preparation comprising an anti-GD2 antibody is administered in a dose of 7, 10, 15, or 25 $mg/m^2$/day.

Definition 23: A method according to any of definitions 1 to 22, wherein the preparation comprising an anti-GD2 antibody is administered for 4, 10, 14, 15, or 21 consecutive days.

Definition 24: A method according to any of definitions 1 to 23, wherein the preparation comprising an anti-GD2 antibody is administered for 3, 4, 5, or 6 treatment cycles.

Definition 25: A method according to any of definitions 1 to 24, wherein the preparation comprising an anti-GD2 antibody is APN311 and is administered in a dose of 10 $mg/m^2$/day for 10 consecutive days for 6 treatment cycles.

Definition 26: A method according to any of definitions 1 to 24, wherein the anti-GD2 antibody is ch14.18/SP2/0 and is administered in a dose of 25 $mg/m^2$/day for 4 consecutive days for 5 treatment cycles.

Definition 27: A method according to any of definitions 1 to 26, wherein the administration of the preparation comprising an anti-GD2 antibody is preceded and/or accompanied by the administration of IL-2 and/or GM-CSF or another cytokine.

Definition 28: A method according to any of definitions 1 to 27, wherein the administration period of the preparation comprising an anti-GD2 antibody may be followed by an administration period of isotretinoin or another retinoid.

Definition 29: A method according to any of definitions 1 to 28, wherein the administration of the preparation comprising an anti-GD2 antibody is accompanied by the administration of morphine and/or one or more other analgesics.

Definition 30: A method according to any of definitions 1 to 29, wherein the daily morphine dose administered during one or more days of continuous intravenous infusion of the antibody according to the invention and/or of all morphine treatment days is lower than the daily morphine dose during non-continuous administration of the antibody.

Definition 31: A method according to any of definitions 1 to 30, wherein morphine is administered only for some but not all days on which the antibody is administered.

Definition 32: A method according to any of definitions 1 to 31, wherein the morphine dose per treatment cycle administered during one or more treatment cycles comprising the continuous intravenous infusion of the antibody according to the invention is lower than the morphine dose per treatment cycle in a non-continuous infusion schedule.

Definition 33: A method according to any of definitions 1 to 32, wherein the morphine dose of the overall treatment time is lower than the morphine dose of the overall treatment time in a non-continuous infusion schedule.

Definition 34: A method according to any of definitions 1 to 33, wherein the morphine dose administered during one or more hours or days of continuous intravenous infusion of the antibody according to the invention and/or of all morphine treatment hours or days is lower than 50 mcg/kg/h, or lower than 30 mcg/kg/h.

Definition 35: A method according to any of definitions 1 to 34, wherein the daily morphine dose administered during one or more days of continuous intravenous infusion of the antibody according to the invention and/or of all morphine treatment days is lower than 0.9, 0.72, 0.48, 0.38, 0.4375, and/or 0.205 mg/kg/day.

Definition 36: A method according to any of definitions 1 to 35, wherein the dose of the one or more analgesics, especially morphine, is reduced within the overall treatment time, within a treatment cycle, during the antibody treatment period within a treatment cycle, from one antibody treatment day to the next antibody treatment day within a treatment cycle, and/or from one treatment cycle to the next.

Definition 37: A method according to any of definitions 1 to 36, wherein the morphine dose is continuously reduced within a treatment cycle, during the antibody treatment period within a treatment cycle, and/or from one antibody treatment day to the next antibody treatment day within a treatment cycle.

Definition 38: An anti-GD2 antibody for use in a treatment according to any one of method definitions 1 to 37.

Definition 39: Use of an anti-GD2 antibody in the preparation of a medicament for the treatment according to any one of method definitions 1 to 37.

Definition 40: A preparation comprising an anti-GD2 antibody for use in the treatment of a GD2 positive cancer in a patient, wherein the preparation comprising an anti-GD2 antibody is administered to the patient without concomitantly administering IL-2, and wherein one or more treatment periods with the antibody is/are preceded, accompanied, and/or followed by one or more treatment periods with a retinoid.

Definition 41: A preparation comprising an anti-GD2 antibody for use in the treatment of a GD2 positive cancer in a patient, wherein the preparation comprising an anti-GD2 antibody is administered to the patient as a continuous infusion for one or more days and for two or more treatment cycles, without concomitantly administering IL-2.

Definition 42: A preparation comprising an anti-GD2 antibody for use in the treatment of a GD2 positive cancer in a patient, wherein the preparation comprising an anti-GD2 antibody is administered to the patient as a continuous infusion without concomitantly administering IL-2, and wherein the anti-GD2 antibody is not a 14G2a antibody.

Definition 43: A method for treating a GD2 positive cancer by administering a preparation comprising an anti-GD2 antibody to a patient, wherein the patient is not concomitantly treated with IL-2, and wherein one or more treatment periods with the antibody is/are preceded, accompanied, and/or followed by one or more treatment periods with a retinoid.

Definition 44: A method for treating a GD2 positive cancer in a patient, wherein a preparation comprising an anti-GD2 antibody is administered to the patient as a continuous infusion for one or more days and for two or more treatment cycles, and wherein the patient is not concomitantly treated with IL-2.

Definition 45: A method for treating a GD2 positive cancer in a patient, wherein the preparation comprising an anti-GD2 antibody is administered to the patient as a continuous infusion, wherein the patient is not concomitantly treated with IL-2, and wherein the anti-GD2 antibody is not a 14G2a antibody.

Definition 46: The preparation or method of any of definitions 40-45, wherein the patient is not concomitantly treated with GM-CSF.

Definition 47: The preparation or method of any of definitions 40-46, wherein the patient is not treated with a cytokine.

Definition 48: The preparation or method of any of definitions 40-47, wherein the patient is not treated with said cytokine(s) within the same treatment cycle.

Definition 49: The preparation or method of any of definitions 40-48, wherein the patient is not treated with said cytokine(s) within the same overall treatment period.

Definition 50: The preparation or method of any of definitions 40-49, wherein the patient may have been treated with IL-2, GM-CSF, and/or one or more other cytokines in one or more previous treatment cycles and/or overall treatment periods.

Definition 51: The preparation or method of any of definitions 40-50, wherein the GD2 positive cancer is neuroblastoma.

Definition 52: The preparation or method of any of definitions 40-51, wherein the patient has been diagnosed with minimal residual disease.

Definition 53: The preparation or method of any of definitions 40-52, wherein the patient has been diagnosed with relapsed and/or refractory disease.

Definition 54: The preparation or method of any of definitions 40-53, wherein the preparation comprising an anti-GD2 antibody is administered as a continuous intravenous infusion over 24 hours per day.

Definition 55: The preparation or method of any of definitions 40-54, wherein the preparation comprising an anti-GD2 antibody is administered in a daily dose of 1 to 30 $mg/m^2$, 1 to 35 $mg/m^2$, 1 to 50 $mg/m^2$, or 1 to 60 $mg/m^2$.

Definition 56: The preparation or method of any of definitions 40-55, wherein the preparation comprising an anti-GD2 antibody is administered by using a mini-pump.

Definition 57: The preparation or method of any of definitions 40-56, wherein the anti-GD2 antibody is ch14.18/CHO or ch14.18/SP2/0.

Definition 58: The preparation or method of any of definitions 40-57, wherein the preparation comprising the anti-GD2 antibody is APN311.

Definition 59: The preparation or method of any of definitions 40-58, wherein the preparation comprising an anti-GD2 antibody is administered in a dose of 7, 10, 15, or 25 $mg/m^2/day$.

Definition 60: The preparation or method of any of definitions 40-59, wherein the preparation comprising an anti-GD2 antibody is administered for 4, 10, 14, 15, or 21 consecutive days.

Definition 61: The preparation or method of any of definitions 40-60, wherein the preparation comprising an anti-GD2 antibody is administered for 3, 4, 5, 6, 7, 8, or 9 or more treatment cycles.

Definition 62: The preparation or method of any of definitions 40-61, wherein the preparation comprising an anti-GD2 antibody is APN311 and is administered in a dose of 10 $mg/m^2/day$ for 10 consecutive days for 6 or more treatment cycles.

Definition 63: The preparation or method of any of definitions 40-62, wherein the anti-GD2 antibody is ch14.18/SP2/0 and is administered in a dose of 25 $mg/m^2/day$ for 4 consecutive days for 5 or more treatment cycles.

Definition 64: The preparation or method of any of definitions 40-63, wherein the administration period of the preparation comprising an anti-GD2 antibody may be followed by an administration period of isotretinoin or another retinoid.

Definition 65: The preparation or method of any of definitions 40-64, wherein the administration of the preparation comprising an anti-GD2 antibody is accompanied by the administration of morphine and/or one or more other analgesics.

Definition 66: The preparation or method of any of definitions 40-65, wherein the administration of the preparation comprising an anti-GD2 antibody is accompanied by the administration of a reduced dose of morphine and/or one or more other analgesics.

Definition 67: The preparation or method of any of definitions 40-66, wherein the administration of the preparation comprising an anti-GD2 antibody is not accompanied by the administration of morphine and/or one or more other analgesics.

EXAMPLES

Example 1: APN311 and APN301 Sequences and Related Data

APN311 Sequence Data

TABLE 5

| Molecular Weight (MW) and pI (calculated) | | | | | |
|---|---|---|---|---|---|
| | pI 1) | MW [D] 1) | No. of AS | Conditions | 2D-DIGE 2) |
| Antibody | 8.61 | 144701.10 | 1324 | non-reducing | x |
| Antibody (½) | 8.58 | 72359.56 | 662 | reducing | x |
| Heavy Chain | 8.58 | 48306.59 | 442 | reducing | x |
| Light Chain | 8.48 | 24070.98 | 220 | reducing | x |

1) Calculated via http://web.expasy.org/compute_pi/

2) Due to the molecular weight of the dyes, shifts to slightly higher molecular weights are to be expected for 2D-DIGE Nucleotide Sequence (cDNA, Incl. Leader)

"TAG" works as a "stop codon" and therefore is not translated into the peptide sequence.

Light Chain (SEQ ID NO: 1):

1 ~~ATG GAA GCC CCA GCG CAG CTT CTC TTC CTC CTG CTA CTC TGG CTC CCA GAT ACC ACT GGA~~

61 GAA ATA GTG ATG ACG CAG TCT CCA GCC ACC CTG TCT GTG TCT CCA GGG GAA AGA GCC ACC

121 CTC TCC TGC AGA TCT AGT CAG AGT CTT GTA CAC CGT AAT GGA AAC ACC TAT TTA CAT TGG

181 TAC CTG CAG AAG CCA GGC CAG TCT CCA AAG CTC CTG ATT CAC AAA GTT TCC AAC CGA TTT

241 TCT GGG GTC CCA GAC AGG TTC AGT GGC AGT GGA TCA GGG ACA GAT TTC ACA CTC AAG ATC

301 AGC AGA GTG GAG GCT GAG GAT CTG GGA GTT TAT TTC TGT TCT CAA AGT ACA CAT GTT CCT

361 CCG CTC ACG TTC GGT GCT GGG ACC AAG CTG GAG CTG AAA CGA ACT GTG GCT GCA CCA TCT

421 GTC TTC ATC TTC CCG CCA TCT GAT GAG CAG TTG AAA TCT GGA ACT GCC TCT GTT GTG TGC

481 CTG CTG AAT AAC TTC TAT CCC AGA GAG GCC AAA GTA CAG TGG AAG GTG GAT AAC GCC CTC

541 CAA TCG GGT AAC TCC CAG GAG AGT GTC ACA GAG CAG GAC AGC AAG GAC AGC ACC TAC AGC

601 CTC AGC AGC ACC CTG ACG CTG AGC AAA GCA GAC TAC GAG AAA CAC AAA GTC TAC GCC TGC

661 GAA GTC ACC CAT CAG GGC CTG AGC TCG CCC GTC ACA AAG AGC TTC AAC AGG GGA GAG TGT

721 ~~TAG~~

Heavy Chain (SEQ ID NO: 2):

1 ~~ATG GGA TGG ACC TGG ATC TTT ATT TTA ATC CTC TCG GTA ACT ACA GGT GTC CAC TCT GAG~~

61 GTC CAA CTG CTG CAG TCT GGA CCT GAG CTG GAG AAG CCT GGC GCT TCA GTG ATG ATA TCC

-continued

121 TGC AAG GCT TCT GGT TCC TCA TTC ACT GGC TAC AAC ATG AAC TGG GTG AGG CAG AAC ATT

181 GGA AAG AGC CTT GAA TGG ATT GGA GCT ATT GAT CCT TAC TAT GGT GGA ACT AGC TAC AAC

241 CAG AAG TTC AAG GGC AGG GCC ACA TTG ACT GTA GAC AAA TCG TCC AGC ACA GCC TAC ATG

301 CAC CTC AAG AGC CTG ACA TCT GAG GAC TCT GCA GTC TAT TAC TGT GTA AGC GGA ATG GAG

361 TAC TGG GGT CAA GGA ACC TCA GTC ACC GTC TCC TCA GCC TCC ACC AAG GGC CCA TCG GTC

421 TTC CCC CTG GCA CCC TCC TCC AAG AGC ACC TCT GGG GGC ACA GCG GCC CTG GGC TGC CTG

481 GTC AAG GAC TAC TTC CCC GAA CCG GTG ACG GTG TCG TGG AAC TCA GGC GCC CTG ACC AGC

541 GGC GTG CAC ACC TTC CCG GCT GTC CTA CAG TCC TCA GGA CTC TAC TCC CTC AGC AGC GTG

601 GTG ACC GTG CCC TCC AGC AGC TTG GGC ACC CAG ACC TAC ATC TGC AAC GTG AAT CAC AAG

661 CCC AGC AAC ACC AAG GTG GAC AAG AGA GTT GAG CCC AAA TCT TGT GAC AAA ACT CAC ACA

721 TGC CCA CCG TGC CCA GCA CCT GAA CTC CTG GGG GGA CCG TCA GTC TTC CTC TTC CCC CCA

781 AAA CCC AAG GAC ACC CTC ATG ATC TCC CGG ACC CCT GAG GTC ACA TGC GTG GTG GTG GAC

841 GTG AGC CAC GAA GAC CCT GAG GTC AAG TTC AAC TGG TAC GTG GAC GGC GTG GAG GTG CAT

901 AAT GCC AAG ACA AAG CCG CGG GAG GAG CAG TAC AAC AGC ACG TAC CGT GTG GTC AGC GTC

961 CTC ACC GTC CTG CAC CAG GAC TGG CTG AAT GGC AAG GAG TAC AAG TGC AAG GTC TCC AAC

1021 AAA GCC CTC CCA GCC CCC ATC GAG AAA ACC ATC TCC AAA GCC AAA GGG CAG CCC CGA GAA

1081 CCA CAG GTG TAC ACC CTG CCC CCA TCC CGG GAG GAG ATG ACC AAG AAC CAG GTC AGC CTG

1141 ACC TGC CTG GTC AAA GGC TTC TAT CCC AGC GAC ATC GCC GTG GAG TGG GAG AGC AAT GGG

1201 CAG CCG GAG AAC AAC TAC AAG ACC ACG CCT CCC GTG CTG GAC TCC GAC GGC TCC TTC TTC

1261 CTC TAT AGC AAG CTC ACC GTG GAC AAG AGC AGG TGG CAG CAG GGG AAC GTC TTC TCA TGC

1321 TCC GTG ATG CAT GAG GCT CTG CAC AAC CAC TAC ACG CAG AAG AGC CTC TCC CTG TCC CCG

1381 GGT AAA ~~TGA~~ nucleotide 1 to 60 (striked out): leader sequence
last nucleotide (striked out): stop codon Peptide Sequence (Incl. Signal Peptide)

The signal peptide is split off during post translational processing and is not part of the final recombinant protein anymore.

Light Chain (SEQ ID NO: 3):

1 ~~M E A P A Q L L F L L L L W L P D T T G~~

21 E I V M T Q S P A T L S V S P G E R A T

41 L S C R S S Q S L V H R N G N T Y L H W

61 Y L Q K P G Q S P K L L I H K V S N R F

81 S G V P D R F S G S G S G T D F T L K I

101 S R V E A E D L G V Y F C S Q S T H V P

121 P L T F G A G T K L E L K R T V A A P S

141 V F I F P P S D E Q L K S G T A S V V C

161 L L N N F Y P R E A K V Q W K V D N A L

181 Q S G N S Q E S V T E Q D S K D S T Y S

-continued

201 L S S T L T L S K A D Y E K H K V Y A C

221 E V T H Q G L S S P V T K S F N R G E C

Heavy Chain (SEQ ID NO: 4):

1 ~~M G W T W I F I L I L S V T T G V H S E~~

21 V Q L L Q S G P E L E K P G A S V M I S

41 C K A S G S S F T G Y N M N W V R Q N I

61 G K S L E W I G A I D P Y Y G G T S Y N

81 Q K F K G R A T L T V D K S S S T A Y M

101 H L K S L T S E D S A V Y Y C V S G M E

121 Y W G Q G T S V T V S S A S T K G P S V

141 F P L A P S S K S T S G G T A A L G C L

161 V K D Y F P E P V T V S W N S G A L T S

-continued

| | |
|---|---|
| 181 | G V H T F P A V L Q S S G L Y S L S S V |
| 201 | V T V P S S S L G T Q T Y I C N V N H K |
| 221 | P S N T K V D K R V E P K S C D K T H T |
| 241 | C P P C P A P E L L G G P S V F L F P P |
| 261 | K P K D T L M I S R T P E V T C V V V D |
| 281 | V S H E D P E V K F N W Y V D G V E V H |
| 301 | N A K T K P R E E Q Y N S T Y R V V S V |
| 321 | L T V L H Q D W L N G K E Y K C K V S N |
| 341 | K A L P A P I E K T I S K A K G Q P R E |
| 361 | P Q V Y T L P P S R E E M T K N Q V S L |
| 381 | T C L V K G F Y P S D I A V E W E S N G |
| 401 | Q P E N N Y K T T P P V L D S D G S F F |
| 421 | L Y S K L T V D K S R W Q Q G N V F S C |
| 441 | S V M H E A L H N H Y T Q K S L S L S P |
| 461 | G K |

amino acid 1 to 20 (striked out): leader sequence

APN301 Sequence Data

TABLE 6

Molecular Weight (MW) and pI (calculated)

| | pI [1)] | MW [D] [1)] | No. of AS | Conditions | 2D-DIGE [2)] |
|---|---|---|---|---|---|
| Immunocytokine | 8.52 | 175741.35 | 1592 | non-reducing | x |
| Antibody | 8.61 | 144941.37 | 1326 | non-reducing | |
| Immunocytokine (½) | 8.49 | 87879.68 | 796 | reducing | x |
| Antibody (½) | 8.57 | 72479.69 | 663 | reducing | |
| Heavy Chain + IL-2 | 8.47 | 63861.72 | 576 | reducing | x |
| Heavy Chain | 8.59 | 48461.73 | 443 | reducing | |
| Light Chain | 8.27 | 24035.97 | 220 | reducing | x |
| IL-2 | 7.05 | 15418.01 | 133 | reducing | |

1) Calculated via http://web.expasy.org/compute_pi/

2) Due to the molecular weight of the dyes, shifts to slightly higher molecular weights are to be expected for 2D-DIGE 3) IL-2 should not be cleaved off the immunocytokine under reducing condition, as it is bound covalently via a linker to the Fc portion and therefore the heavy chain, antibody (½) and the antibody should not be present on a 2D-DIGE Nucleotide Sequence (cDNA, Incl. Leader)

"TAG" and "TGA" work as "stop codons" and therefore are not translated into the peptide sequence.

Light Chain (SEQ ID NO: 5):

| | |
|---|---|
| 1 | ~~ATG AAG TTG CCT GTT AGG CTG TTG GTG CTG ATG TTC TGG ATT CCT GCT TCC TTA AGC~~ GAC |
| 61 | GTG GTG ATG ACC CAG ACC CCC CTG TCC CTG CCC GTG ACC CCC GGC GAG CCC GCC TCC ATC |
| 121 | TCC TGC AGA TCT AGT CAG AGT CTT GTA CAC CGT AAT GGA AAC ACC TAT TTA CAT TGG TAC |
| 181 | CTG CAG AAG CCA GGC CAG TCT CCA AAG CTC CTG ATT CAC AAA GTT TCC AAC CGA TTT TCT |
| 241 | GGG GTC CCA GAC AGG TTC AGT GGC AGT GGA TCA GGG ACA GAT TTC ACA CTC AAG ATC AGC |
| 301 | AGA GTG GAG GCT GAG GAT CTG GGA GTT TAT TTC TGT TCT CAA AGT ACA CAT GTT CCT CCG |
| 361 | CTC ACG TTC GGT GCT GGG ACC AAG CTG GAG CTG AAA CGA ACT GTG GCT GCA CCA TCT GTC |
| 421 | TTC ATC TTC CCG CCA TCT GAT GAG CAG TTG AAA TCT GGA ACT GCC TCT GTT GTG TGC CTG |
| 481 | CTG AAT AAC TTC TAT CCC AGA GAG GCC AAA GTA CAG TGG AAG GTG GAT AAC GCC CTC CAA |
| 541 | TCG GGT AAC TCC CAG GAG AGT GTC ACA GAG CAG GAC AGC AAG GAC AGC ACC TAC AGC CTC |
| 601 | AGC AGC ACC CTG ACG CTG AGC AAA GCA GAC TAC GAG AAA CAC AAA GTC TAC GCC TGC GAA |
| 661 | GTC ACC CAT CAG GGC CTG AGC TCG CCC GTC ACA AAG AGC TTC AAC AGG GGA GAG TGT ~~TAG~~ |

Heavy Chain (incl. IL-2; SEQ ID NO: 6:)

| | |
|---|---|
| 1 | ~~ATG AAG TTG CCT GTT AGG CTG TTG GTG CTG ATG TTC TGG ATT CCT GCT TCC TTA ACC~~ GAG |
| 61 | GTG CAG CTG GTG CAG TCC GGC GCC GAG GTG GAG AAG CCC GGC GCC TCC GTG AAG ATC TCC |
| 121 | TGC AAG GCC TCC GGC TCC TCC TTC ACC GGC TAC AAC ATG AAC TGG GTG CGC CAG AAC ATC |
| 181 | GGC AAG TCC CTG GAG TGG ATC GGC GCC ATC GAC CCC TAC TAC GGC GGC ACC TCC TAC AAC |
| 241 | CAG AAG TTC AAG GGC CGC GCC ACC CTG ACC GTG GAC AAG TCC ACC TCC ACC GCC TAC ATG |
| 301 | CAC CTG AAG TCC CTG CGC TCC GAG GAC ACC GCC GTG TAC TAC TGC GTG TCC GGC ATG GAG |

-continued

| | |
|---|---|
| 361 | TAC TGG GGC CAG GGC ACC TCC GTG ACC GTG TCC TCC GCC TCC ACC AAG GGC CCA TCG GTC |
| 421 | TTC CCC CTG GCA CCC TCC TCC AAG AGC ACC TCT GGG GGC ACA GCG GCC CTG GGC TGC CTG |
| 481 | GTC AAG GAC TAC TTC CCC GAA CCG GTG ACG GTG TCG TGG AAC TCA GGC GCC CTG ACC AGC |
| 541 | GGC GTG CAC ACC TTC CCG GCT GTC CTA CAG TCC TCA GGA CTC TAC TCC CTC AGC AGC GTG |
| 601 | GTG ACC GTG CCC TCC AGC AGC TTG GGC ACC CAG ACC TAC ATC TGC AAC GTG AAT CAC AAG |
| 661 | CCC AGC AAC ACC AAG GTG GAC AAG AGA GTT GAG CCC AAA TCT TGT GAC AAA ACT CAC ACA |
| 721 | TGC CCA CCG TGC CCA GCA CCT GAA CTC CTG GGG GGA CCG TCA GTC TTC CTC TTC CCC CCA |
| 781 | AAA CCC AAG GAC ACC CTC ATG ATC TCC CGG ACC CCT GAG GTC ACA TGC GTG GTG GTG GAC |
| 841 | GTG AGC CAC GAA GAC CCT GAG GTC AAG TTC AAC TGG TAC GTG GAC GGC GTG GAG GTG CAT |
| 901 | AAT GCC AAG ACA AAG CCG CGG GAG GAG CAG TAC AAC AGC ACG TAC CGT GTG GTC AGC GTC |
| 961 | CTC ACC GTC CTG CAC CAG GAC TGG CTG AAT GGC AAG GAG TAC AAG TGC AAG GTC TCC AAC |
| 1021 | AAA GCC CTC CCA GCC CCC ATC GAG AAA ACC ATC TCC AAA GCC AAA GGG CAG CCC CGA GAA |
| 1081 | CCA CAG GTG TAC ACC CTG CCC CCA TCC CGG GAG GAG ATG ACC AAG AAC CAG GTC AGC CTG |
| 1141 | ACC TGC CTG GTC AAA GGC TTC TAT CCC AGC GAC ATC GCC GTG GAG TGG GAG AGC AAT GGG |
| 1201 | CAG CCG GAG AAC AAC TAC AAG ACC ACG CCT CCC GTG CTG GAC TCC GAC GGC TCC TTC TTC |
| 1261 | CTC TAT AGC AAG CTC ACC GTG GAC AAG AGC AGG TGG CAG CAG GGG AAC GTC TTC TCA TGC |
| 1321 | TCC GTG ATG CAT GAG GCT CTG CAC AAC CAC TAC ACG CAG AAG AGC CTC TCC CTG TCC CCG |
| 1381 | GGT AAA GCC CCA ACT TCA AGT TCT ACA AAG AAA ACA CAG CTG CAA CTG GAG CAT CTC CTG |
| 1441 | CTG GAT CTC CAG ATG ATT CTG AAT GGA ATT AAC AAC TAC AAG AAT CCC AAA CTC ACC AGG |
| 1501 | ATG CTC ACA TTC AAG TTC TAC ATG CCC AAG AAG GCC ACA GAG CTC AAA CAT CTC CAG TGT |
| 1561 | CTA GAG GAG GAA CTC AAA CCT CTG GAG GAA GTG CTA AAC CTC GCT CAG AGC AAA AAC TTC |
| 1621 | CAC TTA AGA CCT AGG GAC TTA ATC AGC AAT ATC AAC GTA ATA GTT CTG GAA CTA AAG GGA |
| 1681 | TCC GAA ACA ACA TTC ATG TGT GAA TAT GCT GAT GAG ACA GCA ACC ATT GTA GAA TTT CTG |
| 1741 | AAC AGA TGG ATT ACC TTT TGT CAA AGC ATC ATC TCA ACA CTA ACT ~~TGA~~ |

nucleotide 1 to 57 (striked out): leader sequence
nucleotide 1387 to 1385: IL-2 sequence
last nucleotide (striked out): stop codon Peptide Sequence (Incl. Signal Peptide)

The signal peptide is split off during post translational processing and is not part of the final recombinant protein anymore.

Light Chain

| | |
|---|---|
| | (SEQ ID NO: 7): |
| 1 | ~~M K L P V R L L V L M F W I P A S L S~~ D |
| 21 | V V M T Q T P L S L P V T P G E P A S I |
| 41 | S C R S S Q S L V H R N G N T Y L H W Y |
| 61 | L Q K P G Q S P K L L I H K V S N R F S |
| 81 | G V P D R F S G S G S G T D F T L K I S |
| 101 | R V E A E D L G V Y F C S Q S T H V P P |
| 121 | L T F G A G T K L E L K R T V A A P S V |
| 141 | F I F P P S D E Q L K S G T A S V V C L |

-continued

| | |
|---|---|
| 161 | L N N F Y P R E A K V Q W K V D N A L Q |
| 181 | S G N S Q E S V T E Q D S K D S T Y S L |
| 201 | S S T L T L S K A D Y E K H K V Y A C E |
| 221 | V T H Q G L S S P V T K S F N R G E C |

Heavy Chain

| | |
|---|---|
| | (incl. IL-2; SEQ ID NO: 8): |
| 1 | ~~M K L P V R L L V L M F W I P A S L S~~ E |
| 21 | V Q L V Q S G A E V E K P G A S V K I S |
| 41 | C K A S G S S F T G Y N M N W V R Q N I |
| 61 | G K S L E W I G A I D P Y Y G G T S Y N |
| 81 | Q K F K G R A T L T V D K S T S T A Y M |

-continued

| | |
|---|---|
| 101 | H L K S L R S E D T A V Y Y C V S G M E |
| 121 | Y W G Q G T S V T V S S A S T K G P S V |
| 141 | F P L A P S S K S T S G G T A A L G C L |
| 161 | V K D Y F P E P V T V S W N S G A L T S |
| 181 | G V H T F P A V L Q S S G L Y S L S S V |
| 201 | V T V P S S S L G T Q T Y I C N V N H K |
| 221 | P S N T K V D K R V E P K S C D K T H T |
| 241 | C P P C P A P E L L G G P S V F L F P P |
| 261 | K P K D T L M I S R T P E V T C V V V D |
| 281 | V S H E D P E V K F N W Y V D G V E V H |
| 301 | N A K T K P R E E Q Y N S T Y R V V S V |
| 321 | L T V L H Q D W L N G K E Y K C K V S N |
| 341 | K A L P A P I E K T I S K A K G Q P R E |
| 361 | P Q V Y T L P P S R E E M T K N Q V S L |
| 381 | T C L V K G F Y P S D I A V E W E S N G |
| 401 | Q P E N N Y K T T P P V L D S D G S F F |
| 421 | L Y S K L T V D K S R W Q Q G N V F S C |
| 441 | S V M H E A L H N H Y T Q K S L S L S P |
| 461 | G K A P T S S S T K K T Q L Q L E H L L |
| 481 | L D L Q M I L N G I N N Y K N P K L T R |
| 501 | M L T F K F Y M P K K A T E L K H L Q C |
| 521 | L E E E L K P L E E V L N L A Q S K N F |
| 541 | H L R P R D L I S N I N V I V L E L K G |
| 561 | S E T T F M C E Y A D E T A T I V E F L |
| 581 | N R W I T F C Q S I I S T L T |

amino acid 1 to 19 (striked out): leader sequence
amino acid 463 to 595: IL-2 sequence Two GMP compliant batches of the ch14.18/CHO (APN311) antibody have been produced. These two batches of the drug that have been produced are Lot T651204-A (containing 4.3 ml (4.6 mg/ml) antibody) and Lot T900310-A (containing 4.5 ml (4.5 mg/ml) antibody. The APN311 monoclonal antibody bulk preparation is manufactured as a concentrate for the preparation of IV infusions.

TABLE 7

| Composition of the final APN311 preparation | |
|---|---|
| Product Name | Mouse-human chimeric monoclonal anti-GD2 lgG1 antibody (ch 14.18/CHO; APN311) |
| Content | 4.25-4.75 mg/ml (the exact content per mL may slightly vary from lot to lot and is given on each vial) |
| Buffer | 20 mM histidine, 5% saccharose, 0.01% Tween 20, WFI |
| pH Value | 5.5-6.5 |
| Excipient | None |

Preparation Guide

The antibody must be prepared under sterile conditions. The appropriate volume of ch14.18/CHO antibody (APN311) should be withdrawn from the vials. It is recommended that the antibody solution is filtered (0.2 to 1.2 m) before injection into the patient either by using an in-line filter during infusion (as some centres do routinely) or by filtering the solution with a particle filter (e.g. filter Nr. MF1830, Impromediform, Germany). The volume of the antibody is added to an infusion bag containing NaCl 0.9% and 1% human serum albumin (HSA), e.g. 100 ml NaCl 0.9% and 5 ml human serum albumin 20%.

Calculation of the quantity of ch14.18/CHO (APN311) to be diluted

The amount of ch14.18/CHO (APN311) to be administered is calculated as follows: Dosage: 10 mg/m$^2$/day, day 8-17, as 24 h infusion.

Example calculation: If a patient has a body surface area (BSA) of 0.7, he/she needs 7 mg (10×0.7) per day, or 70 mg for ten treatment days (one cycle).

Example 2: CDC Assay Method

Principle for CDC (Complement Dependent Cytotoxicity)

Induction of tumor cell cytotoxicity of normal human serum or plasma in the presence of APN301 or APN311, or of patients' serum or plasma after infusion of one of these antibodies, to the GD2 antigen positive LAN-1 neuroblastoma cancer cell line (target cells) was determined in a $^{51}$Chromium release assay.

The target cells were incubated with $Na_2{}^{51}Cr(VI)O_4$, which permeates the cell membrane and binds to cytoplasmatic proteins in the reduced Cr-III-valent form, thereby not leaking out anymore of an intact cell. When these cells are lysed after incubation with serum or plasma and antibodies or patients' serum or plasma, radioactivity is released into the supernatant dependent on the lytic capacity in the tested samples.

Spontaneous background lysis and total lysis (maximally achievable cell lysis or maximal possible target cell lysis) by a surfactant were determined in each individual experiment. After subtracting spontaneous lysis, the lysis induced by the tested samples was calculated as % of total lysis.

Serum or Plasma Sampling:

Whole blood from normal human donors or from patients was sampled using heparinized vacutainer vials for plasma or serum clotting vials for serum. Vials were centrifuged at 2000 g for 20 minutes. The supernatant plasma or serum could be used immediately for the assay or stored at −20° C. (no thawing and re-freezing allowed).

Labeling of Target Cells with $^{51}$Cr:

LAN-1 cells were cultivated in RPMI 1640 with 10% heat inactivated FCS. The day preceding the assay they were transferred into fresh flasks and fresh medium.

The assay was carried out in a 96-well flat bottom cell culture plate, using 4×10$^4$ labeled cells per well with an activity of 800 nCi $^{51}$Cr per well.

The needed amount of cells was harvested from the culture flasks, the suspension centrifuged and re-suspended in 1 ml of PBS def. with 0.1% EDTA and 1% FCS. The calculated volume of the $^{51}$Cr solution was added, cells were incubated for 90 minutes at 37° C. and 5% $CO_2$ under gentle rotation of the tube.

Then the cell suspension was washed twice with cell culture medium to remove radioactivity from outside the cells. This medium contained additionally 100 U/ml penicillin G and 100 μg/ml streptomycin sulphate. The pellet of labeled cells after the washing steps was resuspended to the wanted concentration of 4×10$^5$ cells per ml.

Assay Procedure:

For the assessment of cytolytic capacity of antibodies, the following was pipetted:

50 μl of the samples (antibody dilutions)

100 μl 1:4 pre-diluted normal human serum or plasma

100 μl $^{51}$Cr labeled cell suspension ($4\times10^5$ per ml)

For the assessment of cytolytic capacity of patients' plasma or serum, the following was pipetted:

50 μl medium

100 μl 1:4 pre-diluted patients' plasma or serum

100 μl $^{51}$Cr labeled cell suspension ($4\times10^5$ per mL)

Assay plates for CDC were incubated in a $CO_2$ incubator at 37° C., 5% $CO_2$, for 4 hours, or when compared directly to a WBT, for 20 hours.

In addition, an aliquot of each blood sample is preincubated with ganglidiomab, a monoclonal mouse anti-ch14.18 antibody (anti-idiotypic antibody), and further processed as described above. It binds specifically to the antibody present in the blood sample after administration of the antibody to the patient. Thereby, the anti-idiotypic antibody inhibits the ability of the antibody to lyse the tumor target cells in combination with blood cells (WBT) and/or plasma components (CDC). Residual lysis can be defined as a non-antibody mediated effect.

Then the supernatants of each well are harvested using harvesting frames with absorption cartridges and a harvesting press (skatron). These cartridges soaked with the cell supernatants are transferred into counting vials of the gamma counter. Radioactivity, which is proportional to the release of 51-chromium after a damage of the labeled target cells, is measured from all samples and expressed in counts per minute (cpm). Results are calculated as % lysis subtracting the cpms of spontaneous lysis from all sample values and relating to the cpm of the maximally achievable lysis with a surfactant which is 100%.

100×(cpm sample minus cpm spontaneous lysis)=% lysis of samples cpm maximal lysis minus spontaneous lysis The above described CDC assay method has been used for the results as shown in FIGS. 1, 2, 3, 5, and FIG. 33 A.

A similar CDC assay method has been used for the results as shown in FIG. 7, however, calcein has been used as label for the LAN-1 cells instead of chromium.

Example 3: WBT Method

Principle for WBT (Whole Blood Test):

Induction of tumor cell cytotoxicity of normal human whole blood in the presence of APN301 or APN311, or of patients' whole blood after infusion of one of these antibodies, to the GD2 antigen positive LAN-1 neuroblastoma cancer cell line (target cells) was determined in a $^{51}$Chromium release assay.

The target cells were incubated with $Na_2{}^{51}Cr(VI)O_4$, which permeates the cell membrane and binds to cytoplasmatic proteins in the reduced Cr-III-valent form, thereby not leaking out of intact cells anymore. When these cells are lysed after incubation with whole blood and antibodies or patients' whole blood, radioactivity is released into the supernatant dependent on the lytic capacity in the tested samples.

Spontaneous background lysis and total lysis (maximally achievable lysis or maximal possible target cell lysis) by a surfactant were determined in each individual experiment. After subtracting spontaneous lysis, the lysis induced by the tested samples was calculated as % of total lysis.

Blood Sampling:

Whole blood from normal human donors or from patients was sampled using heparinized vacutainer vials.

Labeling of Target Cells with $^{51}$Cr:

LAN-1 cells were cultivated in RPMI 1640 with 10% heat inactivated FCS. The day preceding the assay they were transferred into fresh flasks and fresh medium.

The assay was carried out in a 96-well flat bottom cell culture plate, using $4\times10^4$ labeled cells per well with an activity of 800 nCi $^{51}$Cr per well.

The needed amount of cells was harvested from the culture flasks, the suspension centrifuged and re-suspended in 1 ml of PBS def. with 0.1% EDTA and 1% FCS. The calculated volume of the $^{51}$Cr solution was added, cells were incubated for 90 minutes at 37° C. and 5% $CO_2$ under gentle rotation of the tube.

Then the cell suspension was washed twice with cell culture medium to remove radioactivity from outside the cells. This medium contained additionally 100 U/ml penicillin G and 100 μg/ml streptomycin sulfate. The pellet of labeled cells after the washing steps was re-suspended to the wanted concentration of $4\times10^5$ cells per ml.

Assay Procedures:

For the assessment of cytolytic capacity of antibodies the following was pipetted:

50 μl of the samples (antibody dilutions)

100 μl 1:2 pre-diluted normal human whole blood

100 μl $^{51}$Cr labeled cell suspension ($4\times10^5$ per ml)

For the assessment of cytolytic capacity of patients' whole blood the following was pipetted:

50 μl medium

100 μl 1:2 pre-diluted patient's blood

100 μl $^{51}$Cr labeled cell suspension ($4\times10^5$ per ml)

Assay plates are incubated in a $CO_2$ incubator at 37° C., 5% $CO_2$, for 20 hours.

In addition, an aliquot of each blood sample is preincubated with ganglidiomab, a monoclonal mouse anti-ch14.18 antibody (anti-idiotypic antibody), and further processed as described above. It binds specifically to the antibody present in the blood sample after administration of the antibody to the patient. Thereby, the anti-idiotypic antibody inhibits the ability of the antibody to lyse the tumor target cells in combination with blood cells (WBT) and/or plasma components (CDC). Residual lysis can be defined as a non-antibody mediated effect.

Then the supernatants of each well are harvested using harvesting frames with absorption cartridges and a harvesting press (skatron). These cartridges soaked with the cell supernatants are transferred into counting vials of the gamma counter. Radioactivity which is proportional to the release of 51-chromium after a damage of the labelled target cells is measured from all samples and expressed in counts per minute (cpm). Results are calculated as % lysis subtracting the cpms of spontaneous lysis from all sample values and relating to the cpm of the maximally achievable lysis with a surfactant which is 100%.

100×(cpm sample minus cpm spontaneous lysis)=% lysis of samples cpm maximal lysis minus spontaneous lysis The above described WBT method has been used for the results as shown in FIGS. 1, 2, 3, 4, and FIG. 33 B.

Example 4: Patient Treatment with a Continuous Intravenous Infusion of a Preparation Comprising an Anti-GD2 Antibody In a compassionate use setting of the treatment with ch14.18/CHO (APN311) in 41 patients with relapsed or refractory neuroblastoma, a continuous infusion modality has been used in order to possibly reduce the pain always associated with anti-GD2 antibody immunotherapy, in conjunction with s.c. IL2 and isotretinoin. Clinical responses were determined by local physicians based on evaluations of metaiodobenzylguanidine scintigraphy (mIBG), magnetic resonance imaging (MRI) or X-ray computed tomography (CT), bone marrow histology (assessed by aspirate or trephine biopsy) and catecholamines.

mIBG: 31 out of 41 patients had disease detected in mIBG before immunotherapy.

5 of these 31 patients (16%) had a complete response (CR), 7 (23%) had a partial response (PR), 4 (13%) had stable disease (SD) and 13 (42%) had progressive disease (PD). 2 patients (6%) are not evaluable. For one of them no mIBG examinations after immunotherapy were available, the other patient had the remaining tumor removed by surgery before restaging assessments after immunotherapy were done.

Overall, in 12 out of 31 patients (39%) with detectable disease in mIBG before immunotherapy a response (CR or PR) was detected after immunotherapy.

Furthermore, in 3 out of the 13 patients with PD after completion of immunotherapy (23%), a PR was detected after the 3rd immunotherapy cycle.

MRI/CT: 13 out of 41 patients had detectable disease in MRI or CT in soft tissue before immunotherapy.

One additional patient with a positive MRI at baseline was not evaluable as the remaining tumor was completely resected before final restaging assessments. After 3 immunotherapy cycles this patient had SD.

5 of the 13 patients with detectable disease in MRI or CT before immunotherapy (38%) had a PR, 4 (31%) had SD and 3 (23%) had PD. Evaluation of one patient (8%) is pending.

Bone marrow: 19 out of 41 patients had detectable disease in bone marrow before immunotherapy. 4 of these 19 patients (21%) showed a response after immunotherapy in the respective tests. Additionally, in 6 patients (32%) a response was detected after 3 immunotherapy cycles. PD, however, was noticed in 4 of these patients in other examinations after 3 cycles, and in 2 of these patients at the end of the immunotherapy.

Catecholamines: 18 out of 41 patients had increased catecholamine levels (Vanillyl mandelic acid (VMA) and/or Homovanillic acid (HVA)) before immunotherapy. In 7 of these 18 patients (39%) normal catecholamine levels were detected after 3 cycles of immunotherapy and/or after completion of immunotherapy.

Figure 10:
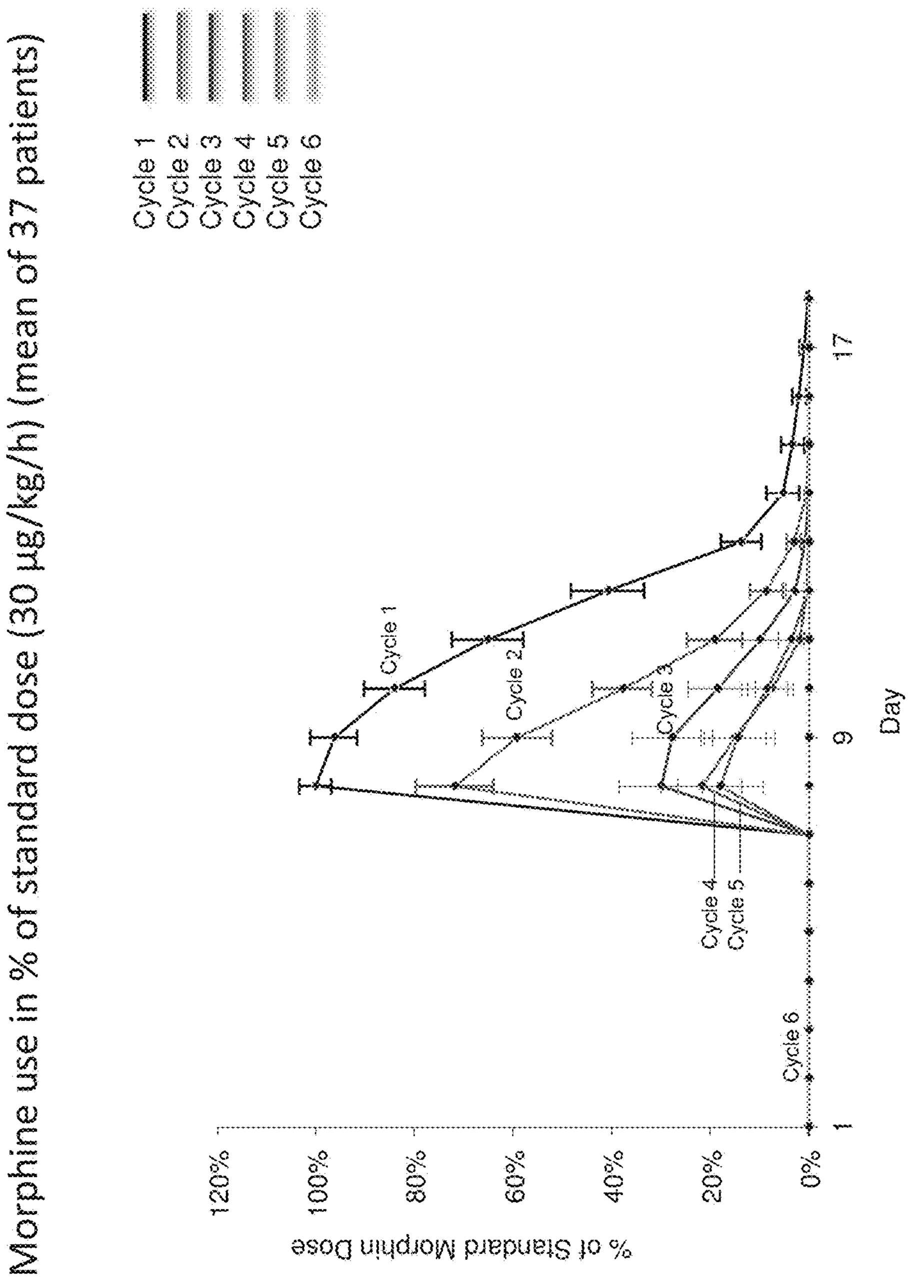
FIG. 10 shows the morphine use in % of the prescribed standard infusion rate (30 mcg/kg/h) during APN311 continuous infusions of 37 patients (mean values). Antibody infusions were always initiated on Day 8.

In addition to these marked response rates observed in the relapsed/refractory patients treated under a compassionate use setting by the continuous infusion modality, in all of these patients an impressive reduction of the pain side effect was noticed, allowing to substantially reduce or even completely avoid treatment with morphine:

The standard dose of i.v. morphine for this schedule is 30 μg/kg/h. In patients receiving ch14.18/CHO (APN311) continuous infusions, significantly less i.v. morphine was used compared to patients who receive ch14.18/CHO (APN311) bolus infusions. In many patients it was even possible to discontinue i.v. morphine completely and to treat pain with oral Gabapentin only. The morphine use during ch14.18/CHO (APN311) continuous infusions is displayed in FIG. 10 and Table 9. Antibody infusions were always initiated on Day 8. The actual morphine dose (mean of 37 patients) per overall treatment time (comprising all 6 treatment cycles) was 5.4 mg/kg compared to the prescribed morphine dose of 13.5 mg/kg of a previous phase I clinical study (0.9 mg/kg/day, infused over 8 h per day for 5 days per cycle, 3 cycles), and compared to 10 mg/kg of an ongoing phase III clinical study, both with non-continuous antibody infusion schedules (0.48 mg/kg/day on the first day and 0.38 mg/kg/day on the subsequent treatment days, infused over 8 h per day for 5 days per cycle, 5 cycles).

In addition, a Phase I/II study administering APN311 by continuous infusion combined with subcutaneous aldesleukin (IL2) in patients with primary refractory or relapsed neuroblastoma) has been set up to

- reduce the toxicity (pain) profile whilst maintaining immunomodulatory efficacy of ch14.18/CHO mAb (APN311) treatment in combination with a fixed dose of s.c. IL2.
- reduce the toxicity (pain) by establishing a continuous infusion scheme over 10 to 21 days at up to three dose levels (total doses: 100 $mg/m^2$-150 $mg/m^2$-200 $mg/m^2$).
- Improve patient compliance.
- Keep or even improve efficacy of immune therapy.

Preliminary results from this Phase I/II study show that the use of opioids, especially morphine, to control the massive incapacitating pain frequently occurring during the treatment with GD2 specific antibodies (including APN311) is significantly lower in these patients already during the first infusion cycles. From the $3^{rd}$ cycle onwards it may be even possible to completely refrain from the standard morphine administration since patients will not require it due to the increased tolerability of the medication due to the improved application scheme.

The significantly reduced doses of morphine cause less of the opioid treatment related adverse effects and therefore even allow an out-patient treatment setting, which in turn will positively influence the ability of the pediatric patients to follow the normal lifestyle of children, e.g. ability to play and attend school, etc.

TABLE 8

Blood samples analysed with a WBT shown in FIGS. 11 to 16.

| patient | day of treatment (within the treatment cycle) | cycle |
|---|---|---|
| MJ | 15 | I |
| | 8 | II |
| | 10 | II |
| NG | before | — |
| | 8 | I |
| | 10 | I |
| | 15 | I |
| JK | 8 | III |
| | 10 | III |
| | 15 | III |
| MM | 15 | III |
| GA | 8 | V |
| | 10 | V |
| CJJ | 10 | V |

Blood samples taken at the beginning (i.e. on the first day) of the treatment period with APN311 (corresponding to day 8 of the treatment cycle) were taken prior to the start of the APN311 treatment.

TABLE 9

| Morphine administration | | | | | | | | | | | | |
|---|---|---|---|---|---|---|---|---|---|---|---|---|
| | Cycle | Day 8 | Day 9 | Day 10 | Day 11 | Day 12 | Day 13 | Day 14 | Day 15 | Day 16 | Day 17 | dose per cycle in mg/kg |
| % of standard infus. rate | 1 | 100% | 96% | 84% | 65% | 41% | 14% | 5% | 3% | 2% | 1% | |
| infusion rate in mcg/kg/h | | 30.04 | 28.93 | 25.19 | 19.56 | 12.26 | 4.10 | 1.60 | 1.00 | 0.60 | 0.29 | |
| daily dose in mg/kg | | 0.72 | 0.69 | 0.60 | 0.47 | 0.29 | 0.10 | 0.04 | 0.02 | 0.01 | 0.01 | 2.97 |
| % of standard infus. rate | 2 | 72% | 59% | 38% | 19% | 9% | 3% | 0% | 0% | 0% | 0% | |
| infusion rate in mcg/kg/h | | 21.61 | 17.13 | 9.53 | 3.73 | 1.06 | 0.13 | 0.01 | 0 | 0 | 0 | |
| daily dose in mg/kg | | 0.52 | 0.41 | 0.23 | 0.09 | 0.03 | 0.00 | 0.00 | 0 | 0 | 0 | 1.28 |
| % of standard infus. rate | 3 | 30% | 28% | 18% | 10% | 3% | 1% | 0% | 0% | 0% | 0% | |
| infusion rate in mcg/kg/h | | 9.01 | 8.10 | 4.53 | 1.96 | 0.37 | 0.04 | 0 | 0 | 0 | 0 | |
| daily dose in mg/kg | | 0.22 | 0.19 | 0.11 | 0.05 | 0.01 | 0.00 | 0 | 0 | 0 | 0 | 0.58 |
| % of standard infus. rate | 4 | 22% | 15% | 8% | 2% | 0% | 0% | 0% | 0% | 0% | 0% | |
| infusion rate in mcg/kg/h | | 6.61 | 4.34 | 2.02 | 0.39 | 0 | 0 | 0 | 0 | 0 | 0 | |
| daily dose in mg/kg | | 0.16 | 0.10 | 0.05 | 0.01 | 0 | 0 | 0 | 0 | 0 | 0 | 0.32 |
| % of standard infus. rate | 5 | 18% | 14% | 8% | 4% | 0% | 0% | 0% | 0% | 0% | 0% | |
| infusion rate in mcg/kg/h | | 5.41 | 4.05 | 2.02 | 0.78 | 0 | 0 | 0 | 0 | 0 | 0 | |
| daily dose in mg/kg | | 0.13 | 0.10 | 0.05 | 0.02 | 0 | 0 | 0 | 0 | 0 | 0 | 0.29 |
| % of standard infus. rate | 6 | 0% | 0% | 0% | 0% | 0% | 0% | 0% | 0% | 0% | 0% | |
| infusion rate in mcg/kg/h | | 0 | 0 | 0 | 0 | 0 | 0 | 0 | 0 | 0 | 0 | |
| daily dose in mg/kg | | 0 | 0 | 0 | 0 | 0 | 0 | 0 | 0 | 0 | 0 | 0.00 |

Example 5: Patients Treated with APN311 without IL-2 (and without Other Cytokines) in Comparison to Data of Yu et al. 2010, NEJM (Cited Above)

The data underlying this example have been generated in the High Risk Neuroblastoma Study 1.5 of SIOP-Europe (SIOPEN), EudraCT number 2006-001489-17. Patients with high risk neuroblastoma after myeloablative therapy (MAT) and autologous stem cell rescue (ASCR), and as the case may be, also other treatments, such as radiation, other chemotherapies, surgery etc., have received up to 5 cycles of 20 $mg/m^2$/day ch14.18/CHO administered as an 8 hour i.v. infusion for 5 consecutive days (days 22 to 26 of the treatment cycle) in 28-day cycles. This corresponds to a total dose of 100 $mg/m^2$/cycle ch14.18/CHO. cis-RA has been administered orally twice a day in a dose of 160 $mg/m^2$/day on days 1 to 14 of the treatment cycle (in two equal doses per day, i.e. 2×80 $mg/m^2$). In one group, no IL-2 has been administered during a treatment cycle and during the overall treatment time. The patients of the other group received IL-2 at a dose of $6\times10^6$ $IU/m^2$/day on days 15 to 19 and 22 to 26 of a treatment cycle. The patients were treated in 6 treatment cycles, wherein treatment cycles 1 to 5 were as described above, and the sixth treatment cycle comprised the treatment period with isotretinoin only (no antibody and no IL-2 administered).

Event-free and overall survival was analyzed. EFS and OS were also analyzed in the subgroup of patients who presented as complete responders at the start of antibody treatment (no evidence of tumor by any applied examination). The EFS and OS data of this subgroup has been compared to the EFS and OS data of a treatment schedule with antibody, IL-2 and GM-CSF, and isotretinoin (cis-RA), as described in Yu et al. (NEJM 2010, cited above), and are included in Table 10.

The patients in Yu et al. have been treated with ch14.18/Sp2/0 given in a dose of 25 $mg/m^2$/day on four consecutive days, each dose of ch14.18/Sp2/0 is infused i.v. over 5.75 hours or 10 h (may have been extended to up to 20 h for anticipated toxicities). IL-2 is given every second cycle (e.g. cycle 2 and 4) as a continuous i.v. infusion over 4 days (96 h) in 3 $MIU/m^2$/day in week 1 of the treatment cycle and in 4.5 $MIU/m^2$/day in week 2 of the treatment cycle (i.e. 30 $MIU/m^2$/cycle). GM-CSF is given s.c. in a daily dose of 250 $mcg/m^2$ for 14 days (from Day 0 through 13). The overall treatment time comprises 5 treatment cycles. See also Tables 2, 3, and 4 for the respective treatment schedules. The EFS and OS Figures of Yu et al. that are depicted here in FIGS. 19 and 20 for comparison include only the complete responders of the above described treatment.

Therefore, only the subgroup of complete responders to the inventive treatment have been used for direct comparison.

TABLE 10

| 2-year event-free survival (EFS) and overall survival (OS) of complete responders (CR) of APN311-302 in comparison to Yu et al. (NEJM 2010, cited above) in percent | | |
|---|---|---|
| | 2 y EFS in % | 2 y OS in % |
| Subgroup of CR at start of randomization in APN311-302 study: APN311 + cis-RA | 70 | 81 |
| NEJM 2010: ch14.18 + IL2 + GM-CSF + cis-RA | 66 | 86 |
| NEJM 2010: cis RA only | 46 | 75 |

Figure 19:
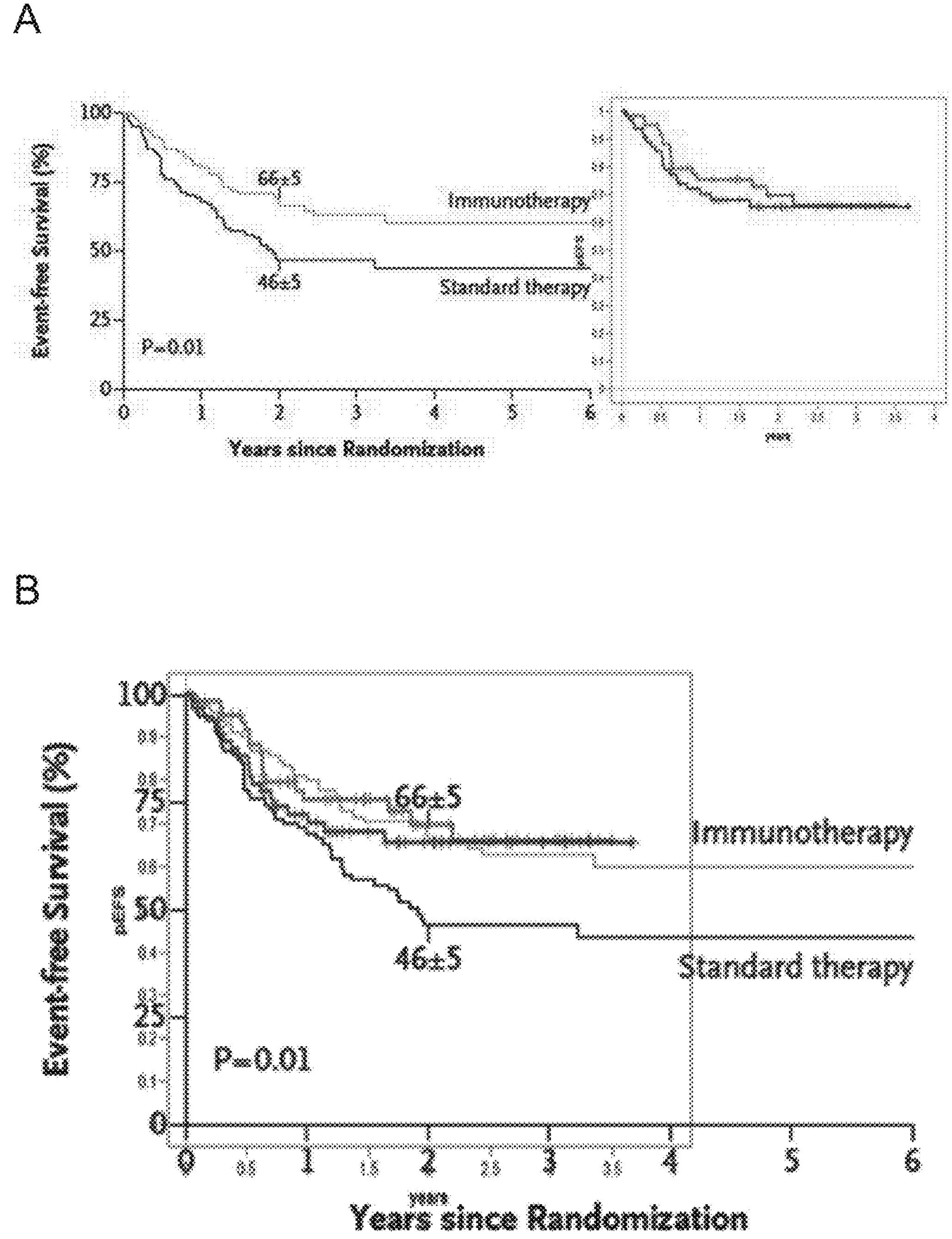
FIG. 19 shows the comparison of the EFS data (in percent over time) of 128 patients of Example 5 who had a complete response (CR) at start of treatment (FIG. 19 A, the diagram on the right) with the EFS data (in percent over time) of Yu et al. 2010, New England Journal of Medicine 363:1324-1334 (FIG. 19 A, the diagram on the left, also comprising data of complete responders).
Figure 20:
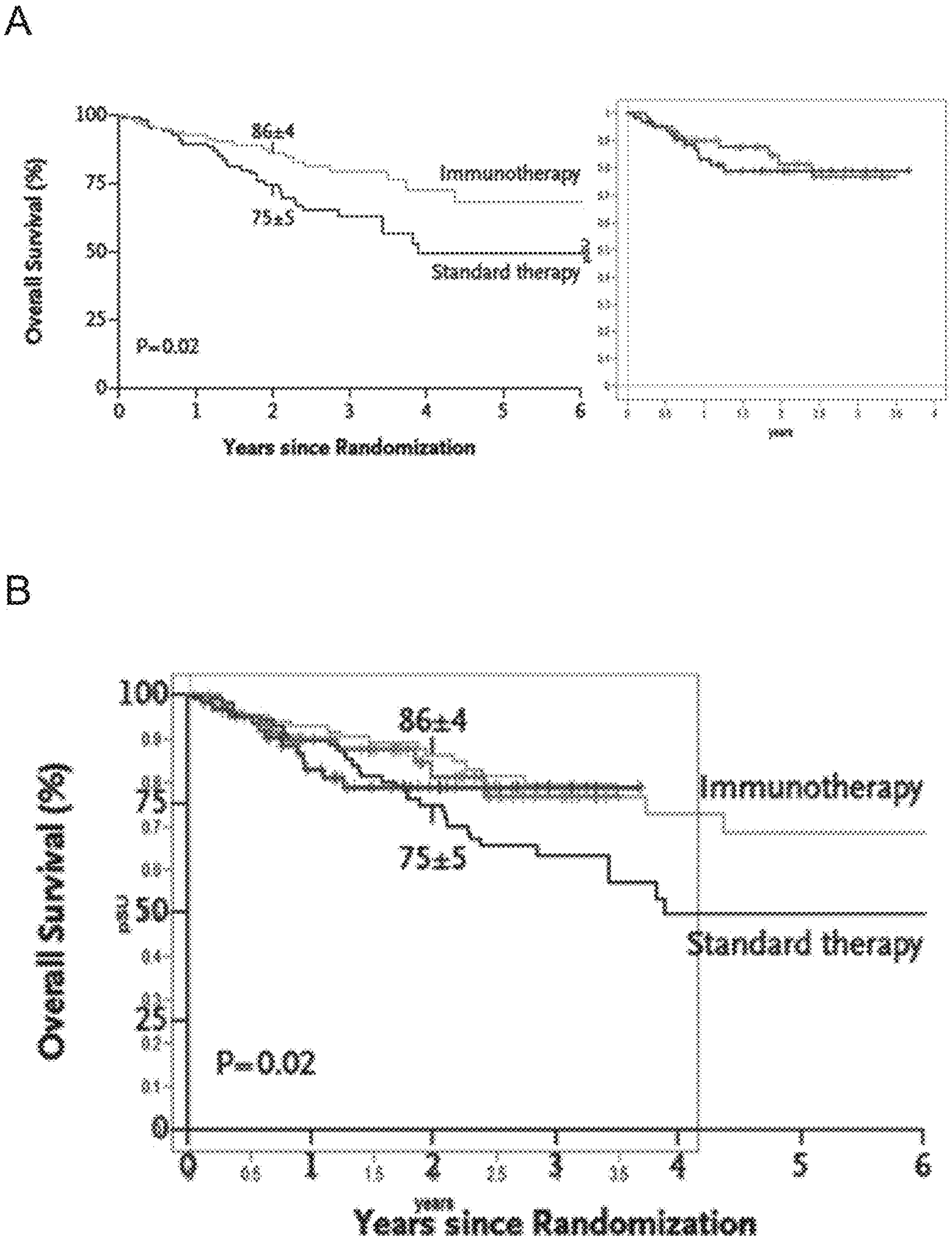
FIG. 20 shows the comparison of the OS data (in percent over time) of 128 patients of Example 5 who had a complete response (CR) at start of treatment (FIG. 20 A, the diagram on the right) with the OS data (in percent over time) of Yu et al. 2010 (FIG. 20 A, the diagram on the left).
Figure 23:
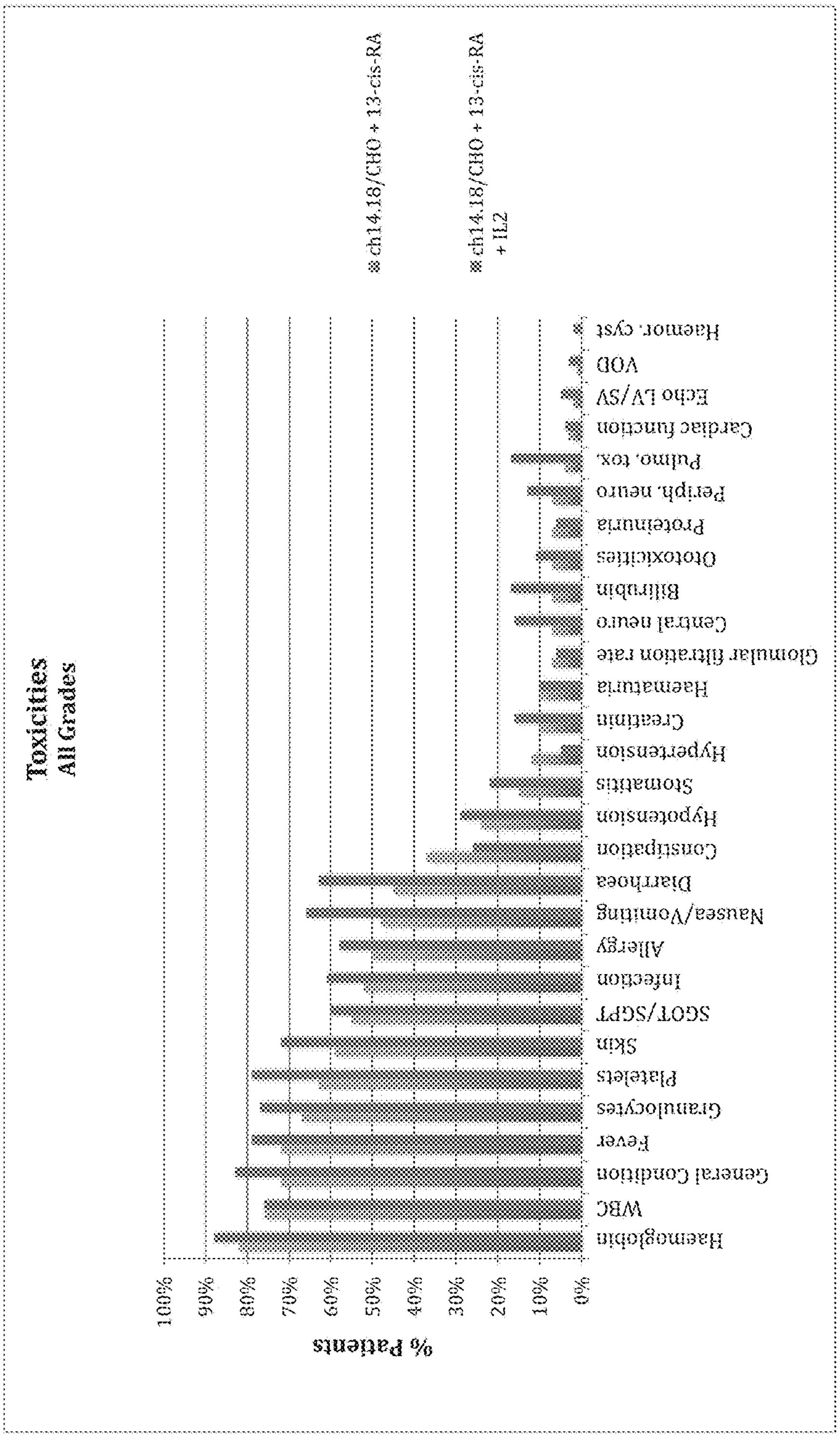
FIGS. 23 and 24 show the respective charts of toxicities (FIG. 23: all grades of toxicities.
Figure 24:
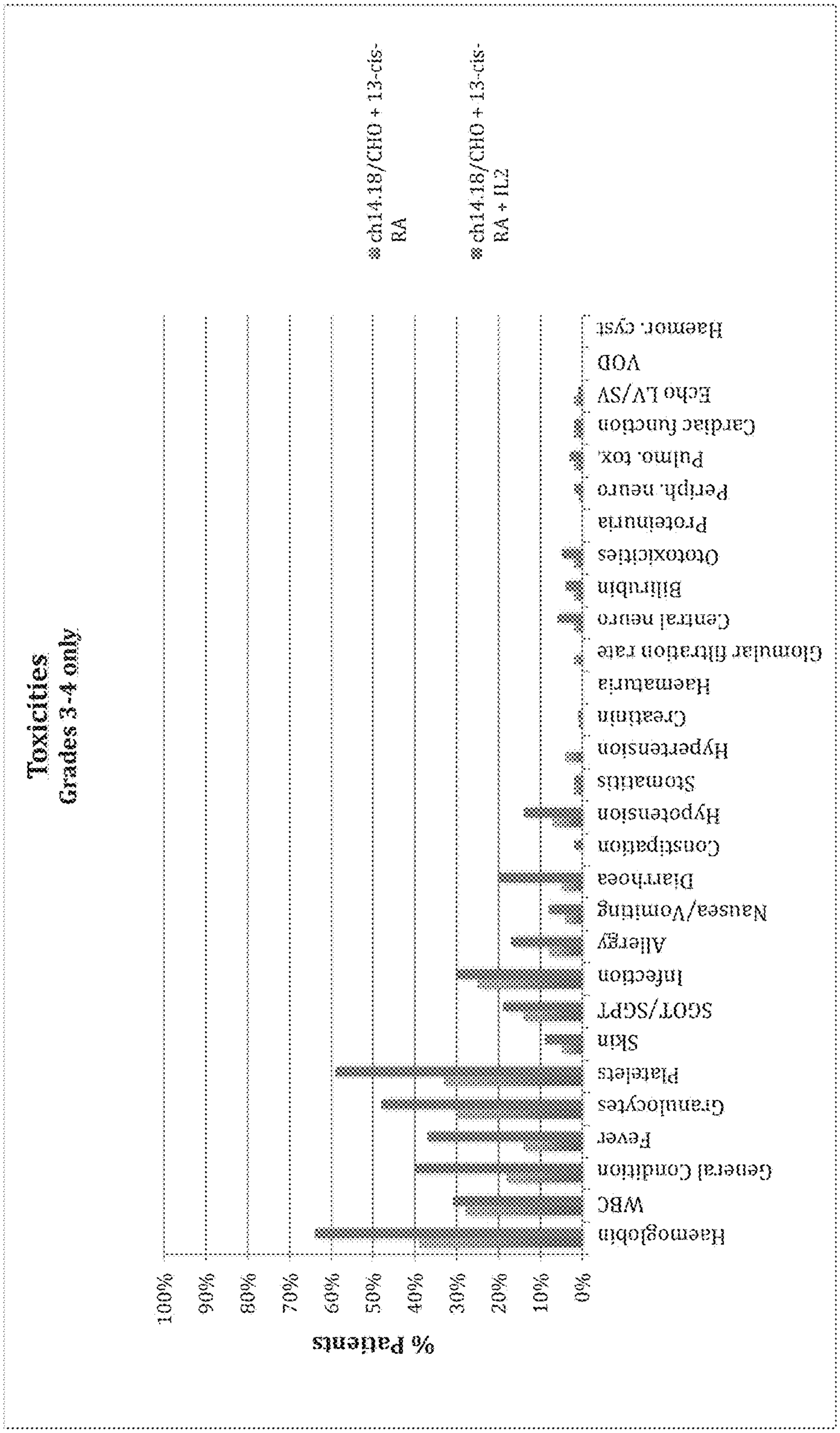
Figure 25:
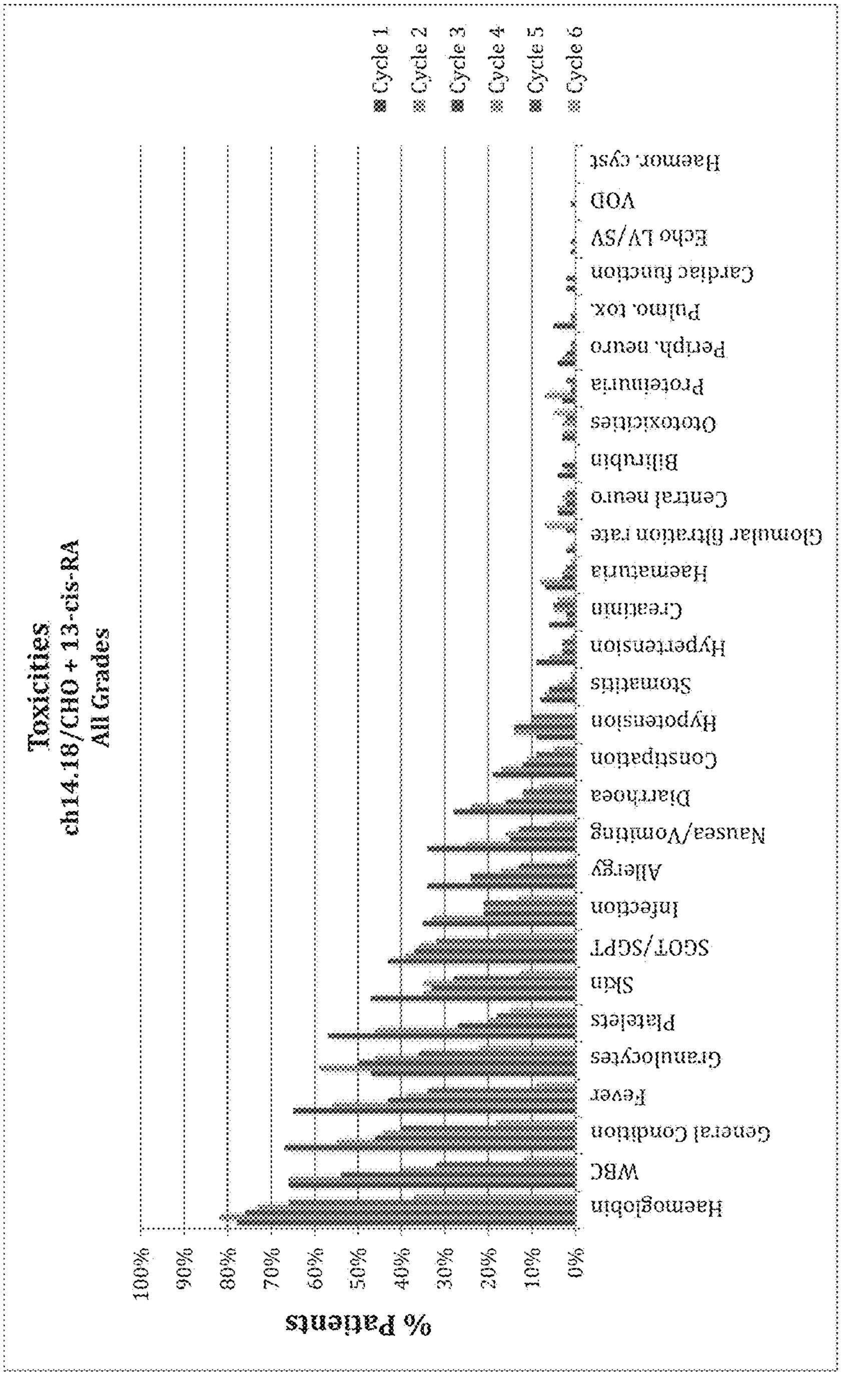
FIGS. 25 and 26 show charts of all grade toxicities per treatment cycle in percent of total evaluated patients treated in the respective schedules with IL-2 (FIG. 26) and without IL-2 (FIG. 25).
Figure 26:
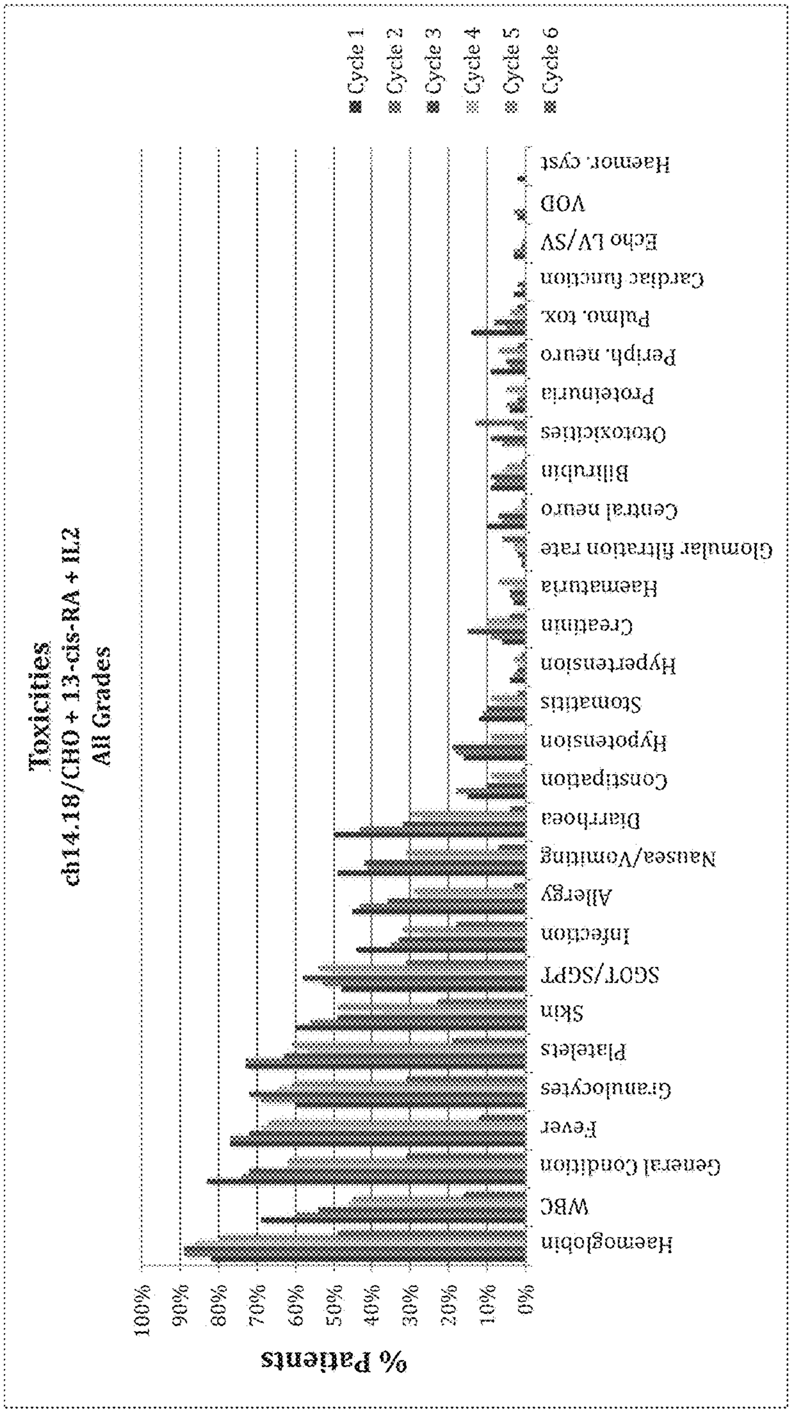
Figure 27:
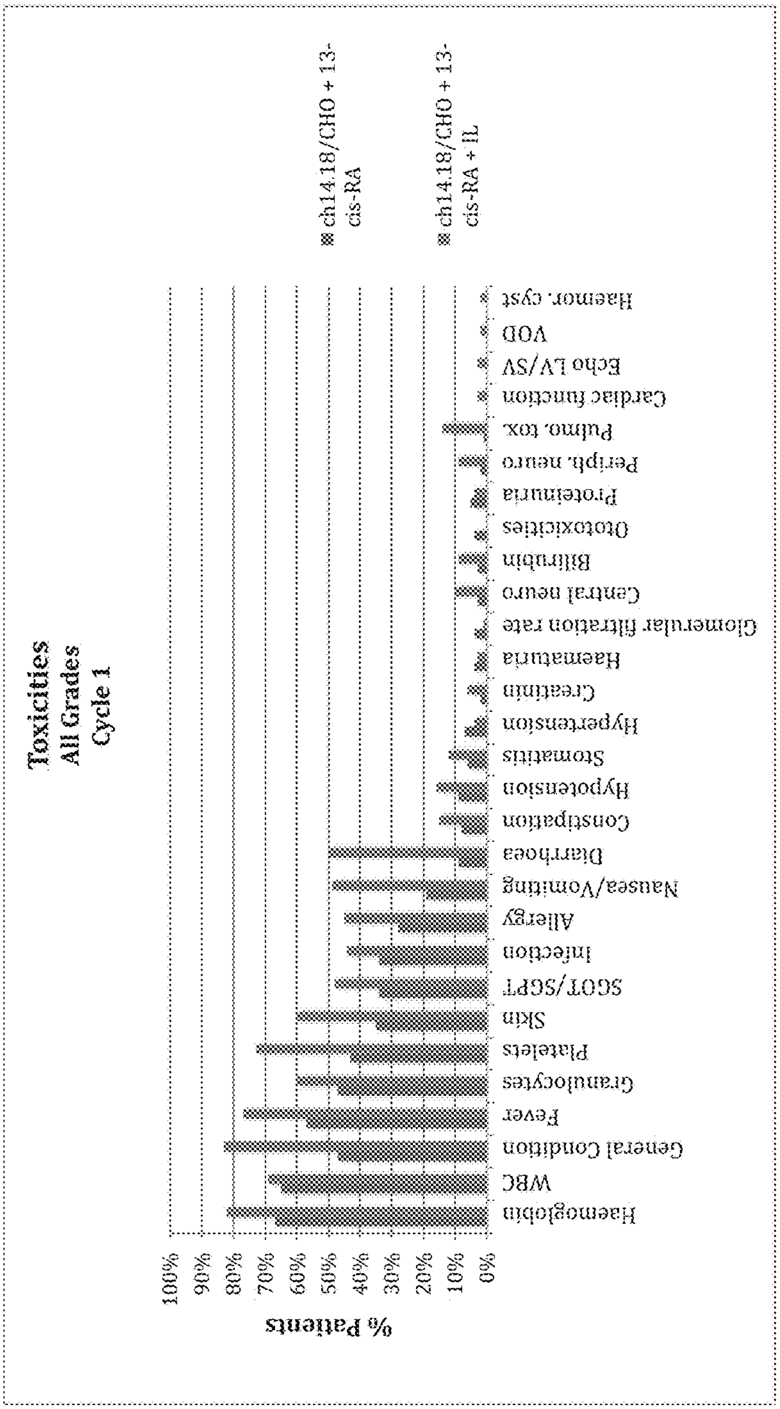
FIGS. 27 to 32 show charts of toxicities observed in the respective treatment cycle (FIG. 27: cycle 1, FIG. 28: cycle 2, FIG. 29: cycle 3, FIG. 30: cycle 4, FIG. 31: cycle 5, FIG. 32: cycle 6) in percent of total evaluated patients treated in the respective schedules with and without IL-2.
Figure 28:
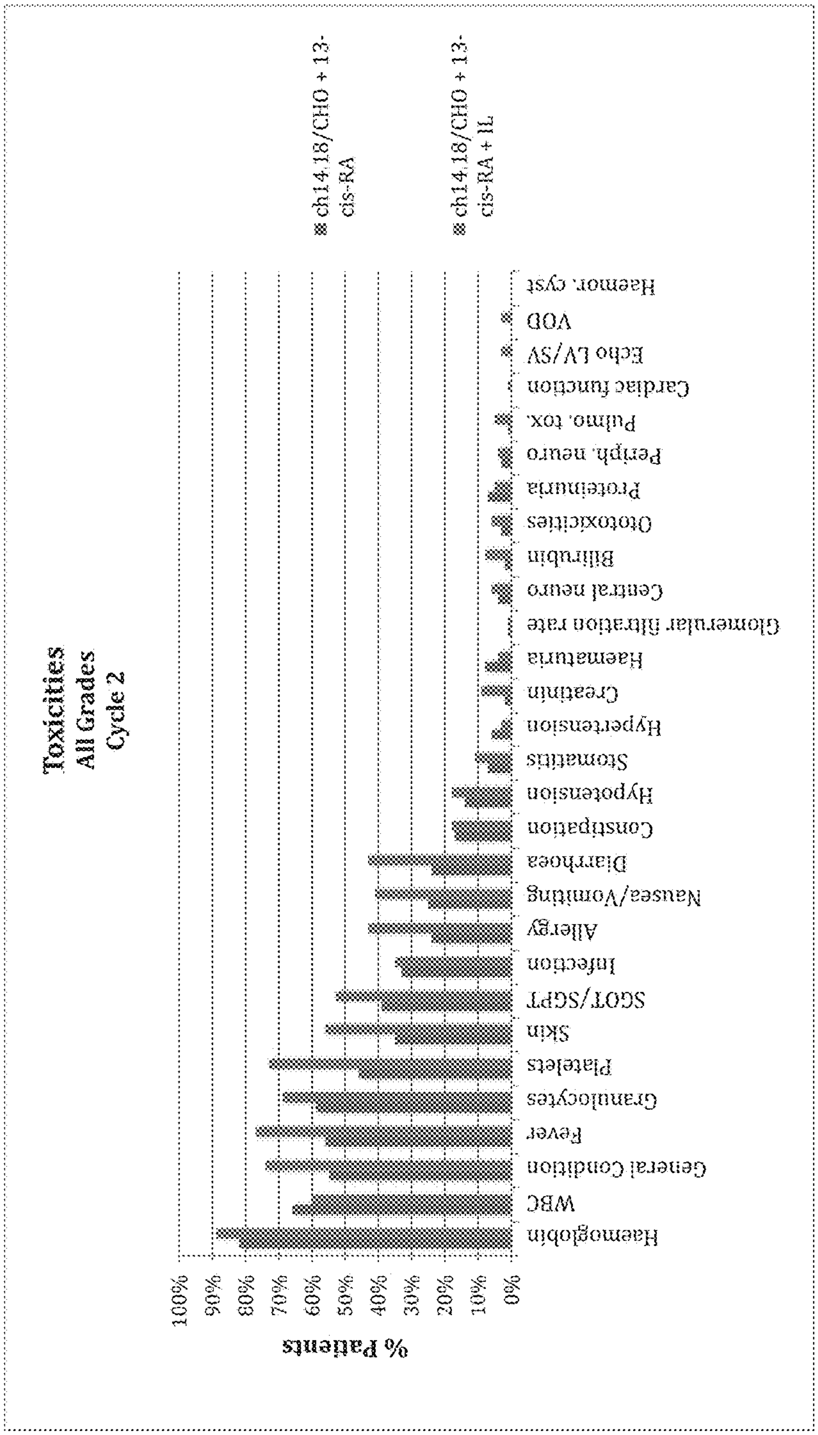
Figure 29:
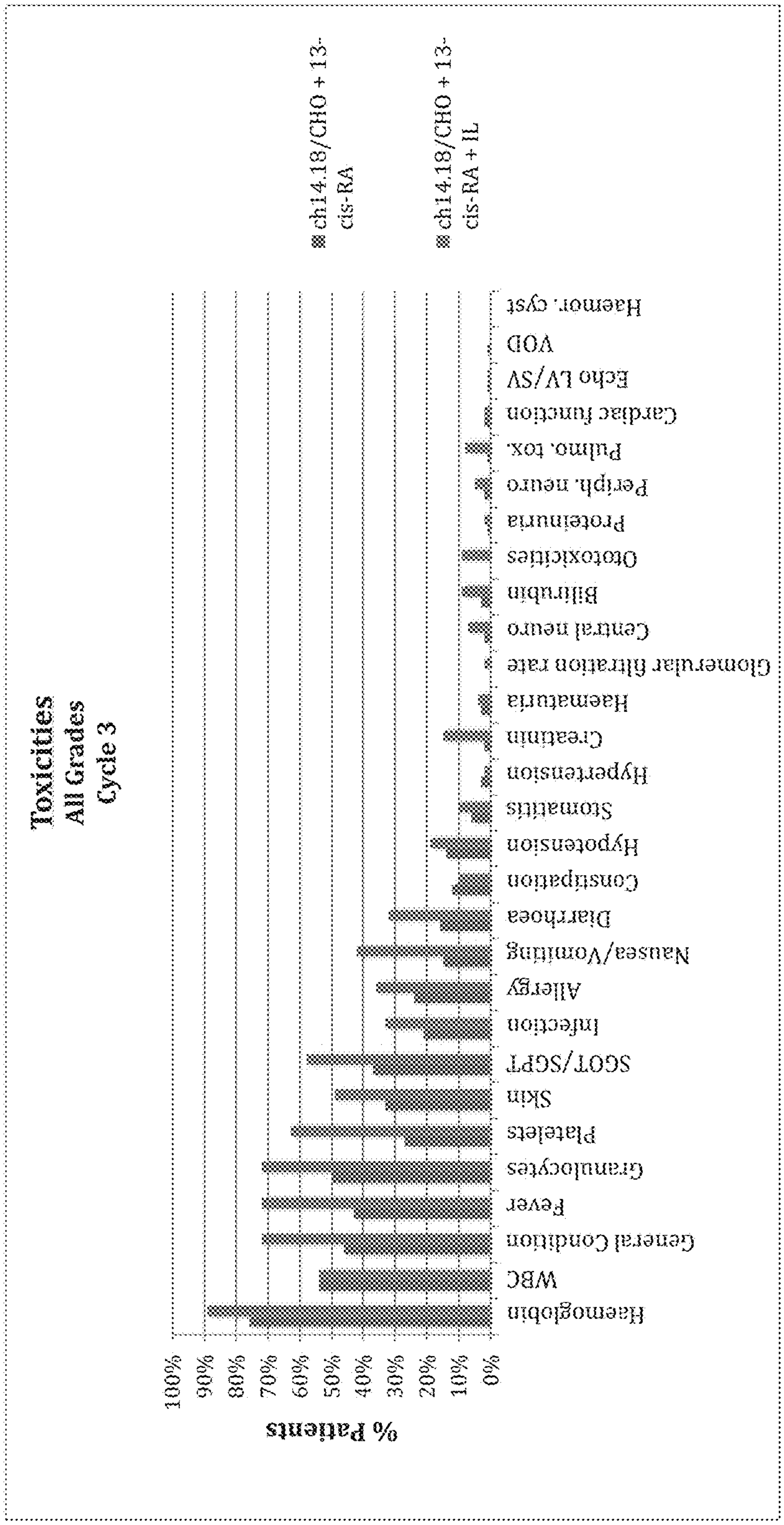
Figure 30:
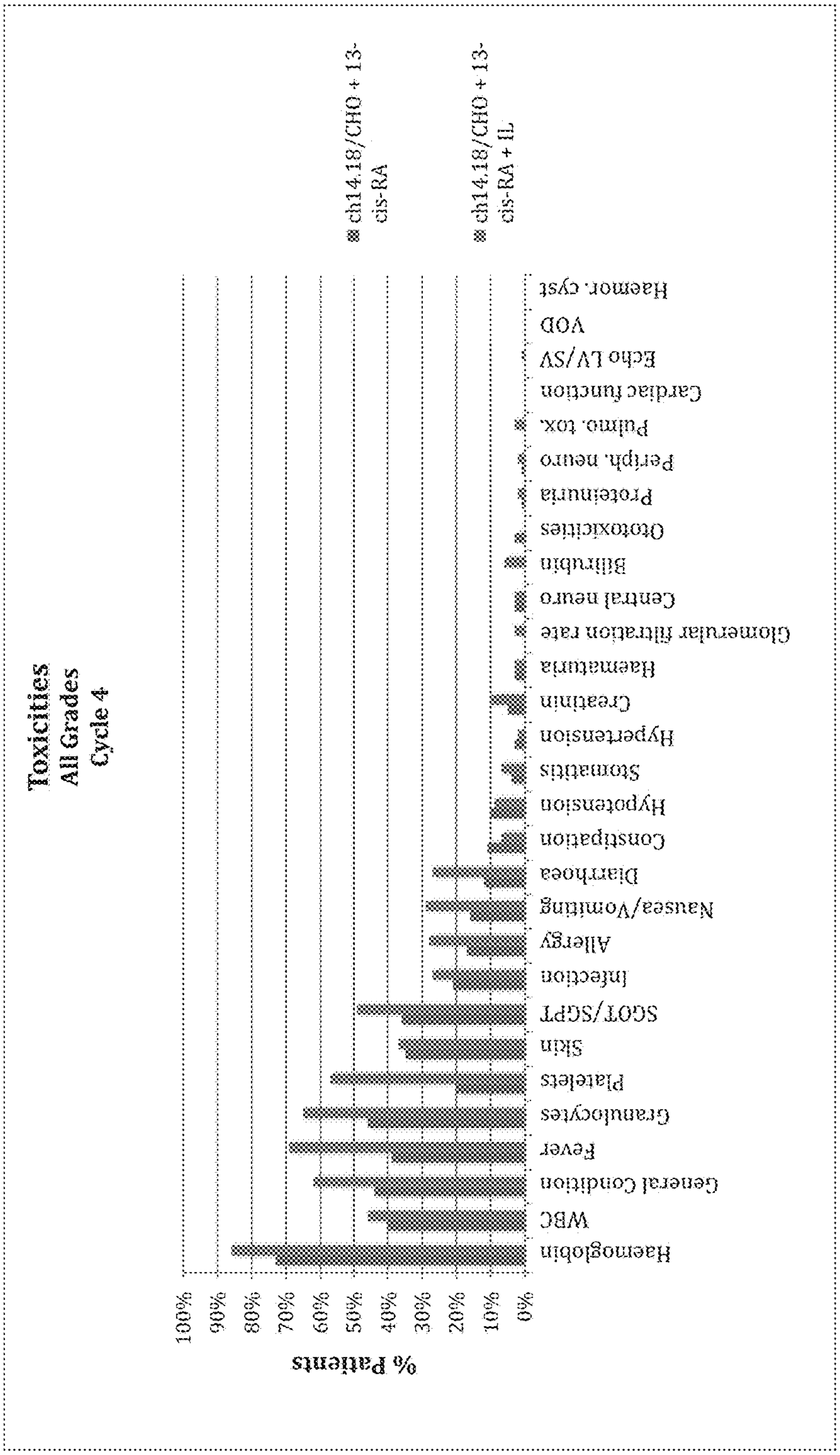
Figure 31:
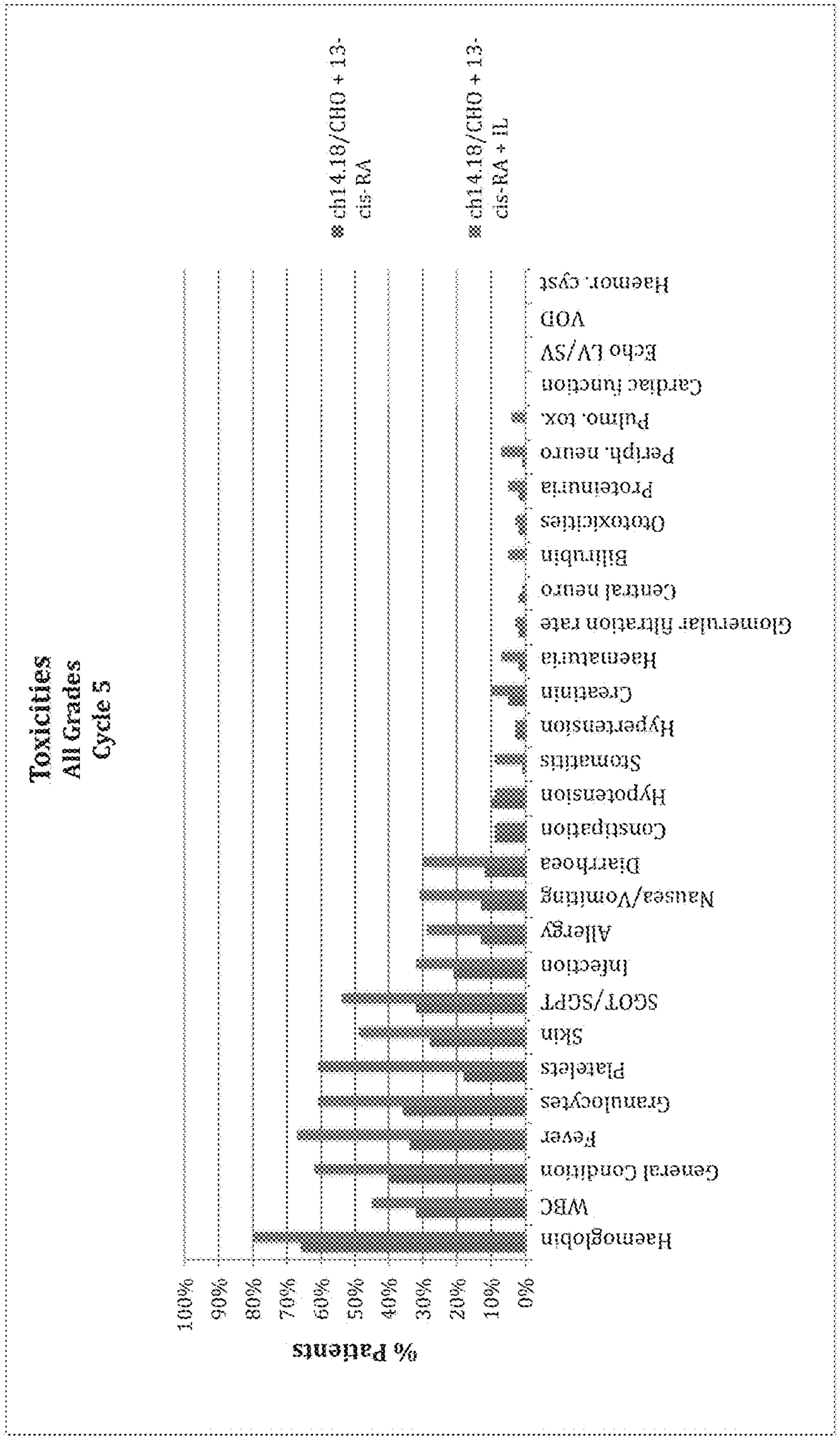
Figure 32:
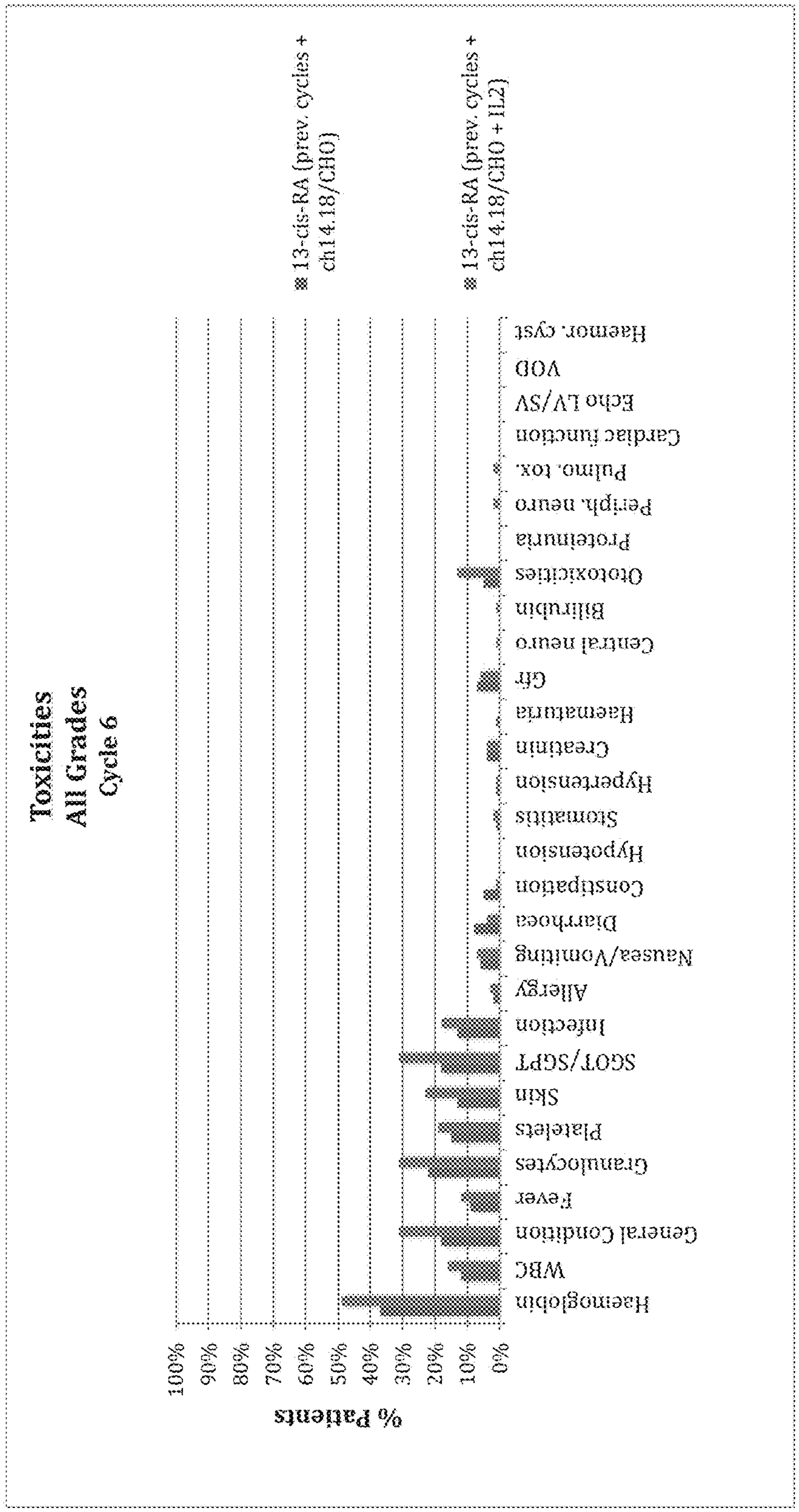

The results are also depicted in FIGS. 18, 19, and 20 (also in comparison to Yu et al.) and in FIGS. 21 to 32 (for further details about toxicities, i.e. adverse effects or side effects observed). According to these data, IL-2 does not contribute to the efficacy of anti-GD2 antibody treatment. However, concomitant IL-2 treatment substantially increases side effects and toxicities. APN311+cis-RA treatment of complete responders at start of immunotherapy leads to similar 2-year event-free and overall survival percentages and total survival curves than those found in the ch14.18/SP2-0+IL2+GM-CSF+cis-RA group of the NEJM 2010 study (Yu et al. 2010, cited above).

This suggests that the addition of both IL2 and GM-CSF are not needed to achieve the efficacy level of the combination treatment as described in NEJM 2010.

Both EFS and OS for APN311+cis-RA (complete responders at start of immunotherapy) compared to EFS and OS of patients of NEJM 2010 who received cis-RA only are improved (2y EFS: 70% versus 46%; 2y OS: 81% versus 75%; see also table 7). This indicates single agent efficacy of APN311.

In an overall assessment of risk and benefit, it is therefore concluded that APN311+cis-RA in complete responders at start of immunotherapy may be even superior to the 4-component immunotherapy as described in NEJM 2010, especially because of the substantially reduced side effect profile and reduced complexity of treatment due to omission of IL2 and GM-CSF, and because of the similar clinical efficacy in terms of EFS and OS.

Example 6: CDC and WBT Assay of a Neuroblastoma Patient Treated with Antibody A neuroblastoma patient has been treated with APN311 in a continuous infusion schedule, i.e. has received the antibody as a continuous infusion over 24 h per day for 10 consecutive days (on days 1-10 of a treatment cycle) in a dose of 10 mg/$m^2$/day for 6 subsequent cycles. Each treatment cycle comprised 35 days. During each treatment cycle and during the overall treatment time of said 6 subsequent cycles, the patient has only received antibody treatment and has not been treated with any cytokine nor retinoid.

Blood samples have been obtained from said patient at the indicated time points and have been analyzed in a CDC assay and WBT as described in Examples 2 and 3. The results are depicted in FIG. 33. FIG. 33 shows that antibody treatment without any cytokine treatment causes increased levels of tumor cell lysis. These levels of tumor cell lysis are comparable to the levels of patients treated with the antibody and IL-2 (one representative patient is shown in FIG. 34). The patient depicted in FIG. 34 has been treated with the same treatment schedule as the patient shown in FIG. 33, but has additionally been treated with s.c. IL-2 in a dose of $6\times10^6$ IU/$m^2$/day on days 1 to 5 and 8 to 12.

As can be seen especially in FIG. 33 B, an increased level of target cell lysis in the whole blood test (WBT) is maintained even for time periods within the overall treatment time, where the patient is not treated with the preparation comprising an anti-GD2 antibody, i.e. in the intervals between the treatment periods with the preparation comprising an anti-GD2 antibody.

The invention claimed is:

1. A method of treating neuroblastoma in a human patient comprising administering ch14.18 antibody in at least one treatment cycle, the at least one treatment cycle comprising at least one treatment period and optionally one or more days of no administration of the ch14.18 antibody to the patient between repeated treatment periods, wherein the treatment period is one or more consecutive days when the ch14.18 antibody is administered to the patient, the ch14.18 antibody being administered in a dose of or between 10 to 20 $mg/m^2$/day by intravenous infusion over 10 to 24 hours per day to the patient without administering IL-2 within the same one or more treatment cycles, wherein the ch14.18 antibody comprises a heavy chain and a light chain, the heavy chain having an amino acid sequence comprising SEQ ID NO:4 and the light chain having an amino acid sequence comprising SEQ ID NO:3, and wherein a neuroblastoma is treated in the patient.

2. The method of claim 1, further comprising treating the patient one or more times with a retinoid preceding, accompanying, and/or following administering of the ch14.18 antibody.

3. The method of claim 1, wherein the ch14.18 antibody is administered to the patient as a continuous intravenous infusion over 24 hours per day for one or more days.

4. The method of claim 1, wherein the ch14.18 antibody is administered to the patient for two or more treatment cycles.

5. The method of claim 1, wherein the patient is not treated with GM-CSF within the same one or more treatment cycles.

6. The method of claim 1, wherein the patient is not treated with a cytokine within the same one or more treatment cycles.

7. The method of claim 1, wherein the patient is not treated with IL-2, and/or GM-CSF, and/or a cytokine within the same one or more treatment cycles and/or within an overall treatment time that comprises one or more treatment cycles and optionally one or more days of no administration of the ch14.18 antibody to the patient between repeated treatment cycles.

8. The method of claim 1, wherein the neuroblastoma is high risk neuroblastoma, neuroblastoma stage 4, minimal residual neuroblastoma disease, relapsed neuroblastoma, and/or refractory neuroblastoma.

9. The method of claim 1, wherein the ch14.18 antibody administered to the patient is a CHO cell or SP2/0 cell produced antibody.

10. The method of claim 1, wherein the ch14.18 antibody is administered in a daily dose of 10 or 20 $mg/m^2$.

11. The method of claim 1, wherein the ch14.18 antibody is administered for 4, 10, 14, 15, or 21 consecutive days.

12. The method of claim 1, wherein the ch14.18 antibody is administered in a preparation further comprising sucrose, polysorbate 20, histidine, and hydrochloric acid.

13. The method of claim 12, wherein the preparation comprises 4.5 mg/mL ch14.18 antibody, 50 mg/mL sucrose, 0.1 mg/mL polysorbate 20, and 3.1 mg/mL histidine.

14. The method of claim 1, wherein the ch14.18 antibody is administered in a dose of 10 $mg/m^2$/day for 10 consecutive days for 1, 2, 3, 4, 5, 6 or more treatment cycles.

15. The method of claim 1, wherein the ch14.18 antibody administered to the patient is a CHO cell produced ch14.18 antibody.

16. The method of claim 1, wherein the ch14.18 antibody administered to the patient is a SP2/0 cell produced ch14.18 antibody.

17. The method of claim 1, wherein the administration of the ch14.18 antibody is accompanied by the administration of a reduced dose of morphine and/or one or more other analgesic.

18. The method of claim 1, wherein the ch14.18 antibody is administered in a dose of 60, 70, 75, 80, or 100 $mg/m^2$/treatment cycle.

19. The method of claim 1, wherein the patient is not treated with IL-2 within an overall treatment time that comprises one or more treatment cycles and optionally one or more days of no administration of the ch14.18 antibody to the patient between repeated treatment cycles.

20. The method of claim 1, wherein the ch14.18 antibody is a humanized ch14.18 antibody.

21. The method of claim 1, wherein the patient is not treated with IL-2, GM-CSF, or a cytokine within an overall treatment time that comprises one or more treatment cycles and optionally one or more days of no administration of the ch14.18 antibody to the patient between repeated treatment cycles.

* * * * *

SEQUENCE LISTING

```
<160> NUMBER OF SEQ ID NOS: 12

<210> SEQ ID NO 1
<211> LENGTH: 723
<212> TYPE: DNA
<213> ORGANISM: Artificial
<220> FEATURE:
<223> OTHER INFORMATION: artificial antibody chain

<400> SEQUENCE: 1

atggaagccc cagcgcagct tctcttcctc ctgctactct ggctcccaga taccactgga     60

gaaatagtga tgacgcagtc tccagccacc ctgtctgtgt ctccagggga aagagccacc    120

ctctcctgca gatctagtca gagtcttgta caccgtaatg gaaacaccta tttacattgg    180

tacctgcaga agccaggcca gtctccaaag ctcctgattc acaaagtttc caaccgattt    240

tctggggtcc cagacaggtt cagtggcagt ggatcaggga cagatttcac actcaagatc    300

agcagagtgg aggctgagga tctgggagtt tatttctgtt ctcaaagtac acatgttcct    360

ccgctcacgt tcggtgctgg gaccaagctg gagctgaaac gaactgtggc tgcaccatct    420

gtcttcatct tcccgccatc tgatgagcag ttgaaatctg gaactgcctc tgttgtgtgc    480

ctgctgaata acttctatcc cagagaggcc aaagtacagt ggaaggtgga taacgccctc    540

caatcgggta actcccagga gagtgtcaca gagcaggaca gcaaggacag cacctacagc    600

ctcagcagca ccctgacgct gagcaaagca gactacgaga aacacaaagt ctacgcctgc    660

gaagtcaccc atcagggcct gagctcgccc gtcacaaaga gcttcaacag gggagagtgt    720

tag                                                                  723

<210> SEQ ID NO 2
<211> LENGTH: 1389
<212> TYPE: DNA
<213> ORGANISM: Artificial
<220> FEATURE:
<223> OTHER INFORMATION: artificial antibody chain

<400> SEQUENCE: 2

atgggatgga cctggatctt tattttaatc ctgtcggtaa ctacaggtgt ccactctgag     60

gtccaactgc tgcagtctgg acctgagctg gagaagcctg gcgcttcagt gatgatatcc    120

tgcaaggctt ctggttcctc attcactggc tacaacatga actgggtgag gcagaacatt    180
```

```
ggaaagagcc ttgaatggat tggagctatt gatccttact atggtggaac tagctacaac    240

cagaagttca agggcagggc cacattgact gtagacaaat cgtccagcac agcctacatg    300

cacctcaaga gcctgacatc tgaggactct gcagtctatt actgtgtaag cggaatggag    360

tactggggtc aaggaacctc agtcaccgtc tcctcagcct ccaccaaggg cccatcggtc    420

ttccccctgg caccctcctc caagagcacc tctgggggca cagcggccct gggctgcctg    480

gtcaaggact acttccccga accggtgacg gtgtcgtgga actcaggcgc cctgaccagc    540

ggcgtgcaca ccttcccggc tgtcctacag tcctcaggac tctactccct cagcagcgtg    600

gtgaccgtgc cctccagcag cttgggcacc cagacctaca tctgcaacgt gaatcacaag    660

cccagcaaca ccaaggtgga caagagagtt gagcccaaat cttgtgacaa aactcacaca    720

tgcccaccgt gcccagcacc tgaactcctg gggggaccgt cagtcttcct cttcccccca    780

aaacccaagg acaccctcat gatctcccgg acccctgagg tcacatgcgt ggtggtggac    840

gtgagccacg aagaccctga ggtcaagttc aactggtacg tggacggcgt ggaggtgcat    900

aatgccaaga caaagccgcg ggaggagcag tacaacagca cgtaccgtgt ggtcagcgtc    960

ctcaccgtcc tgcaccagga ctggctgaat ggcaaggagt acaagtgcaa ggtctccaac   1020

aaagccctcc cagcccccat cgagaaaacc atctccaaag ccaaagggca gccccgagaa   1080

ccacaggtgt acaccctgcc cccatcccgg gaggagatga ccaagaacca ggtcagcctg   1140

acctgcctgg tcaaaggctt ctatcccagc gacatcgccg tggagtggga gagcaatggg   1200

cagccggaga acaactacaa gaccacgcct cccgtgctgg actccgacgg ctccttcttc   1260

ctctatagca agctcaccgt ggacaagagc aggtggcagc aggggaacgt cttctcatgc   1320

tccgtgatgc atgaggctct gcacaaccac tacacgcaga agagcctctc cctgtccccg   1380

ggtaaatga                                                            1389
```

```
<210> SEQ ID NO 3
<211> LENGTH: 240
<212> TYPE: PRT
<213> ORGANISM: Artificial
<220> FEATURE:
<223> OTHER INFORMATION: artificial antibody chain

<400> SEQUENCE: 3

Met Glu Ala Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ser Ser Gln Ser
        35                  40                  45

Leu Val His Arg Asn Gly Asn Thr Tyr Leu His Trp Tyr Leu Gln Lys
    50                  55                  60

Pro Gly Gln Ser Pro Lys Leu Leu Ile His Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Leu Gly Val Tyr Phe
            100                 105                 110

Cys Ser Gln Ser Thr His Val Pro Pro Leu Thr Phe Gly Ala Gly Thr
        115                 120                 125

Lys Leu Glu Leu Lys Arg Thr Val Ala Ala Pro Ser Val Phe Ile Phe
    130                 135                 140
```

```
Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240


<210> SEQ ID NO 4
<211> LENGTH: 462
<212> TYPE: PRT
<213> ORGANISM: Artificial
<220> FEATURE:
<223> OTHER INFORMATION: artificial antibody chain

<400> SEQUENCE: 4

Met Gly Trp Thr Trp Ile Phe Ile Leu Ile Leu Ser Val Thr Thr Gly
1               5                   10                  15

Val His Ser Glu Val Gln Leu Leu Gln Ser Gly Pro Glu Leu Glu Lys
            20                  25                  30

Pro Gly Ala Ser Val Met Ile Ser Cys Lys Ala Ser Gly Ser Ser Phe
        35                  40                  45

Thr Gly Tyr Asn Met Asn Trp Val Arg Gln Asn Ile Gly Lys Ser Leu
    50                  55                  60

Glu Trp Ile Gly Ala Ile Asp Pro Tyr Tyr Gly Gly Thr Ser Tyr Asn
65                  70                  75                  80

Gln Lys Phe Lys Gly Arg Ala Thr Leu Thr Val Asp Lys Ser Ser Ser
                85                  90                  95

Thr Ala Tyr Met His Leu Lys Ser Leu Thr Ser Glu Asp Ser Ala Val
            100                 105                 110

Tyr Tyr Cys Val Ser Gly Met Glu Tyr Trp Gly Gln Gly Thr Ser Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270
```

```
Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460
```

<210> SEQ ID NO 5
<211> LENGTH: 720
<212> TYPE: DNA
<213> ORGANISM: Artificial
<220> FEATURE:
<223> OTHER INFORMATION: artificial antibody chain

<400> SEQUENCE: 5

```
atgaagttgc ctgttaggct gttggtgctg atgttctgga ttcctgcttc cttaagcgac     60

gtggtgatga cccagacccc cctgtccctg cccgtgaccc ccggcgagcc cgcctccatc    120

tcctgcagat ctagtcagag tcttgtacac cgtaatggaa acacctattt acattggtac    180

ctgcagaagc caggccagtc tccaaagctc ctgattcaca aagtttccaa ccgattttct    240

ggggtcccag acaggttcag tggcagtgga tcagggacag atttcacact caagatcagc    300

agagtggagg ctgaggatct gggagtttat ttctgttctc aaagtacaca tgttcctccg    360

ctcacgttcg gtgctgggac caagctggag ctgaaacgaa ctgtggctgc accatctgtc    420

ttcatcttcc cgccatctga tgagcagttg aaatctggaa ctgcctctgt tgtgtgcctg    480

ctgaataact tctatcccag agaggccaaa gtacagtgga aggtggataa cgccctccaa    540

tcgggtaact cccaggagag tgtcacagag caggacagca aggacagcac ctacagcctc    600

agcagcaccc tgacgctgag caaagcagac tacgagaaac acaaagtcta cgcctgcgaa    660

gtcacccatc agggcctgag ctcgcccgtc acaaagagct tcaacagggg agagtgttag    720
```

<210> SEQ ID NO 6
<211> LENGTH: 1788
<212> TYPE: DNA
<213> ORGANISM: Artificial
<220> FEATURE:
<223> OTHER INFORMATION: artificial antibody chain -continued

<400> SEQUENCE: 6

```
atgaagttgc ctgttaggct gttggtgctg atgttctgga ttcctgcttc cttaagcgag     60
gtgcagctgg tgcagtccgg cgccgaggtg gagaagcccg gcgcctccgt gaagatctcc    120
tgcaaggcct ccggctcctc cttcaccggc tacaacatga actgggtgcg ccagaacatc    180
ggcaagtccc tggagtggat cggcgccatc gacccctact acggcggcac ctcctacaac    240
cagaagttca agggccgcgc caccctgacc gtggacaagt ccacctccac cgcctacatg    300
cacctgaagt ccctgcgctc cgaggacacc gccgtgtact actgcgtgtc cggcatggag    360
tactggggcc agggcacctc cgtgaccgtg tcctccgcct ccaccaaggg cccatcggtc    420
ttccccctgg caccctcctc caagagcacc tctgggggca cagcggccct gggctgcctg    480
gtcaaggact acttccccga accggtgacg gtgtcgtgga actcaggcgc cctgaccagc    540
ggcgtgcaca ccttcccggc tgtcctacag tcctcaggac tctactccct cagcagcgtg    600
gtgaccgtgc cctccagcag cttgggcacc cagacctaca tctgcaacgt gaatcacaag    660
cccagcaaca ccaaggtgga caagagagtt gagcccaaat cttgtgacaa aactcacaca    720
tgcccaccgt gcccagcacc tgaactcctg gggggaccgt cagtcttcct cttcccccca    780
aaacccaagg acaccctcat gatctcccgg acccctgagg tcacatgcgt ggtggtggac    840
gtgagccacg aagaccctga ggtcaagttc aactggtacg tggacggcgt ggaggtgcat    900
aatgccaaga caaagccgcg ggaggagcag tacaacagca cgtaccgtgt ggtcagcgtc    960
ctcaccgtcc tgcaccagga ctggctgaat ggcaaggagt acaagtgcaa ggtctccaac   1020
aaagccctcc cagcccccat cgagaaaacc atctccaaag ccaaagggca gccccgagaa   1080
ccacaggtgt acaccctgcc cccatcccgg gaggagatga ccaagaacca ggtcagcctg   1140
acctgcctgg tcaaaggctt ctatcccagc gacatcgccg tggagtggga gagcaatggg   1200
cagccggaga acaactacaa gaccacgcct cccgtgctgg actccgacgg ctccttcttc   1260
ctctatagca agctcaccgt ggacaagagc aggtggcagc aggggaacgt cttctcatgc   1320
tccgtgatgc atgaggctct gcacaaccac tacacgcaga agagcctctc cctgtccccg   1380
ggtaaagccc caacttcaag ttctacaaag aaaacacagc tgcaactgga gcatctcctg   1440
ctggatctcc agatgattct gaatggaatt aacaactaca agaatcccaa actcaccagg   1500
atgctcacat tcaagttcta catgcccaag aaggccacag agctcaaaca tctccagtgt   1560
ctagaggagg aactcaaacc tctggaggaa gtgctaaacc tcgctcagag caaaaacttc   1620
cacttaagac ctagggactt aatcagcaat atcaacgtaa tagttctgga actaaaggga   1680
tccgaaacaa cattcatgtg tgaatatgct gatgagacag caaccattgt agaatttctg   1740
aacagatgga ttaccttttg tcaaagcatc atctcaacac taacttga                1788
```

<210> SEQ ID NO 7
<211> LENGTH: 239
<212> TYPE: PRT
<213> ORGANISM: Artificial
<220> FEATURE:
<223> OTHER INFORMATION: artificial antibody chain

<400> SEQUENCE: 7

```
Met Lys Leu Pro Val Arg Leu Leu Val Leu Met Phe Trp Ile Pro Ala
1               5                   10                  15

Ser Leu Ser Asp Val Val Met Thr Gln Thr Pro Leu Ser Leu Pro Val
            20                  25                  30

Thr Pro Gly Glu Pro Ala Ser Ile Ser Cys Arg Ser Ser Gln Ser Leu
```

-continued

```
        35                  40                  45

Val His Arg Asn Gly Asn Thr Tyr Leu His Trp Tyr Leu Gln Lys Pro
    50                  55                  60

Gly Gln Ser Pro Lys Leu Leu Ile His Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Pro Leu Thr Phe Gly Ala Gly Thr Lys
        115                 120                 125

Leu Glu Leu Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235


<210> SEQ ID NO 8
<211> LENGTH: 595
<212> TYPE: PRT
<213> ORGANISM: Artificial
<220> FEATURE:
<223> OTHER INFORMATION: artificial antibody chain

<400> SEQUENCE: 8

Met Lys Leu Pro Val Arg Leu Leu Val Leu Met Phe Trp Ile Pro Ala
1               5                   10                  15

Ser Leu Ser Glu Val Gln Leu Val Gln Ser Gly Ala Glu Val Glu Lys
            20                  25                  30

Pro Gly Ala Ser Val Lys Ile Ser Cys Lys Ala Ser Gly Ser Ser Phe
        35                  40                  45

Thr Gly Tyr Asn Met Asn Trp Val Arg Gln Asn Ile Gly Lys Ser Leu
    50                  55                  60

Glu Trp Ile Gly Ala Ile Asp Pro Tyr Tyr Gly Gly Thr Ser Tyr Asn
65                  70                  75                  80

Gln Lys Phe Lys Gly Arg Ala Thr Leu Thr Val Asp Lys Ser Thr Ser
                85                  90                  95

Thr Ala Tyr Met His Leu Lys Ser Leu Arg Ser Glu Asp Thr Ala Val
            100                 105                 110

Tyr Tyr Cys Val Ser Gly Met Glu Tyr Trp Gly Gln Gly Thr Ser Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
```

-continued

```
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys Ala Pro
    450                 455                 460

Thr Ser Ser Ser Thr Lys Lys Thr Gln Leu Gln Leu Glu His Leu Leu
465                 470                 475                 480

Leu Asp Leu Gln Met Ile Leu Asn Gly Ile Asn Asn Tyr Lys Asn Pro
                485                 490                 495

Lys Leu Thr Arg Met Leu Thr Phe Lys Phe Tyr Met Pro Lys Lys Ala
            500                 505                 510

Thr Glu Leu Lys His Leu Gln Cys Leu Glu Glu Glu Leu Lys Pro Leu
        515                 520                 525

Glu Glu Val Leu Asn Leu Ala Gln Ser Lys Asn Phe His Leu Arg Pro
    530                 535                 540

Arg Asp Leu Ile Ser Asn Ile Asn Val Ile Val Leu Glu Leu Lys Gly
545                 550                 555                 560

Ser Glu Thr Thr Phe Met Cys Glu Tyr Ala Asp Glu Thr Ala Thr Ile
                565                 570                 575

Val Glu Phe Leu Asn Arg Trp Ile Thr Phe Cys Gln Ser Ile Ile Ser
            580                 585                 590
```

-continued

Thr Leu Thr
        595

<210> SEQ ID NO 9
<211> LENGTH: 723
<212> TYPE: DNA
<213> ORGANISM: Artificial
<220> FEATURE:
<223> OTHER INFORMATION: monoclonal antibody chain

<400> SEQUENCE: 9
atggaagccc cagcgcagct tctcttcctc ctgctactct ggctcccaga taccactgga 60
gaaatagtga tgacgcagtc tccagccacc ctgtctgtgt ctccagggga aagagccacc 120
ctctcctgca gatctagtca gagtcttgta caccgtaatg gaaacaccta tttacattgg 180
tacctgcaga agccaggcca gtctccaaag ctcctgattc acaaagtttc caaccgattt 240
tctggggtcc cagacaggtt cagtggcagt ggatcaggga cagatttcac actcaagatc 300
agcagagtgg aggctgagga tctgggagtt tatttctgtt ctcaaagtac acatgttcct 360
ccgctcacgt tcggtgctgg gaccaagctg gagctgaaac gaactgtggc tgcaccatct 420
gtcttcatct tcccgccatc tgatgagcag ttgaaatctg gaactgcctc tgttgtgtgc 480
ctgctgaata acttctatcc cagagaggcc aaagtacagt ggaaggtgga taacgccctc 540
caatcgggta actcccagga gagtgtcaca gagcaggaca gcaaggacag cacctacagc 600
ctcagcagca ccctgacgct gagcaaagca gactacgaga aacacaaagt ctacgcctgc 660
gaagtcaccc atcagggcct gagctcgccc gtcacaaaga gcttcaacag gggagagtgt 720
tag 723

<210> SEQ ID NO 10
<211> LENGTH: 1389
<212> TYPE: DNA
<213> ORGANISM: Artificial
<220> FEATURE:
<223> OTHER INFORMATION: monoclonal antibody chain

<400> SEQUENCE: 10
atgggatgga cctggatctt tattttaatc ctgtcggtaa ctacaggtgt ccactctgag 60
gtccaactgc tgcagtctgg acctgagctg gagaagcctg gcgcttcagt gatgatatcc 120
tgcaaggctt ctggttcctc attcactggc tacaacatga actgggtgag gcagaacatt 180
ggaaagagcc ttgaatggat tggagctatt gatccttact atggtggaac tagctacaac 240
cagaagttca agggcagggc cacattgact gtagacaaat cgtccagcac agcctacatg 300
cacctcaaga gcctgacatc tgaggactct gcagtctatt actgtgtaag cggaatggag 360
tactggggtc aaggaacctc agtcaccgtc tcctcagcct ccaccaaggg cccatcggtc 420
ttccccctgg caccctcctc caagagcacc tctgggggca cagcggccct gggctgcctg 480
gtcaaggact acttccccga accggtgacg gtgtcgtgga actcaggcgc cctgaccagc 540
ggcgtgcaca ccttcccggc tgtcctacag tcctcaggac tctactccct cagcagcgtg 600
gtgaccgtgc cctccagcag cttgggcacc cagacctaca tctgcaacgt gaatcacaag 660
cccagcaaca ccaaggtgga caagagagtt gagcccaaat cttgtgacaa aactcacaca 720
tgcccaccgt gcccagcacc tgaactcctg gggggaccgt cagtcttcct cttcccccca 780
aaacccaagg acaccctcat gatctcccgg acccctgagg tcacatgcgt ggtggtggac 840
gtgagccacg aagaccctga ggtcaagttc aactggtacg tggacggcgt ggaggtgcat 900

```
aatgccaaga caaagccgcg ggaggagcag tacaacagca cgtaccgtgt ggtcagcgtc    960

ctcaccgtcc tgcaccagga ctggctgaat ggcaaggagt acaagtgcaa ggtctccaac   1020

aaagccctcc cagcccccat cgagaaaacc atctccaaag ccaaagggca gccccgagaa   1080

ccacaggtgt acaccctgcc cccatcccgg gaggagatga ccaagaacca ggtcagcctg   1140

acctgcctgg tcaaaggctt ctatcccagc gacatcgccg tggagtggga gagcaatggg   1200

cagccggaga acaactacaa gaccacgcct cccgtgctgg actccgacgg ctccttcttc   1260

ctctatagca agctcaccgt ggacaagagc aggtggcagc aggggaacgt cttctcatgc   1320

tccgtgatgc atgaggctct gcacaaccac tacacgcaga agagcctctc cctgtccccg   1380

ggtaaatga                                                           1389
```

```
<210> SEQ ID NO 11
<211> LENGTH: 240
<212> TYPE: PRT
<213> ORGANISM: Artificial
<220> FEATURE:
<223> OTHER INFORMATION: monoclonal antibody chain

<400> SEQUENCE: 11

Met Glu Ala Pro Ala Gln Leu Leu Phe Leu Leu Leu Leu Trp Leu Pro
1               5                   10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ser Ser Gln Ser
        35                  40                  45

Leu Val His Arg Asn Gly Asn Thr Tyr Leu His Trp Tyr Leu Gln Lys
    50                  55                  60

Pro Gly Gln Ser Pro Lys Leu Leu Ile His Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Leu Gly Val Tyr Phe
            100                 105                 110

Cys Ser Gln Ser Thr His Val Pro Pro Leu Thr Phe Gly Ala Gly Thr
        115                 120                 125

Lys Leu Glu Leu Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

```
<210> SEQ ID NO 12
<211> LENGTH: 462
<212> TYPE: PRT
<213> ORGANISM: Artificial
```

<220> FEATURE:
<223> OTHER INFORMATION: monoclonal antibody chain

<400> SEQUENCE: 12

```
Met Gly Trp Thr Trp Ile Phe Ile Leu Ile Leu Ser Val Thr Thr Gly
1               5                   10                  15

Val His Ser Glu Val Gln Leu Leu Gln Ser Gly Pro Glu Leu Glu Lys
            20                  25                  30

Pro Gly Ala Ser Val Met Ile Ser Cys Lys Ala Ser Gly Ser Ser Phe
        35                  40                  45

Thr Gly Tyr Asn Met Asn Trp Val Arg Gln Asn Ile Gly Lys Ser Leu
    50                  55                  60

Glu Trp Ile Gly Ala Ile Asp Pro Tyr Tyr Gly Gly Thr Ser Tyr Asn
65                  70                  75                  80

Gln Lys Phe Lys Gly Arg Ala Thr Leu Thr Val Asp Lys Ser Ser Ser
                85                  90                  95

Thr Ala Tyr Met His Leu Lys Ser Leu Thr Ser Glu Asp Ser Ala Val
            100                 105                 110

Tyr Tyr Cys Val Ser Gly Met Glu Tyr Trp Gly Gln Gly Thr Ser Val
        115                 120                 125

Thr Val Ser Ser Ala Ser Thr Lys Gly Pro Ser Val Phe Pro Leu Ala
    130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400
```

-continued

```
Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460
```